United States Patent
David et al.

(10) Patent No.: US 10,471,139 B2
(45) Date of Patent: Nov. 12, 2019

(54) TOLL-LIKE RECEPTOR AGONISTS

(71) Applicant: The University of Kansas, Lawrence, KS (US)

(72) Inventors: Sunil Abraham David, Lawrence, KS (US); Euna Yoo, Lawrence, KS (US); Nikunj Shukla, Lawrence, KS (US); Alex Christopher Salyer, Lawrence, KS (US); Mallesh Beesu, Lawrence, KS (US); Subbalakshmi S. Malladi, Lawrence, KS (US); Cassandra Jones, Lawrence, KS (US)

(73) Assignee: The University of Kansas, Lawrence, KS (US)

( * ) Notice: Subject to any disclaimer, the term of this patent is extended or adjusted under 35 U.S.C. 154(b) by 144 days.

(21) Appl. No.: 14/909,967

(22) PCT Filed: Aug. 15, 2014

(86) PCT No.: PCT/US2014/051302
§ 371 (c)(1),
(2) Date: Feb. 3, 2016

(87) PCT Pub. No.: WO2015/023958
PCT Pub. Date: Feb. 19, 2015

(65) Prior Publication Data
US 2016/0166681 A1   Jun. 16, 2016

Related U.S. Application Data

(60) Provisional application No. 61/866,369, filed on Aug. 15, 2013, provisional application No. 62/027,904, filed on Jul. 23, 2014.

(51) Int. Cl.
*C07D 471/04* (2006.01)
*A61K 39/39* (2006.01)
*C07D 235/30* (2006.01)
*A61K 39/00* (2006.01)

(52) U.S. Cl.
CPC .......... *A61K 39/39* (2013.01); *C07D 235/30* (2013.01); *C07D 471/04* (2013.01); *A61K 2039/55511* (2013.01)

(58) Field of Classification Search
CPC .................................................. C07D 471/04
See application file for complete search history.

(56) References Cited

FOREIGN PATENT DOCUMENTS

| WO | WO-9502597 A1 * | 1/1995 | ........... C07D 213/69 |
| WO | WO-03050118 A1 * | 6/2003 | ........... C07D 471/04 |
| WO | WO 2007084728 A2 * | 7/2007 | ........... C07D 401/06 |

OTHER PUBLICATIONS

PubChem CID 2772288—National Center for Biotechnology Information. PubChem Compound Database; CID=2772288, https://pubchem.ncbi.nlm.nih.gov/compound/2772288 (accessed Jan. 12, 2017), create date Jul. 19, 2005.*
Han, H. "Targeted Prodrug Design to Optimize Drug Delivery." AAPS Pharmsci. (2000), vol. 2 (1) article 6, pp. 1-11.*
Ettmayer, P., et al. "Lessons Learned from Marketed and Investigational Prodrugs." J. Med. Chem. (2004) 47(10), pp. 2393-2404.*
Testa, B. "Prodrug research: futile or fertile?" Biochem. Pharm. (2004) 68, pp. 2097-2106.*
IUPAC. "Diastereoisomerism." (c) 1996. Available from: < https://goldbook.iupac.org/html/D/D01679.html >.*

* cited by examiner

*Primary Examiner* — Andrew D Kosar
*Assistant Examiner* — John S Kenyon
(74) *Attorney, Agent, or Firm* — Maschoff Brennan; Jonathan M. Benns

(57) ABSTRACT

Compounds described herein can be used for therapeutic purposes. The compounds can be TLR agonists, such as TLR7 or TLR8 agonists. The compounds can be included in pharmaceutical compositions and used for therapies were being a TLR agonist is useful. The pharmaceutical compositions can include any ingredients, such as carries, diluents, excipients, fillers or the like that are common in pharmaceutical compositions. The compounds can be those illustrated or described herein as well as derivative thereof, prodrug thereof, salt thereof, or stereoisomer thereof, or having any chirality at any chiral center, or tautomer, polymorph, solvate, or combinations thereof. As such, the compounds can be used as adjuvants in vaccines as well as for other therapeutic purposes described herein. The compounds can have any one of the formulae. Examples of the compounds can be reviewed in Table 1 and Table A1 for activates.

20 Claims, 13 Drawing Sheets

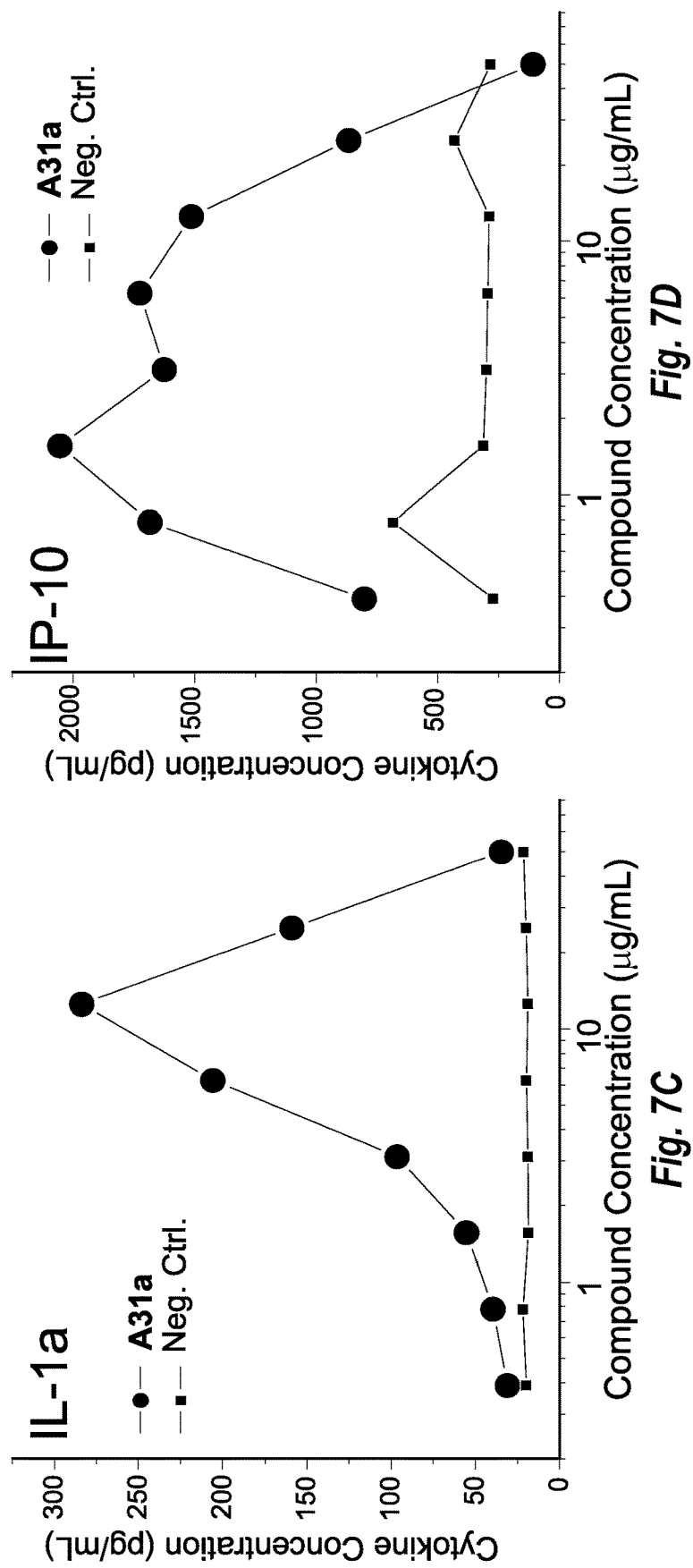

TOLL-LIKE RECEPTOR AGONISTS

CROSS-REFERENCE

This patent application claims benefit of U.S. Provisional Application Ser. No. 61/866,369 filed Aug. 15, 2013, and of U.S. Provisional Application Ser. No. 62/027,904 filed Jul. 23, 2014, which provisional applications are incorporated herein by specific reference in its entirety.

GOVERNMENT RIGHTS

This invention was made with government support under HSN272200900033C awarded by the National Institutes of Health and National Institute of Allergy and Infectious Diseases. The government has certain rights in the invention.

BACKGROUND

It has been found that host responses to pathogens can be mediated via highly coordinated mechanisms involving both innate and adaptive limbs of the immune system. The innate immune system utilizes germline-encoded pattern recognition receptors (PRRs) to detect pathogen-associated molecular patterns (PAMPs) that are distinct and unique to the pathogen. PRRs encompass a broad range of molecules that are secreted into the extracellular environment (e.g., collectins, ficolins, pentraxins, alarmins), exist in the cytosol (e.g., retinoic acid-inducible gene I-like receptors, and the nucleotide-binding domain and leucine-rich repeat-containing receptors), or are present on membranes.

Important among the transmembrane PRRs are the Toll-like receptors (TLRs), which are either expressed on the plasma membrane or in the endolysosomal compartments. At least 10 functional TLRs are encoded in the human genome, each with an extracellular domain having leucine-rich repeats (LRR) and a cytosolic domain called the Toll/IL-1 receptor (TIR) domain. The ligands for these receptors are highly conserved microbial molecules such as lipopolysaccharides (LPS) (recognized by TLR4), lipopeptides (TLR2 in combination with TLR1 or TLR6), flagellin (TLR5), single stranded RNA (TLR7 and TLR8), double stranded RNA (TLR3), CpG motif-containing DNA (recognized by TLR9), and profilin present on uropathogenic bacteria (TLR11). TLR1, -2, -4, -5, and -6 recognize extracellular stimuli, while TLR3, -7, -8 and -9 function within the endolysosomal compartment. The activation of TLRs by their cognate ligands leads to production of inflammatory cytokines, and up-regulation of major histocompatibility complex (MHC) molecules and co-stimulatory signals in antigen-presenting cells as well as activating natural killer (NK) cells (innate immune response), which lead to the priming and amplification of T-, and B-cell effector functions (adaptive immune responses).

The Type I interferon (IFN) family in humans includes approximately 20 IFN-α subtype genes in addition to individual genes encoding IFN-β, -κ, -ε and -ω; these monomeric secreted proteins bind to a single IFN-α/β receptor, which is constitutively expressed in virtually all cell types. Occupancy of TLR7 or TLR9 in antigen-presenting cells (APCs), particularly plasmacytoid dendritic cells (pDCs), leads to the induction of IFN-α/β. Although the Type I IFNs are best known historically for their antiviral activities, recent studies show that they have many essential functions in the control of adaptive immunity. First, Type I IFNs promote cross-priming through direct stimulation of DCs, leading to specific $CD8^+$ lymphocytic responses to soluble antigens. Second, Type I IFNs potently enhance the primary antibody responses to soluble antigens, inducing sustained and durable humoral responses with appropriate isotype switching, as well as the induction of immunological memory. B lymphocytes can differentiate into two distinct types of functionally polarized effectors: B-effector-1-cells (Be-1), producing a Th-1-like cytokine pattern, or Be-2, characterized by a Th-2-like profile. It is of particular interest that recent reports suggest that IFN-α may serve as an initial trigger for Be-1-biased differentiation pattern. Third, Type I interferons secondarily induce Type II IFN (IFN-γ) secretion, also driving Th-1-biased adaptive immune responses. Type I IFN-inducing TLR ligands may, therefore, hold promise as vaccine adjuvants.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIGS. 7A-7F include graphs that show proinflammatory cytokine induction profiles of compound A31a in human blood. Means of duplicate values of a representative experiment is shown.

FIGS. 8A-8B include data that shows the absence of CD69 upregulation in human natural killer cells by compound A31a. FIG. 8A shows PBMCs with primary gates on lymphocytes.

FIG. 8B shows secondary quadrant gates on lymphocytic population showing $CD3^+CD56^-$ (T cells, Quadrant A), $CD3^-CD56^-$ (nominal B cells, Quadrant B), $CD3^+CD56^+$ (cytokine-induced killer cells, Quadrant C), and CD3⁻ CD56⁺ (natural killer cells, Quadrant D).

DETAILED DESCRIPTION

Figure 1:
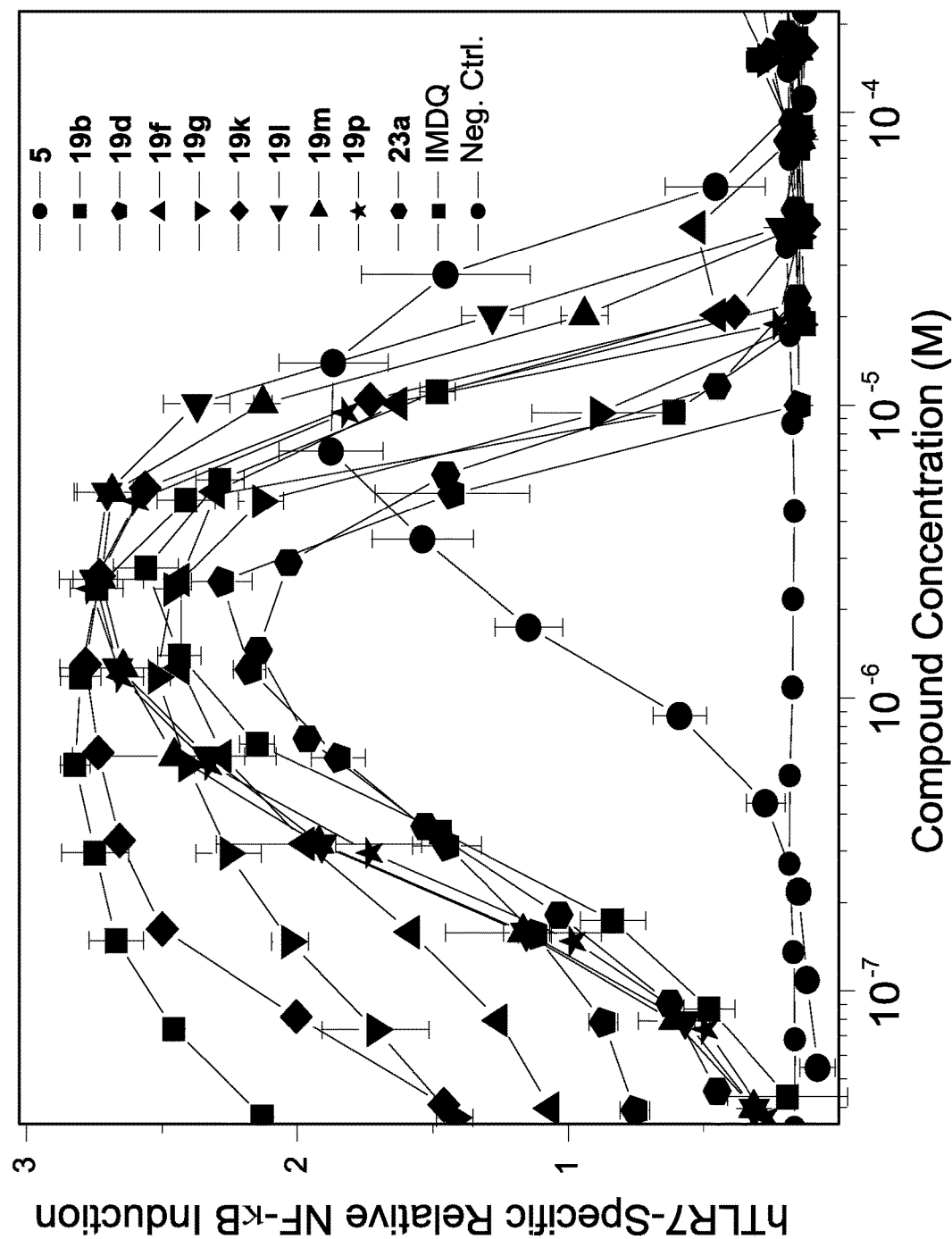
FIG. 1 includes a graph that shows TLR7 agonistic activity of imidazopyridine compounds. Data points represent means and standard deviations on quadruplicates.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present invention relates to compounds described herein. The compounds can be TLR agonists, such as TLR7 or TLR8 agonists. The compounds can be included in pharmaceutical compositions and used for therapies where being a TLR agonist is useful. The pharmaceutical compositions can include any ingredients, such as carries, diluents, excipients, fillers or the like that are common in pharmaceutical compositions. The compounds can be those illustrated or described herein as well as derivative thereof, prodrug thereof, salt thereof, or stereoisomer thereof, or having any chirality at any chiral center, or tautomer, polymorph, solvate, or combinations thereof.

In one embodiment, a compound of the invention can include the structure of Formula 1 or 1A, derivative thereof, prodrug thereof, salt thereof, or stereoisomer thereof, or having any chirality at any chiral center, or tautomer, polymorph, solvate, or combinations thereof.

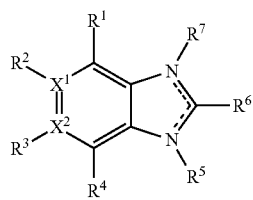

Formula 1

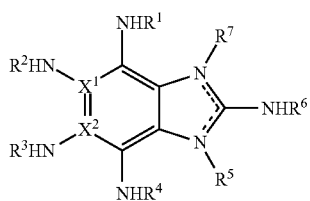

Formula 1A

In Formula 1 or 1A the variables can have the following values: one of the dashed lines may be a bond and the other nothing; $X^1$ and $X^2$ are independently C or N, and preferably one is C and the other is N or both are C; and $R^1$-$R^7$ are each independently selected from (a) hydrogen; (b) $C_{1-6}$alkyl, $C_{2-6}$alkenyl, $C_{2-6}$alkynyl, $C_{3-7}$cycloalkyl, $C_{6-14}$ aryl, $C_{7-15}$ aralkyl, heteroaryl, or heterocyclyl; or (c) —C(O)$R^{1a}$, —C(O)CH(NR$^{1b}$R$^{1c}$)R$^{1a}$, —C(O)CH(N(R$^{1c}$)C(O)R$^{1b}$)R$^{1a}$, —C(O)CH(N(R$^{1c}$)C(O)OR$^{1b}$)R$^{1a}$, C(O)CH(N(R$^{1c}$)C(O)NR$^{1b}$R$^{1d}$)R$^{1a}$, C(O)OR$^{1a}$, —C(O)NR$^{1b}$R$^{1c}$, —C(NR$^{1a}$)NR$^{1b}$R$^{1c}$, —P(O)(OR$^{1a}$)R$^{1d}$, CH$_2$P(O)(OR$^{1a}$)R$^{1d}$, —S(O)R$^{1a}$, —S(O)$_2$R$^{1a}$, —S(O)NR$^{1b}$R$^{1c}$, or —S(O)$_2$NR$^{1b}$R$^{1c}$; (d) two adjacent R groups (e.g., $R^1$ and $R^2$, $R^2$ and $R^3$, $R^3$ and $R^4$, $R^5$ and $R^6$, or $R^6$ and $R^7$) form a cyclic group, such as an aryl, heteroaryl, polyaryl, polyheteroaryl, or cycloalkyl or cycloheteroaryl; or (e) $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, $C_6$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo, $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO⁻), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—C≡N), isocyano (—N⁺≡C⁻), cyanato (—O—C≡N), isocyanato (—O—N⁺≡C⁻), isothiocyanato (—S—C≡N), azido (—N=N⁺=N⁻), formyl (—(CO)—H), thioformyl (—(CS)—H), amino (—NH$_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—S$_2$—O⁻), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), phosphono (—P(O)(OH)$_2$), phosphonato (—P(O)(O⁻)$_2$), phosphinato (—P(O)(O—)), phospho (—PO$_2$), phosphino (—PH$_2$); (f) derivatives thereof; and (g) combinations thereof. Wherein each R group is optionally substituted by a substituent Q, which substituent Q is defined as $R^1$. Wherein each R group variable is optionally —NHR, such that $R^1$ is —NHR$^{a1}$, $R^2$ is —NHR$^{a2}$, $R^3$ is —NHR$^{a3}$, $R^4$ is —NHR$^{a4}$, $R^5$ is —NHR$^{a5}$, $R^6$ is —NHR$^{a6}$, and $R^7$ is —NHR$^{a7}$. Wherein $R^{a1}$, $R^{a2}$, $R^{a3}$, $R^{a4}$, $R^{a5}$, $R^{a6}$, $R^{a7}$, $R^{1a}$, $R^{1b}$, $R^{1c}$, or Rid are each independently as defined for $R^1$, such as the selections (a), (b), (d), (e), (f), and (g). In one option, $R^{1a}$, $R^{1b}$, $R^{1c}$, or $R^{1d}$ are not the selection (c) that recites variables of $R^{a7}$, $R^{1a}$, $R^{1b}$, $R^{1c}$, or Rid, or the variable iteration can be 1, 2, or 3 iterations of $R^{a7}$, $R^{1a}$, $R^{1b}$, $R^{1c}$, or Rid variables to a definite value. Each hetero, such as heteroaryl or heteroalkyl (e.g., alkyl with hetero atoms and carbon atoms), can include a backbone atom being other can C, such as being N, O, P, or S. Each alkyl can be $C_1$-$C_{12}$ alkyl, $C_1$-$C_8$ alkyl, or $C_1$-$C_6$ alkyl. Each alkenyl can be $C_2$-$C_{12}$ alkenyl, $C_2$-$C_8$ alkenyl, or $C_2$-$C_6$ alkenyl. Each alkynyl can be $C_2$-$C_{12}$ alkynyl, $C_2$-$C_8$ alkynyl, or $C_2$-$C_6$ alkynyl. Each aryl can be monoaryl or polyaryl and can be $C_5$-$C_P$ aryl, wherein P can be any integer that results in being aromatic. Each polyaryl or polycycle can be 5,5-fused, 5,6-fused, or 6,6 fused with homo or hetero backbone, such as homoarylene or heteroarylene. When $X^1$ and/or $X^2$ is N, then $R^2$ can be nothing. When one of the dashed lines may be a bond and the other nothing, the N having the double bond is devoid of a substituent, such that one of $R^5$ or $R^7$ is nothing. Specific examples of values of the X and R group variables and examples of compounds formed therefrom are included in Table 1 and Table A1.

In one embodiment, a compound of the invention can include the structure of Formula 2 or 2A, derivative thereof, prodrug thereof, salt thereof, or stereoisomer thereof, or having any chirality at any chiral center, or tautomer, polymorph, solvate, or combinations thereof. In Formula 2 or 2A, the variables can be as defined for Formula 1.

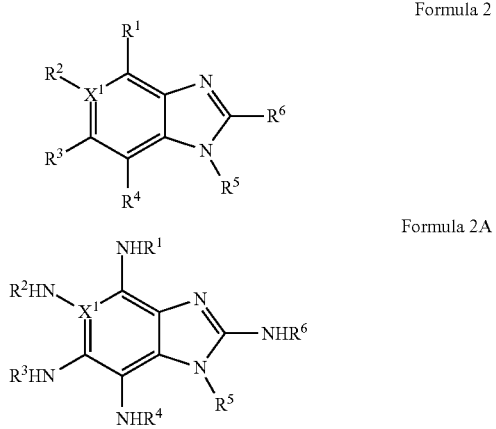

In certain embodiments, each R group of Formulae 1, 1A, 2, and 2A are each independently selected from the recitations above or the following: 2(R)-(dimethylamino)propionyl, 2-(methoxycarbonylamino)propionyl, 2(R)-(methoxycarbonylamino)propionyl, 2-(ethoxycarbonylamino)propionyl, 2(R)-(methoxycarbonyl-amino)-3-methoxypropionyl, 2(R)-(methoxycarbonylamino)-3-aminocarbonyl-propionyl, 2-(methoxycarbonylamino)-2-methylpropionyl, 2(R)-(methoxycarbonylamino)-3(R)-hydroxy-butanoyl, 2(R)-(methoxycarbonylamino)-3(S)-hydroxybutanoyl, 2(R)-(methoxycarbonyl-amino)-3-methylbutanoyl, 2(S)-(methoxycarbonylamino)-3-methylbutanoyl, 2(R)-(ethoxycarbonyl-amino)-3-methylbutanoyl, 2(S)-(ethoxycarbonylamino)-3-methylbutanoyl, 2(R)-(isoproxycarbonyl-amino)-3-methylbutanoyl, 2(S)-(isopropoxycarbonylamino)-3-methylbutanoyl, 2(R)-(tert-butoxycarbonylamino)-3-methylbutanoyl, 2(S)-(tert-butoxycarbonylamino)-3-methylbutanoyl, 2(R)-(methoxycarbonylamino)-3-hydroxy-3-methylbutanoyl, 2-(methoxycarbonylamino)-2-cyclopropyl-acetyl, 2-(methoxycarbonylamino)pentanoyl, 2-(methoxycarbonylamino)pent-4-enoyl, 1-(methoxycarbonylamino)cyclopropylcarbonyl, 1-(methoxycarbonylamino)-cyclobutylcarbonyl, 1-(methoxycarbonylamino)-cyclopentyl-carbonyl, 2(R)-(methoxycarbonylamino)-2-phenylacetyl, 2(R)-(ethoxycarbonylamino)-2-phenylacetyl, 2(R)-(isopropoxycarbonylamino)-2-phenylacetyl, 2(R)-(tert-butoxycarbonylamino)-2-phenylacetyl, 2(S)-(tert-butoxycarbonylamino)-2-phenylacetyl, 2(R)-(methoxycarbonyl-amino)-2-(2-chlorophenyl)acetyl, 2(R)-(dimethylamino)-2-phenylacetyl, 2-(dimethylamino)-2-(4-nitrophenyl)acetyl, 2-(dimethylamino)-2-(2-fluorophenyl)acetyl, 2(R)-(dimethylamino)-2-(2-fluorophenyl)acetyl, 2(S)-(dimethylamino)-2-(2-fluorophenyl)acetyl, 2-(dimethyl-amino)-2-(3-fluorophenyl)acetyl, 2-(dimethylamino)-2-(2-chlorophenyl)acetyl, 2(R)-(dimethylamino)-2-(2-chlorophenyl)acetyl, 2-(dimethylamino)-2-(3-chlorophenyl)acetyl, 2-(dimethylamino)-2-(4-chlorophenyl)acetyl, 2-(dimethylamino)-2-(2-trifluoromethyl-phenyl)acetyl, 2-(dimethyl-amino)-2-(3-trifluoromethylphenyl)acetyl, 2-(dimethylamino)-2-(thien-2-yl)acetyl, 2-(dimethyl-amino)-2-(thien-3-yl)acetyl, 2-(dimethylamino)-2-(2-methylthiazol-4-yl)acetyl, 2-(dimethylamino)-2-(benzothien-3-yl)acetyl, 2-(dimethylamino)-2-(2-methyl-benzothiazol-5-yl)acetyl, 2-(dimethylamino)-2-(benzoisoxazol-3-yl)acetyl, 2-(dimethylamino)-2-(quinolin-3-yl)acetyl, 2(R)-(diethylamino)-2-phenylacetyl, 2(R)-(methylethylamino)-2-phenylacetyl, 2-(dimethylamino)-2-naphth-1-ylacetyl, 2(R)-(pyrrolidin-1-yl)-2-phenylacetyl, 2-(3(S)-fluoropyrrolidin-1-yl)-2-phenylacetyl, 2(R)-(morpholin-4-yl)-2-phenylacetyl, 2(R)-(piperidin-1-yl)-2-phenylacetyl, 2(R)-(piperidin-1-yl)-2-(2-fluorophenyl)acetyl, 2-(4-hydroxy-piperidin-1-yl)-2-phenylacetyl, 2-(4-phenylpiperidin-1-yl)-2-phenylacetyl, 2(R)-(4-hydroxy-4-methylpiperidin-1-yl)-2-phenylacetyl, 2(R)-(4-hydroxy-4-phenylpiperidin-1-yl)-2-phenylacetyl, 2-(3-oxopiperazin-1-yl)-2-phenylacetyl, 2-(4-methylpiperazin-1-yl)-2-phenylacetyl, 2-(dimethylamino)-2-(pyridin-2-yl)acetyl, 2-(dimethylamino)-2-(pyridin-3-yl)acetyl, 2-(dimethylamino)-2-(pyridin-4-yl)acetyl, 2-(dimethylamino)-2-(6-chloropyridin-3-yl)acetyl, 2-(2-dimethylaminomethyl)phenylacetyl, 2-(2-pyrrolin-1-ylmethyl)phenylacetyl, 2-(2-piperidin-1-ylmethyl)phenylacetyl, 2-(2-morpholin-4-ylmethyl)phenylacetyl, 2-(2-(4-methylpiperazin-1-ylmethyl)phenylacetyl, 1-methylpyrrolidine-2(R)-carbonyl, 1-methyl-4(R)-fluoro-pyrrolidine-2(R)-carbonyl, 2-(R)-(methylaminoarbonylamino)-2-phenylacetyl, 2-(R)-(ethylaminoarbonylamino)-2-phenylacetyl, 2(R)-(cyclopentylaminoarbonylamino)-2-phenylacetyl, 2(R)-(dimethylaminoarbonylamino)-2-phenylacetyl, (N,N-benzylmethyl-amino)acetyl, and 2-(N,N-benzylmethylamino)-3-methylbutanoyl. In one aspect, $R^{a7}$, $R^{1a}$, $R^{1b}$, $R^{1c}$, or $R^{1d}$ can be the foregoing chemical entities.

The compounds provided herein may be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of skill in the art will recognize that administration of a compound in its (R) form is equivalent, for compounds that undergo epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

TLR7 Agonists

In one embodiment, a compound of the invention can include the structure of Formula 3 or 3A, derivative thereof, prodrug thereof, salt thereof, or stereoisomer thereof, or having any chirality at any chiral center, or tautomer, polymorph, solvate, or combinations thereof. In Formula 3 or 3A, the variables can be as defined for Formula 1.

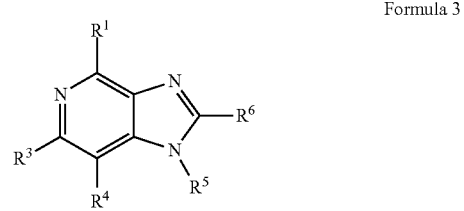

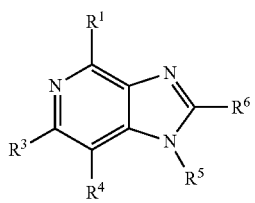

Formula 3A

In one embodiment, a compound of the invention can include the structure of Formula 4 or 4A, derivative thereof, prodrug thereof, salt thereof, or stereoisomer thereof, or having any chirality at any chiral center, or tautomer, polymorph, solvate, or combinations thereof. In Formula 4 or 4A, the variables can be as defined for Formula 1. Wherein $R^8$ is as defined for $R^1$.

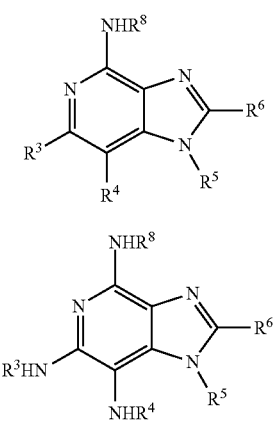

Formula 4

Formula 4A

In one embodiment, a compound of the invention can include the structure of Formula 5 or 5A, derivative thereof, prodrug thereof, salt thereof, or stereoisomer thereof, or having any chirality at any chiral center, or tautomer, polymorph, solvate, or combinations thereof. In Formula 5 or 5A, the variables can be as defined for Formula 1.

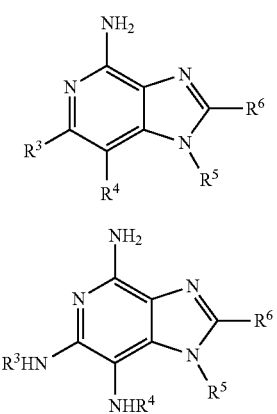

Formula 5

Formula 5A

In one embodiment, a compound of the invention can include the structure of Formula 6 or 6A, derivative thereof, prodrug thereof, salt thereof, or stereoisomer thereof, or having any chirality at any chiral center, or tautomer, polymorph, solvate, or combinations thereof. In Formula 6 or 6A, the variables can be as defined for Formula 1.

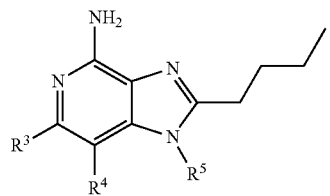

Formula 6

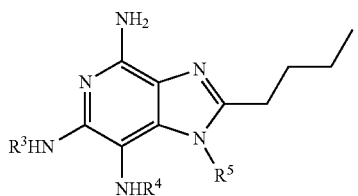

Formula 6A

In one embodiment, a compound of the invention can include the structure of Formula 7 or 7A, derivative thereof, prodrug thereof, salt thereof, or stereoisomer thereof, or having any chirality at any chiral center, or tautomer, polymorph, solvate, or combinations thereof. In Formula 7 or 7A, the variables can be as defined for Formula 1.

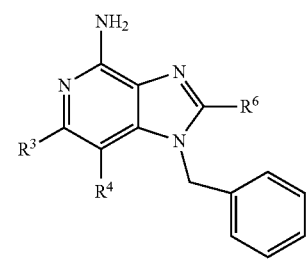

Formula 7

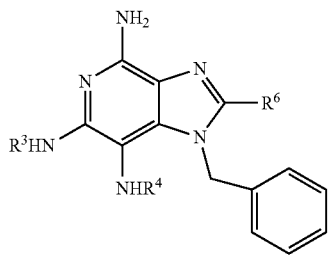

Formula 7A

In one embodiment, a compound of the invention can include the structure of Formula 8 or 8A, derivative thereof, prodrug thereof, salt thereof, or stereoisomer thereof, or having any chirality at any chiral center, or tautomer, polymorph, solvate, or combinations thereof. In Formula 8 or 8A, the variables can be as defined for Formula 1.

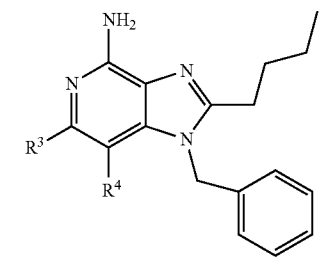

Formula 8

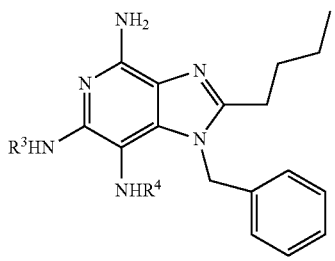

Formula 8A

In one embodiment, a compound of the invention can include the structure of Formula 9 or 9A, derivative thereof, prodrug thereof, salt thereof, or stereoisomer thereof, or having any chirality at any chiral center, or tautomer, polymorph, solvate, or combinations thereof. In Formula 9 or 9A, the variables can be as defined for Formula 1.

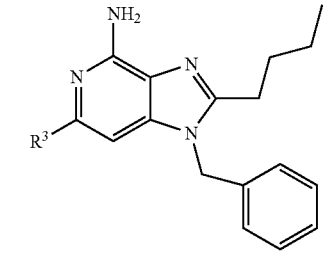

Formula 9

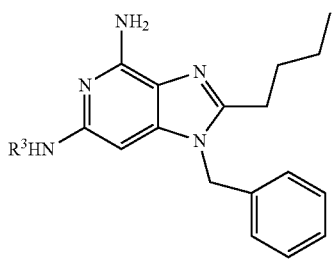

Formula 9A

In one embodiment, a compound of the invention can include the structure of Formula 10 or 10A, derivative thereof, prodrug thereof, salt thereof, or stereoisomer thereof, or having any chirality at any chiral center, or tautomer, polymorph, solvate, or combinations thereof. In Formula 10 or 10A, the variables can be as defined for Formula 1.

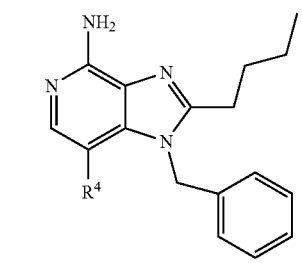

Formula 10

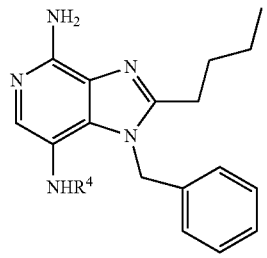

Formula 10A

For Formulae 1, 1A, 2, 2A, 3, 3A, 4, 4A, 5, 5A, 6, 6A, 7, 7A, 8, 8A, 9, 9A, 10, and 10A: $R^1$ can be hydrogen; one of $X^1$ or $X^2$ is N and the other is C, then $R^2$ can be nothing; $R^3$ or $R^4$ can be devoid of a polycycle when both do not cooperate to form a cycle or polycycle; $R^5$ can include a benzyl, $R^6$ can include an alkyl, such as a $C_1$-$C_{24}$ alkyl (e.g., $C_1$-$C_4$ alkyl); and $R^7$ can be nothing. In one aspect, $R^3$ and/or $R^4$ can independently be the same as defined for $R^3$ groups as illustrated in Table 1 for active compounds. In one aspect, $R^3$ and/or $R^4$ can independently be the same as defined for $R^3$ groups as illustrated in Table 1 for active compounds but without the —NH group. Conversely, $R^3$ and/or $R^4$ can independently be the same as defined for $R^3$ groups as illustrated in Table 1 for inactive compounds by also having the —NH group linking the R group to the aryl ring.

For Formulae 1, 1A, 2, 2A, 3, 3A, 4, 4A, 5, 5A, 6, 6A, 7, 7A, 8, 8A, 9, 9A, 10, and 10A, the compounds can be consistent with the following. In one aspect, $R^3$ and/or $R^4$ can independently be devoid of $R^3$ groups as illustrated in Table 1 for inactive compounds. In one aspect, $R^1$ with $R^3$ and/or $R^4$ can independently be devoid of $R^1$ and $R^3$ group combinations as illustrated in Table 1 for inactive compounds. In one aspect, $R^3$ and/or $R^4$ can independently be devoid of $R^1$ group combinations as illustrated in Table 1 for inactive compounds. In one aspect, $R^1$ can independently be devoid of $R^1$ groups that are not hydrogen as illustrated in Table 1 for inactive compounds. In one aspect, Formulae 1, 1A, 2, 2A, 3, 3A, 4, 4A, 5, 5A, 6, 6A, 7, 7A, 8, 8A, 9, 9A, 10, and 10A and the compounds of the invention specifically exclude compounds illustrated in Table 1 as being inactive compounds, thereby specifically exclude the R groups or R group combinations that result in inactivity. However, one R group of an inactive compound may be active in combination with a different R group.

In one embodiment, a compound of the invention can include the structure of Formula 11 or 11A, derivative thereof, prodrug thereof, salt thereof, or stereoisomer thereof, or having any chirality at any chiral center, or tautomer, polymorph, solvate, or combinations thereof. In Formula 11 or 11A, the variables can be as defined for Formula 1. Accordingly, wherein $R^9$, $R^{10}$, $R^{11}$ are each independently as defined for $R^3$ and $R^4$. Accordingly, wherein $R^9$ and $R^{10}$ can form a cyclic group, such as aryl, hetero aryl, polyaryl, polyheteroaryl, cycloalkyl, cycloheteroalkyl, polycycloalkyl, or polycycloheteroalkyl. $R^{11}$ can be substituted onto either carbon or both carbons not attached to $R^9$ and $R^{10}$. In one example, Formula 11 or 11A can be compound 30.

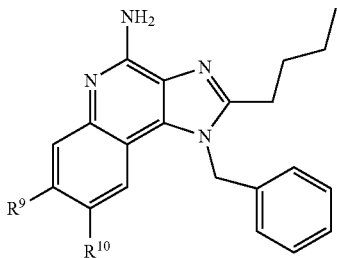

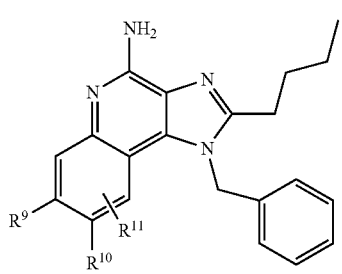

TLR8 Agonists

In one embodiment, a compound of the invention can include the structure of one of Formula 12, Formula 13, Formula 14, Formula 15, Formula 16, or Formula 17, derivative thereof, prodrug thereof, salt thereof, or stereoisomer thereof, or having any chirality at any chiral center, or tautomer, polymorph, solvate, or combinations thereof. In Formula 12, Formula 13, Formula 14, Formula 15, Formula 16, or Formula 17, the variables can be as defined for Formula 1.

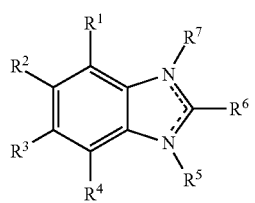

Formula 12

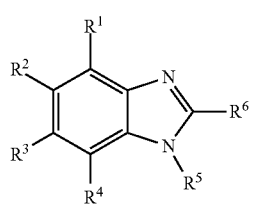

Formula 13

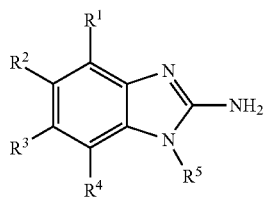

Formula 14

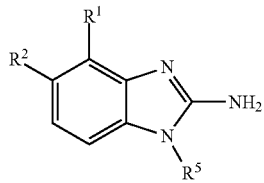

Formula 15

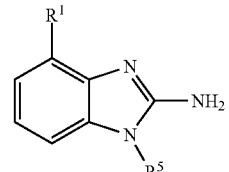

Formula 16

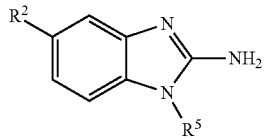

Formula 17

For Formulae 1, 1A, 2, 2A, 12, 13, 14, 15, 16, and 17: $R^1$, $R^2$, $R^3$, and/or $R^4$ each independently can be hydrogen or a short alkyl (e.g., $C_1$-$C_6$) or short alkoxy (e.g., $C_1$-$C_6$), amine, or short alkylamine (e.g., $C_1$-$C_6$), or hydroxyl; one of $X^1$ and $X^2$ are C; $R^1$ or $R^2$ can be devoid of an aryl or polyaryl when both do not cooperate to form an aryl or polyaryl; $R^1$ or $R^2$ can cooperate to form an aryl or polyaryl; $R^5$ can include a short alkyl (e.g., $C_1$-$C_6$) such as methyl, ethyl, propyl, butyl, pentyl, hexyl, heptyl, or octyl, substituted or unsubstituted; $R^5$ can be devoid of an aryl or alkylaryl, or ester; $R^6$ can include an amine; and $R^7$ can be nothing. In one aspect, $R^1$ and/or $R^2$ can independently be the same as defined for $R^1$ and/or $R^2$ groups as illustrated in Table A1 for active compounds. In one aspect, $R^3$ and/or $R^4$ can independently be the same as defined for $R^4$ and/or $R^4$ groups as illustrated in Table A1 for active compounds. In one aspect, $R^5$ and/or $R^6$ can independently be the same as defined for $R^5$ and/or $R^6$ groups as illustrated in Table A1 for active compounds.

For Formulae 1, 1A, 2, 2A, 12, 13, 14, 15, 16, and 17, the compounds can be consistent with the following. In one aspect, $R^1$ and/or $R^2$ can independently be devoid of $R^1$ and/or $R^2$ groups as illustrated in Table A1 for inactive compounds. In one aspect, $R^1$ and $R^2$ can independently be devoid of $R^1$ and $R^2$ group combinations as illustrated in Table A1 for inactive compounds.

In one aspect, $R^5$ can independently be devoid of $R^5$ groups as illustrated in Table A1 for inactive compounds. In one aspect, $R^1$-$R^4$ can independently be devoid of $R^1$-$R^4$ groups that are not hydrogen as illustrated in Table 1 for inactive compounds. In one aspect, Formulae 1, 1A, 2, 2A, 12, 13, 14, 15, 16, and 17 and the compounds of the invention specifically exclude compounds illustrated in Table A1 as being inactive compounds, thereby specifically exclude the R groups or R group combinations that result in inactivity. However, one R group of an inactive compound may be active in combination with a different R group. In one aspect, $X^1$ and/or $X^2$ can exclude N. In one aspect, $R^3$ and $R^4$ are hydrogen for each compound for these formulae.

In one embodiment, a compound of the invention can include the structure of Formula 18 or 18A, derivative thereof, prodrug thereof, salt thereof, or stereoisomer thereof, or having any chirality at any chiral center, or tautomer, polymorph, solvate, or combinations thereof. In Formula 18 or 18A, the variables can be as defined for Formula 1. Accordingly, wherein $R^9$, $R^{10}$, $R^{11}$ are each independently as defined for $R^1$ and $R^2$. Accordingly, wherein $R^9$ and $R^{10}$ can form a cyclic group, such as aryl, hetero aryl, polyaryl, polyheteroaryl, cycloalkyl, cycloheteroalkyl, polycycloalkyl, or polycycloheteroalkyl. $R^{11}$ can be substituted onto either carbon or both carbons not attached to $R^9$ and $R^{10}$. In one example, Formula 18 or 18A can be compound A23, but exclude compounds A13 and A18.

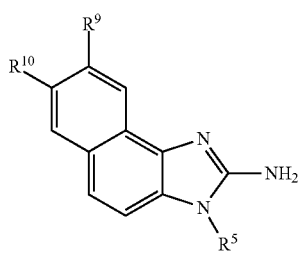

Formula 18

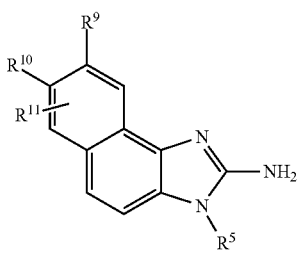

Formula 18A

The compounds described herein can be included in pharmaceutical compositions including a single enantiomer, a racemic mixture, a mixture of diastereomers, or an isotopic variant thereof; or a pharmaceutically acceptable salt, solvate, or prodrug thereof; in combination with one or more pharmaceutically acceptable excipients or carriers.

TLR7

Engagement of TLR7 in plasmacytoid dendritic cells leads to the induction of IFN-α/β which plays essential functions in the control of adaptive immunity. 1-Benzyl-2-butyl-1H-imidazo[4,5-c]pyridin-4-amine was found to be a pure TLR7-agonist with negligible activity on TLR8. Increase in potency was observed in $N^6$-substituted analogues, especially in those compounds with electron-rich substituents. Direct aryl-aryl connections at $C^6$ abrogated activity, but TLR7 agonism was reinstated in 6-benzyl and 6-phenethyl analogues. Consistent with the pure TLR7-agonistic behavior, prominent IFN-α induction in human PBMCs was observed with minimal proinflammatory cytokine induction. A benzologue of imidazoquinoline was also synthesized which showed substantial improvements in potency over the parent imidazopyridine. Distinct differences in 1N-substituted analogues were observed with respect to IFN-α induction in human PBMCs on the one hand, and CD69 upregulation in lymphocytic subsets, on the other.

In one embodiment, the compounds of the invention that are TLR7 agonists can function in protocols for immune activation, such as IFN-α/β/γ and cytokine induction. The compounds can be small-molecule agonists of TLR7 and be immunostimulatory by being potent inducers of Type I IFN and evoke dominant proinflammatory cytokine responses, suggesting that they may be effective, yet safe vaccine adjuvants. Small molecule TLR7 agonists can be used as orally bioavailable, endogenous Type I IFN inducers for the management of chronic viral diseases, such as hepatitis C and hepatitis B.

The compounds of the invention can be imidazopyridine derivatives with alkyl groups at $C^6$ and/or $C^7$ positions, or can have substituents at $C^2$, or substituents at the $N^1$ position. The compounds can be 1H-imidazo[4,5-c]pyridine analogues with modifications at the $N^4$- and/or $C^6$ and/or $C^7$ positions. The parent imidazopyridine compound, 1-benzyl-2-butyl-1H-imidazo[4,5-c]pyridin-4-amine, exhibits moderate TLR7-agonistic activity. However, $N^4$-acyl or -alkyl substitutions abrogated activity in some instances. The majority of $C^6$ derivatives bearing aryl groups were also inactive, but analogues with $N^6$-benzyl substituents gained TLR7-specific activity. Particular $N^6$ substituents were found to augment TLR7-specific agonistic potency without compromising specificity at TLR7, which is consistent with their pure TLR7 activity, and undetectable TLR8 agonism, these compounds potently induced IFN-α in human peripheral blood mononuclear cells (PBMCs), upregulated CD69 in lymphocytic subsets, and yet showed very weak proinflammatory cytokine-inducing activities. Strong Type I IFN inducers, especially in conjunction with attenuated proinflammatory profiles are expected to be potently adjuvantic without inducing prominent local or systemic inflammation. In one embodiment, the present invention utilizes TLR7 agonists as described herein as vaccine adjuvants that can be potently immunostimulatory without prominently activating inflammatory programs in human whole blood model systems. SAR studies on the imidazoquinolines established that $N^1$-benzyl and $C^2$-butyl substituents were optimal.

The compounds of the invention can be 1-benzyl-2-butyl-1H-imidazo[4,5-c]pyridin-4-amine (compound 5), or derivatives thereof. Compound 5 can be prepared following the synthetic strategy described in Scheme 1). Compound 5 was found to possess TLR7-specific agonistic activity ($EC_{50}$: 1.57 μM, FIG. 1, Table 1), with negligible TLR8 activity. The potency of the lead TLR7-specific imidazoquinoline (e.g., 1-benzyl-2-butyl-1H-imidazo[4,5-c]quinolin-4-amine) was 0.06 μM (FIG. 1). Scheme 1 is as follows.

Scheme 1 reagents:

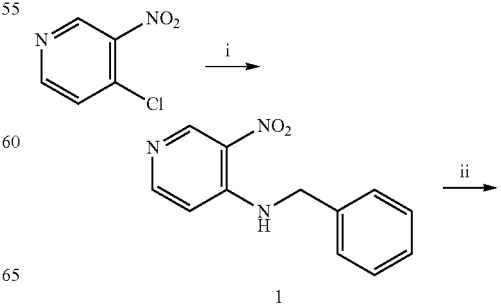

-continued

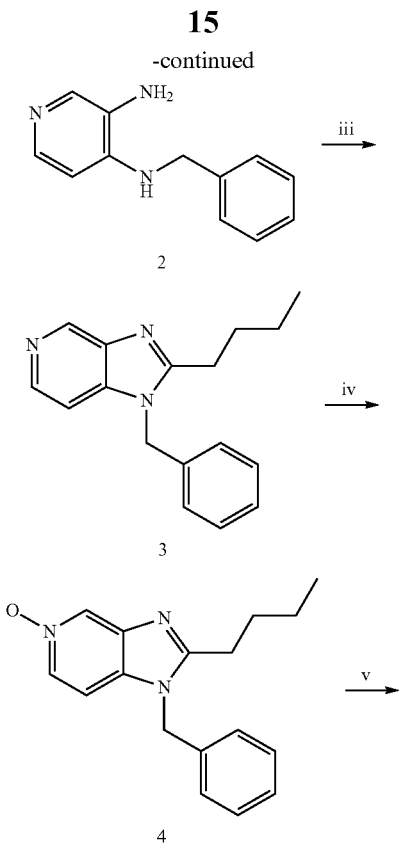

2

3

4

5

(i) BnNH₂, NEt₃, CH₂Cl₂; (ii) Zn, HCOONH₄, MeOH; (iii) a. C₄H₉COCl, NEt₃, THF; b. NaOH, EtOH; (iv) mCPBA, CHCl₃; (v) a. Benzoyl isocyanate, CH₂Cl₂; b. NaOMe, MeOH.

From compound 5, acylation resulting in compound 6a and compound 6b (e.g., see Scheme 2) of the $C^4$—NH₂ resulted in complete abrogation of activity (Table 1). C6-modified analogues were synthesized via an alternate route.

Scheme 2 reagents:

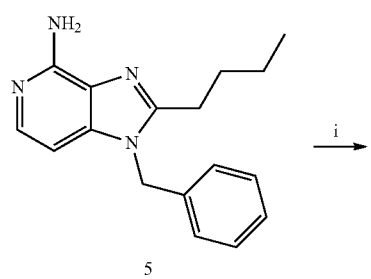

5

-continued

16

Compound 6a; R = CH₃
Compound 6b; R = C₃H₇
(i) RCOCl, NEt₃, CH₂Cl₂.

It was found that nitration of 4-amino-2-chloropyridine resulted, as expected, in a mixture of the 3- and 5-nitro intermediates in compound 7a and compound 7b, which were taken forward to obtain the 4- and 6-chloroimidazopyridines of compound 10a and compound 10b (Scheme 3). Excellent chromatographic separation of these advanced intermediates was possible. Pd-catalyzed C—N cross-coupling reactions using n-butylamine and benzylamine furnished the $C^4$—N-alkylated analogues of compound 11a and compound 11b, respectively (see Scheme 3). A 4-butoxy analogue compound 11c was also obtained by ipso-chloro displacement with 1-butanol. Compounds 11a-c were, however, inactive (Table 1).

Scheme 3 reagents:

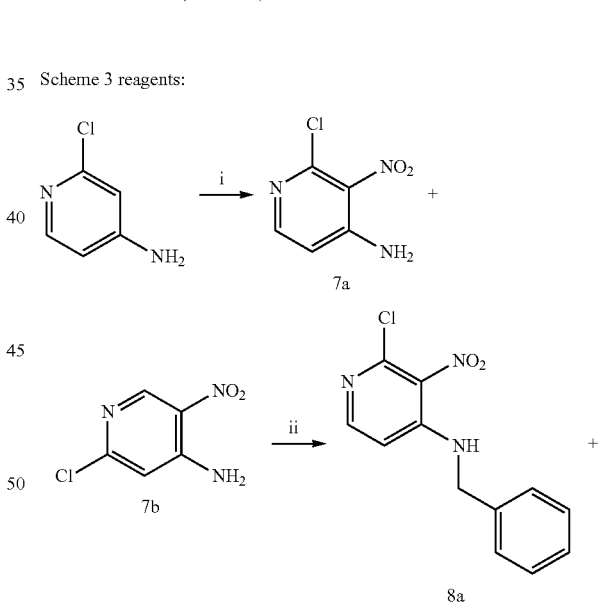

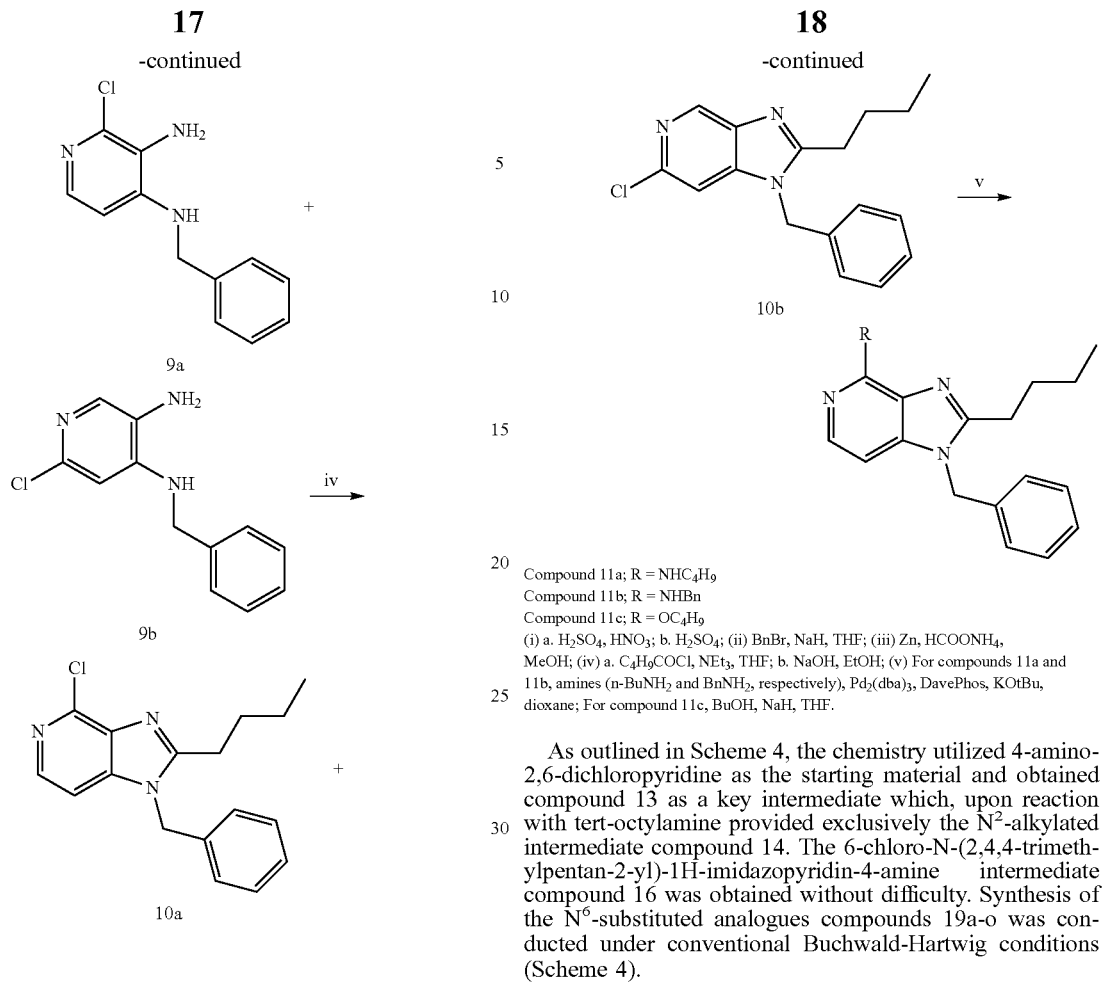

Compound 11a; R = NHC$_4$H$_9$
Compound 11b; R = NHBn
Compound 11c; R = OC$_4$H$_9$ (i) a. H$_2$SO$_4$, HNO$_3$; b. H$_2$SO$_4$; (ii) BnBr, NaH, THF; (iii) Zn, HCOONH$_4$, MeOH; (iv) a. C$_4$H$_9$COCl, NEt$_3$, THF; b. NaOH, EtOH; (v) For compounds 11a and 11b, amines (n-BuNH$_2$ and BnNH$_2$, respectively), Pd$_2$(dba)$_3$, DavePhos, KOtBu, dioxane; For compound 11c, BuOH, NaH, THF.

As outlined in Scheme 4, the chemistry utilized 4-amino-2,6-dichloropyridine as the starting material and obtained compound 13 as a key intermediate which, upon reaction with tert-octylamine provided exclusively the N$^2$-alkylated intermediate compound 14. The 6-chloro-N-(2,4,4-trimethylpentan-2-yl)-1H-imidazopyridin-4-amine intermediate compound 16 was obtained without difficulty. Synthesis of the N$^6$-substituted analogues compounds 19a-o was conducted under conventional Buchwald-Hartwig conditions (Scheme 4).

Scheme 4 reagents:

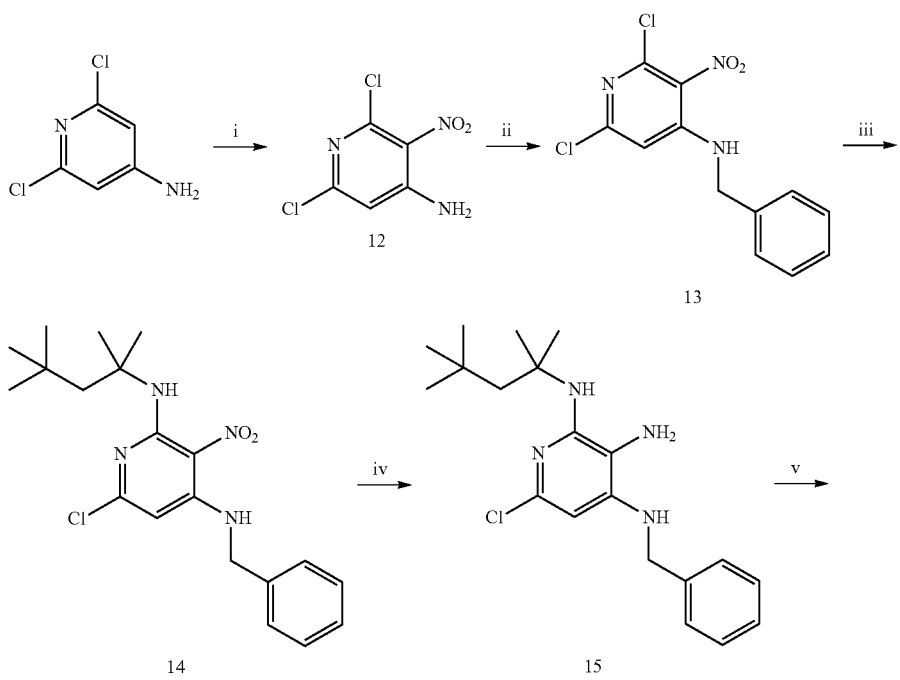

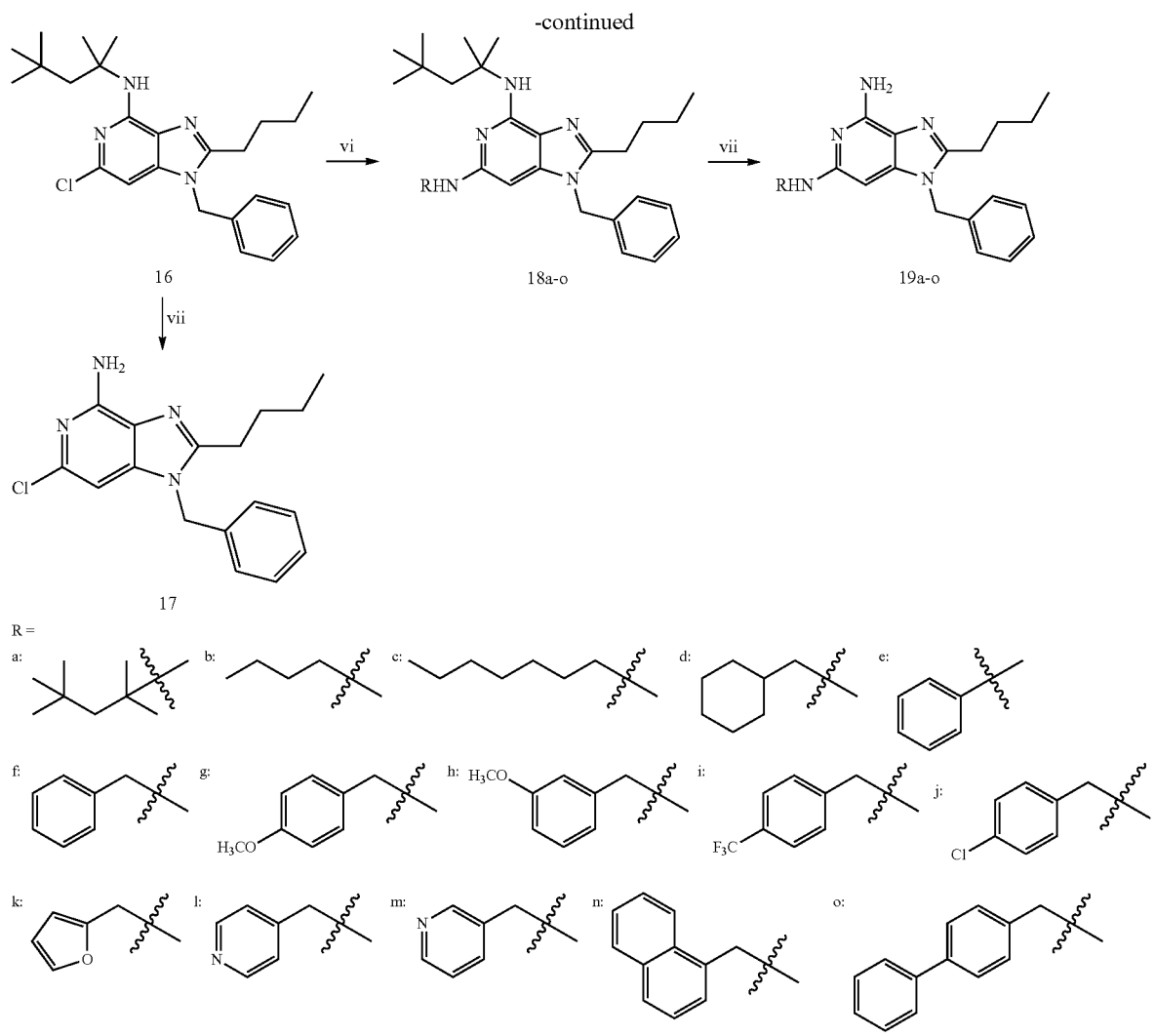

(i) a. H₂SO₄, HNO₃; b. H₂SO₄; (ii) BnBr, NaH, THF; (iii) t-Octylamine, NEt₃, CH₂Cl₂; (iv) Zn, HCOONH₄, MeOH; (v) a. C₄H₉COCl, NEt₃, THF; b. NaOH, EtOH; (vi) RNH₂, Pd₂(dba)₃, DavePhos, KOtBu, dioxane; (vii) HCl.

TLRs signal via ligand-induced dimerization, but since that the crystal structure of human TLR7 and of its ligand binding modes are as yet unknown, intermediate compound 16 was used in constructing 'dimeric' imidazopyridines (using p- and m-xylylenediamine, see Scheme 5) to ascertain if such pre-organized dimeric ligands could yield high-potency agonists. Compound 19p; R=p-CH₂NH₂

Scheme 5 reagents:

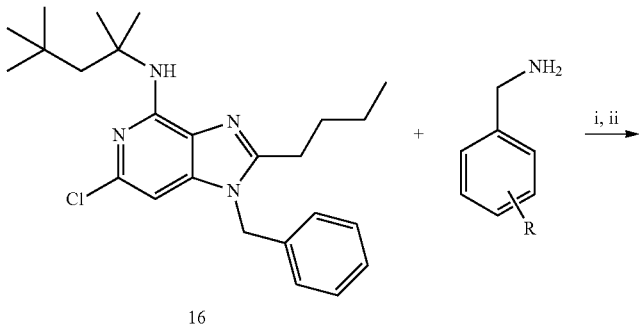

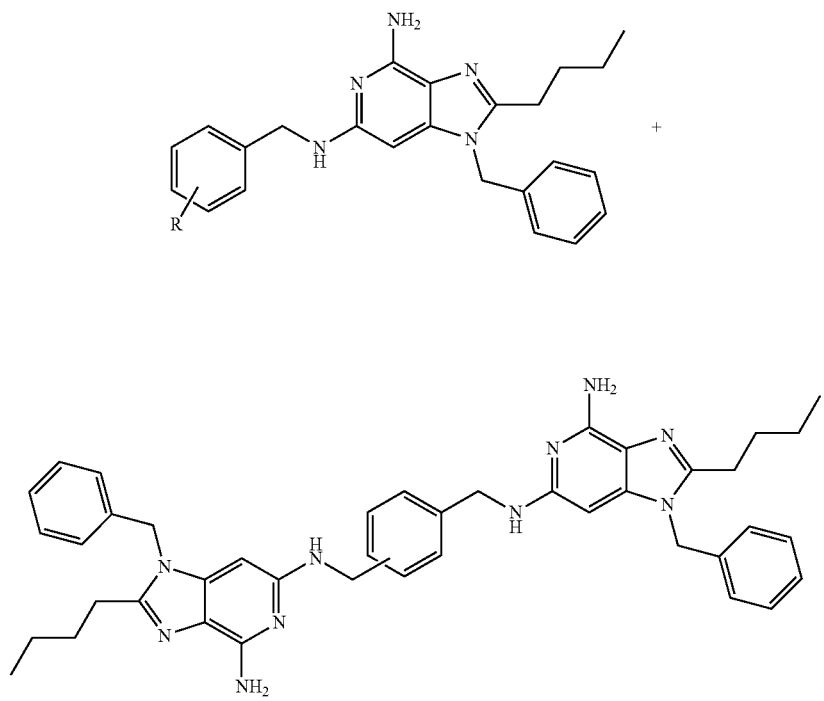

Compound 19q; R = m-CH$_2$NH$_2$
Compound 19r is p-dimer through benzene
Compound 19s is m-dimer through benzene
(i) Pd$_2$(dba)$_3$, DavePhos, KOtBu, dioxane; (ii) HCl.

For the C6-substituted compounds 23a-j (Scheme 6), mediocre yields were observed in pilot Suzuki coupling reactions with the advanced intermediate compound 16. Synthesis therefore exploited the electron-withdrawing resonance effect of the 3-nitro group in compound 14. As expected, the classical Suzuki reaction on intermediate compound 14 using various aliphatic and aromatic boronic acids/boronate esters resulted in the intermediates compounds 20a-j (Scheme 6), which were further derivatized to obtain the desired C$^6$ alkyl/aryl substituted imidazopyridines compounds 23a-j.

Scheme 6 reagents:

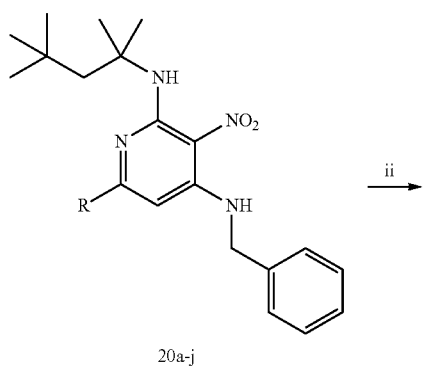

14

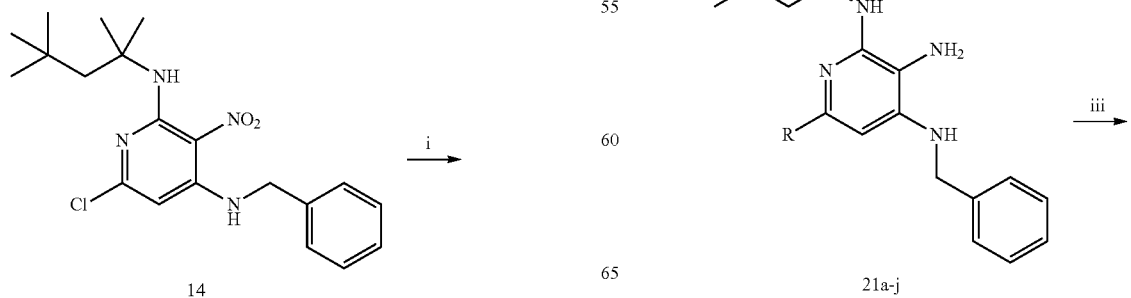

20a-j 21a-j

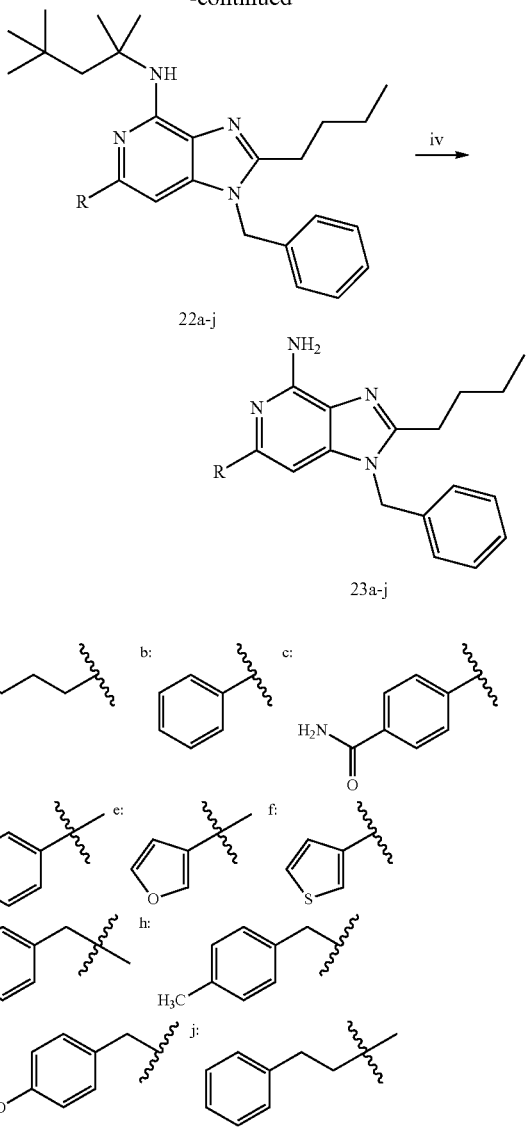

(i) For compounds 20a-f and compound 20j, R-Boronic acid, Pd(dppf)Cl₂, Cs₂CO₃, dioxane; For compound 20c, 4-Cyanopheny boronic acid, Pd(dppf)Cl₂, Cs₂CO₃, dioxane; For compounds 20g-i, R-Boronic acid pinacol ester, Pd(dppf)Cl₂, Cs₂CO₃, dioxane; (ii) Zn, HCOONH₄, MeOH; (iii) a. C₄H₉COCl, NEt₃, THF; b. NaOH, EtOH; (iv) HCl.

The 6-chloro imidazopyridine, compound 17 (Scheme 4) was inactive (Table 1). Buchwald-Hartwig-derived 7.6-substituted analogues compounds 19a-q, however, showed a distinctive SAR. Compound 19a with a free NH₂ at C⁶, obtained by coupling the tert-octylamine and subsequent N-dealkylation with HCl (Scheme 4, Table 1) displayed TLR7-specific agonism with a potency comparable to that of the parent C⁶-unsubstituted compound 5.

Modest gains in potency were obtained in analogues with short aliphatic substituents with N⁶-butyl (compound 19b) and N⁶-cyclohexylmethyl (compound 19d), but potency diminished in the N⁶-heptyl analogue (compound 19c). The N⁶-phenyl-substituted compound 19e was marginally weaker than compound 5; however, the potency of the N⁶-benzyl analogue 19f was ~7.6 times that of compound 5 (Table 1, FIG. 1), triggering a detailed SAR investigation on various aryl substituents at N⁶. Both steric and electronic effects appear to play a role in governing TLR7-agonistic potency, since the biphenylmethyl-substituted compound 19o was active, whereas the naphthylmethyl analogue 19n was quiescent; to a first approximation, electron-rich N⁶ substituents appear to be preferred, with the methoxybenzyl derivatives (compound 19g and compound 19h) and the pyridinylmethyl compounds (compound 19l and compound 19m) being marginally more active than the trifluoromethyl-(compound 19i) or chloro-(compound 19j) substituted analogues. Compounds 19p and 19q were also active in primary screens, with EC₅₀ values of 0.26 and 0.37 μM, respectively (Table 1). In the C⁶-alkyl or -aryl analogues (Scheme 6), the SAR appeared more stringent. Whereas the C⁶-butyl compound 23a was more active than compound 5, direct aryl-aryl connections at C6 (compounds 23b-f) abrogated activity, but TLR7 agonistic properties were restored in the 6-benzyl (compound 23g) and 6-phenethyl analogues (compound 23j). Taken together with activity data of compounds of the compounds 19 series, it was surmised that rotational constraints about the C⁶-aryl groups may hinder TLR7 occupancy. Unlike TLR2, TLR3, TLR4, and TLR5 for which crystal structures are available as complexes with their cognate ligands, a detailed structural characterization of the mode of binding of TLR7 ligands is not yet available to guide structure-based design of small molecule agonists of TLR7, necessitating classical SAR approaches to refine successive iterations of ligand design.

Figure 2:
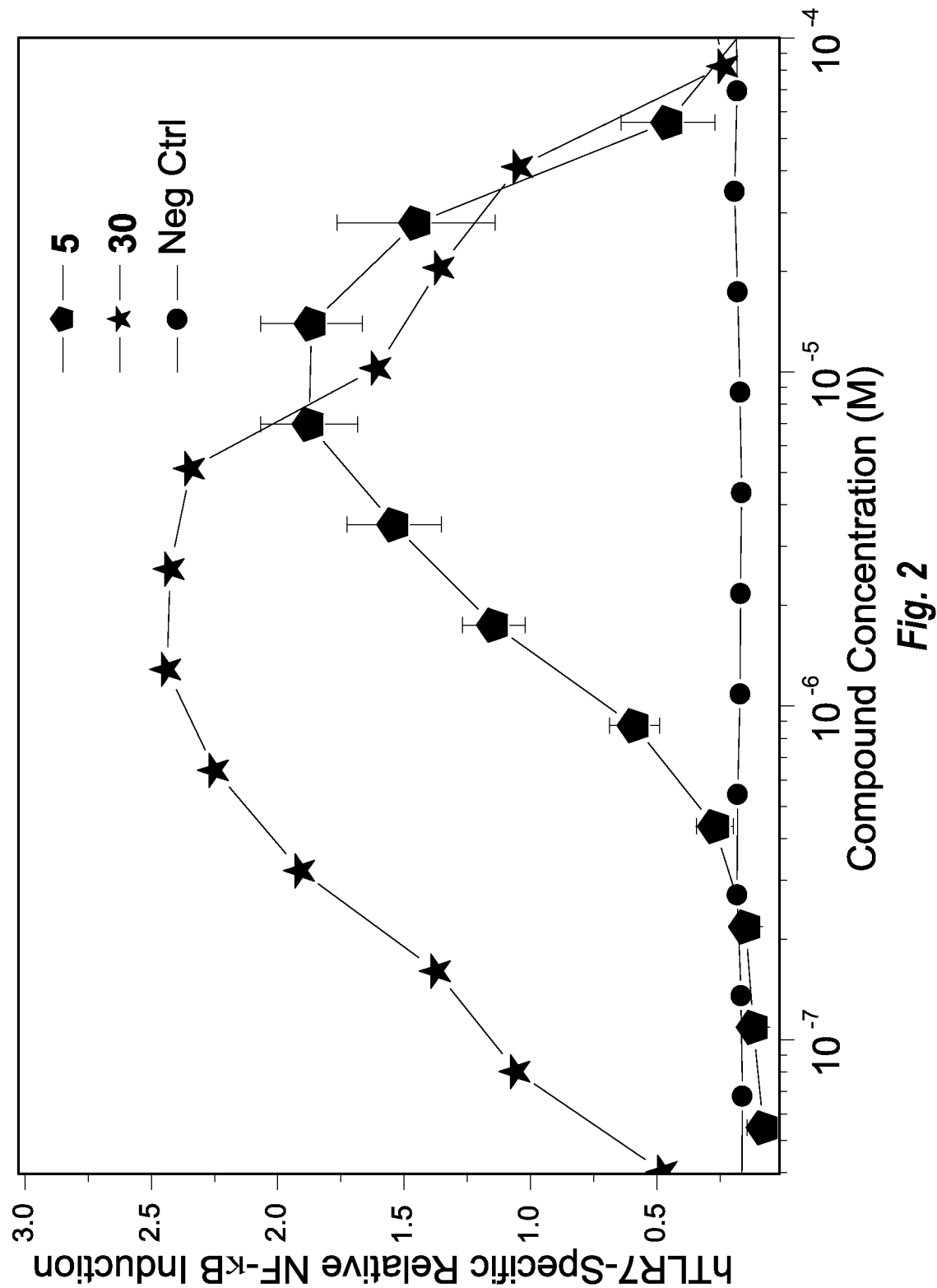
FIG. 2 includes a graph that shows dose-response profiles of TLR7 agonistic activity of compounds 5 and 30. Data points represent means and standard deviations on quadruplicates.
Figure 3A:
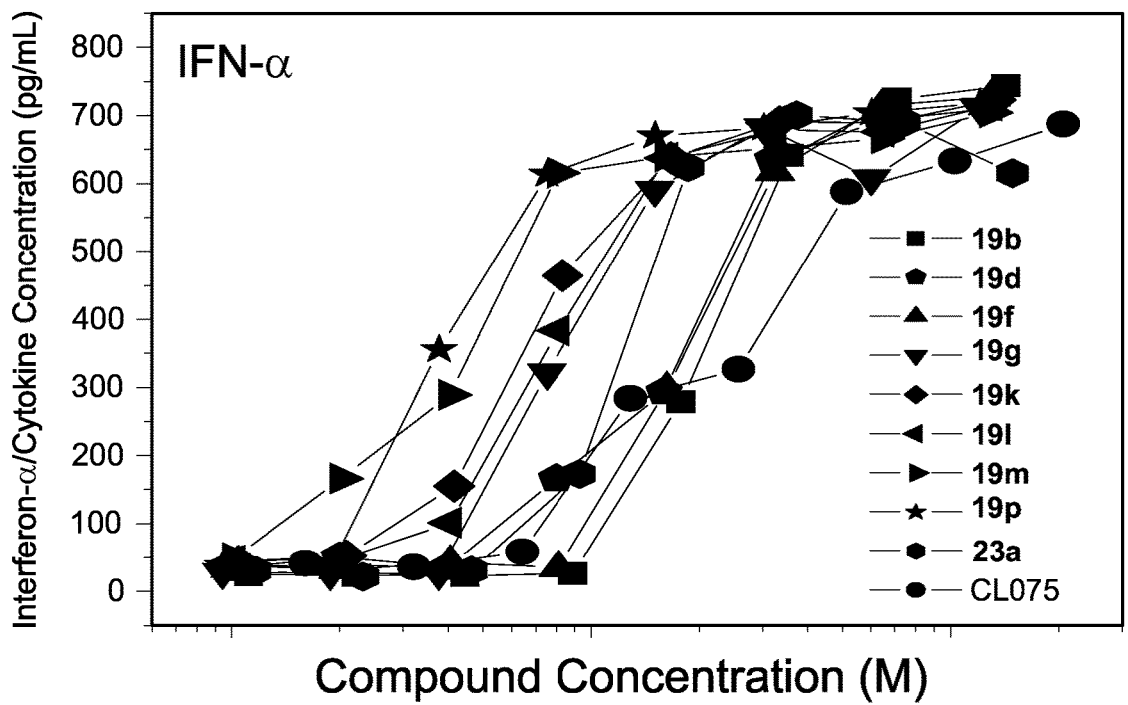
FIGS. 3A-3D include graphs that show dose-response profiles of Type I interferon (IFN-α) and proinflammatory cytokine (IL-8, IL-1β, and TNF-α) induction by selected imidazopyridine (and reference) compounds. Representative data from three independent experiments are presented.
Figure 3B:
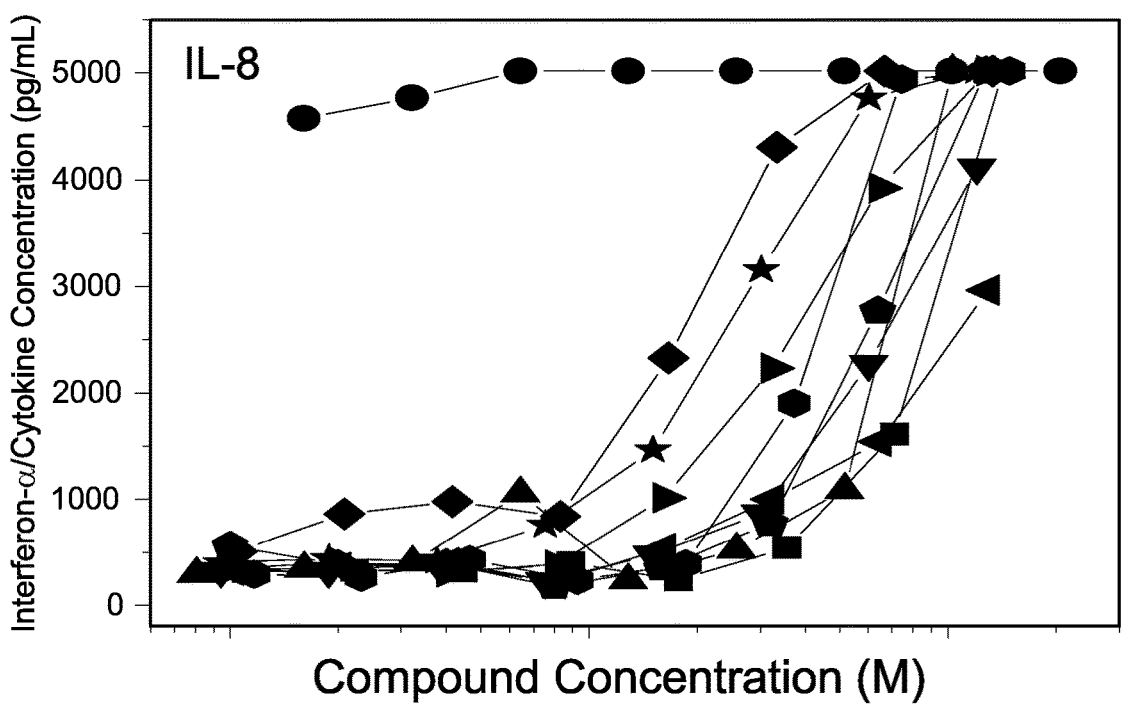
Figure 3C:
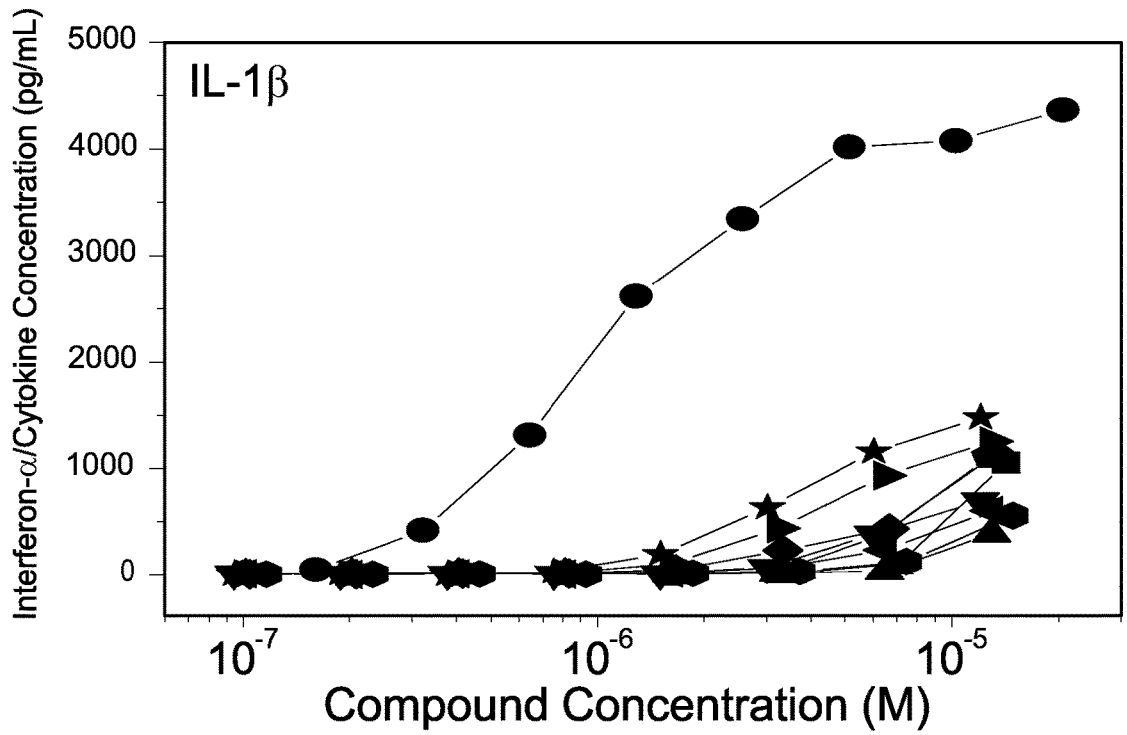
Figure 3D:
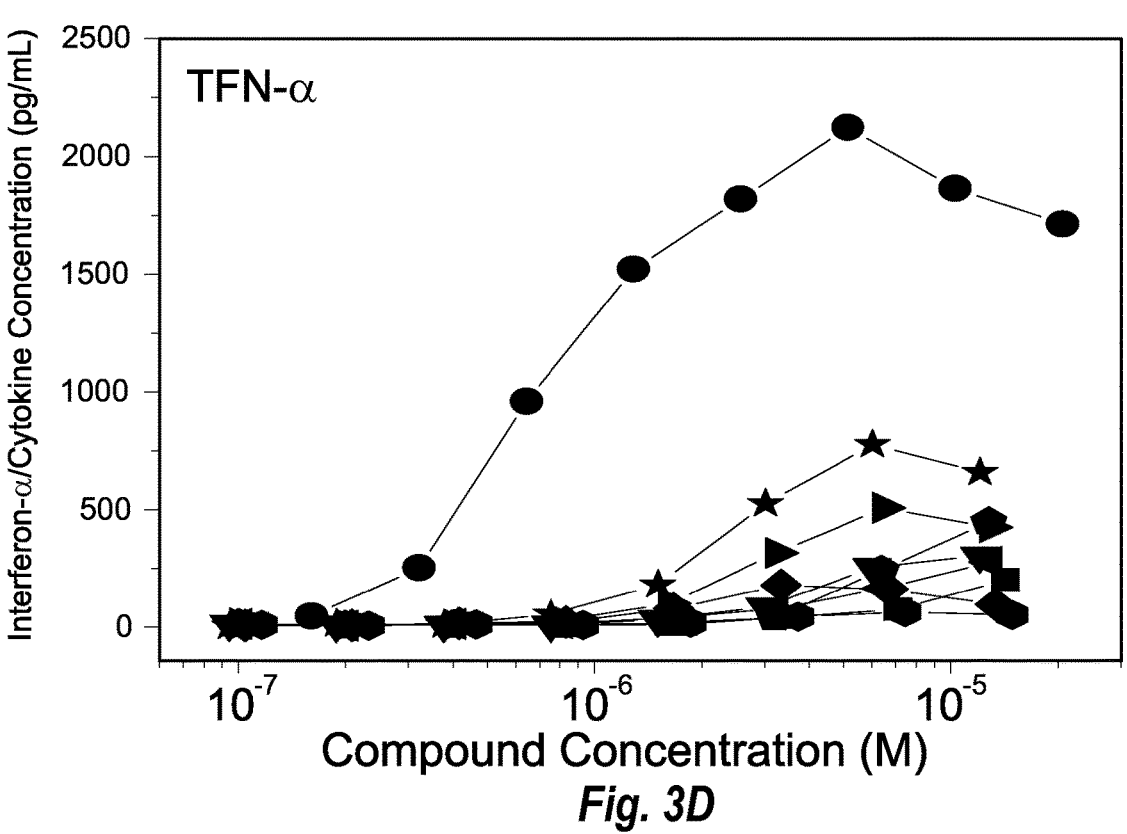

The benzologue compound 30 was synthesized as shown in Scheme 7. It showed substantial improvements in potency over the parent imidazopyridine compound 5 (FIG. 2, Table 1), but the two most potent compounds in the entire series as adjudged by primary screens were the N⁶-(4-methoxybenzyl) and N⁶-(furan-2-ylmethyl) analogues (compound 19g and compound 19k, respectively), both of which were approximately twenty-fold more potent than compound 5 (FIG. 1, Table 1).

Scheme 7 reagents:

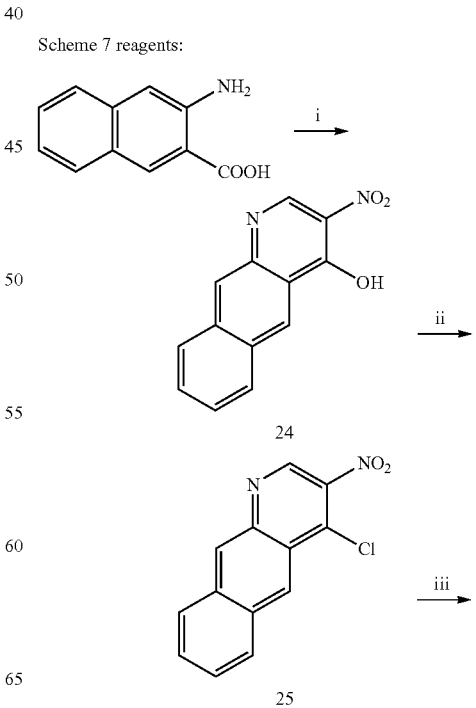

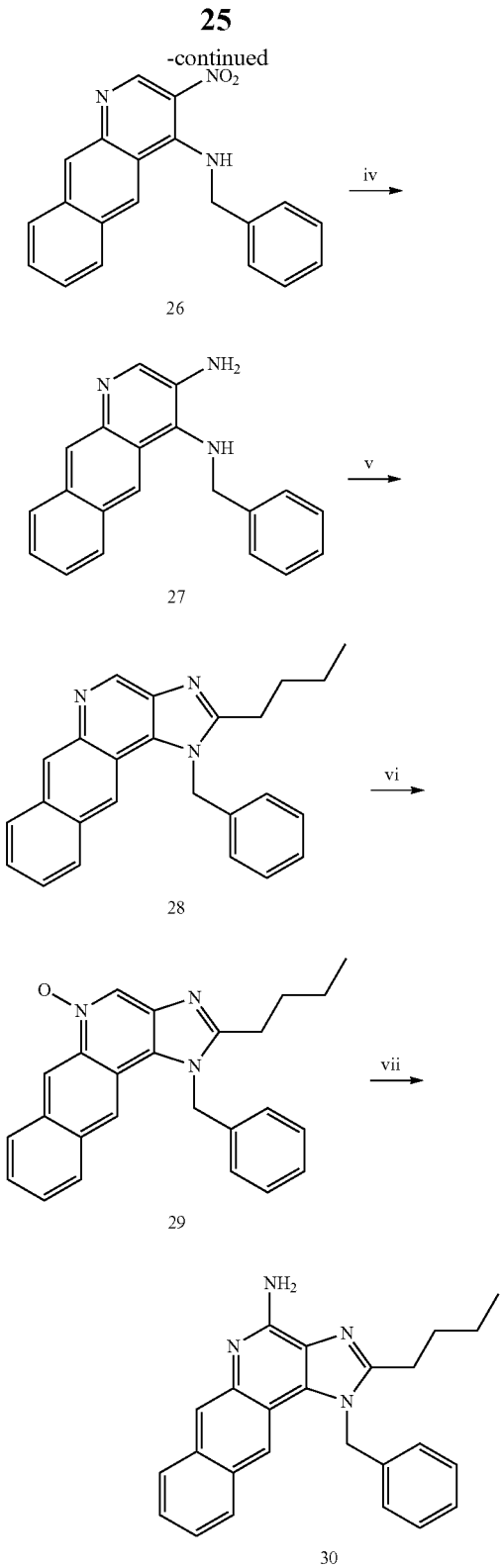

(i) a. HCl, HON=CHCH₂NO₂, H₂O; b. (CH₃CO)₂O, CH₃COOK; (ii) POCl₃; (iii) BnNH₂, NEt₃, CH₂Cl₂; (iv) Zn, HCOONH₄, MeOH; (v) a. C₄H₉COCl, NEt₃, THF; b. NaOH, EtOH; (vi) mCPBA, CH₂Cl₂, CHCl₃, MeOH; (vii) a. Benzoyl isocyanate, CH₂Cl₂; b. NaOMe, MeOH.

Nine of the most active compounds (e.g., compounds 19b, 19d, 19f-g, 19k-m, 19p and 23a) were selected for evaluation in secondary screens using IFN-α and cytokine release in human PBMCs. Reference compounds included imiquimod, a known TLR7 agonist, as well as CL075 (2-propylthiazolo[4,5-c]quinolin-4-amine), a predominantly TLR8-active agonist with an $EC_{50}$ of 1.32 µM in hTLR8 assays. See the provisional applications for additional information. Given that the imidazopyridine compounds are pure TLR7 agonists, it was expected to find prominent IFN-α induction, and this was indeed the case, with compounds 19p, 19m and 19k being the most potent (e.g., $EC_{50}$: 0.3 µM, 0.4 µM and 0.7 µM, respectively; FIG. 3A-3D). CL075 was among the least potent in IFN-α induction ($EC_{50}$: 2.6 µM; FIG. 3A-3D), and as expected for a TLR8 agonist, CL075 was dramatically more active in inducing proinflammatory cytokines such as TNF-α, IL-1β, and IL-8 (FIG. 3A-3D). There was a slight discrepancy between rank-order potency in primary screens (19k=19g>19f>19p; FIG. 1, Table 1) vis-à-vis IFN-α-inducing potency in human PBMCs (19p=19m>19k; FIG. 3A-3D), and it is surmised that analogues with more basic $C^6$ substituents may allow for higher endolysosomal partitioning. The dose-response profiles show characteristic biphasic responses (dose-dependent activation, followed by apparent suppression) as previously observed in several chemotypes. It was verified that the apparent suppression was not due to cytotoxicity using LDH release and mitochondrial redox-based assays.

Figure 4A:
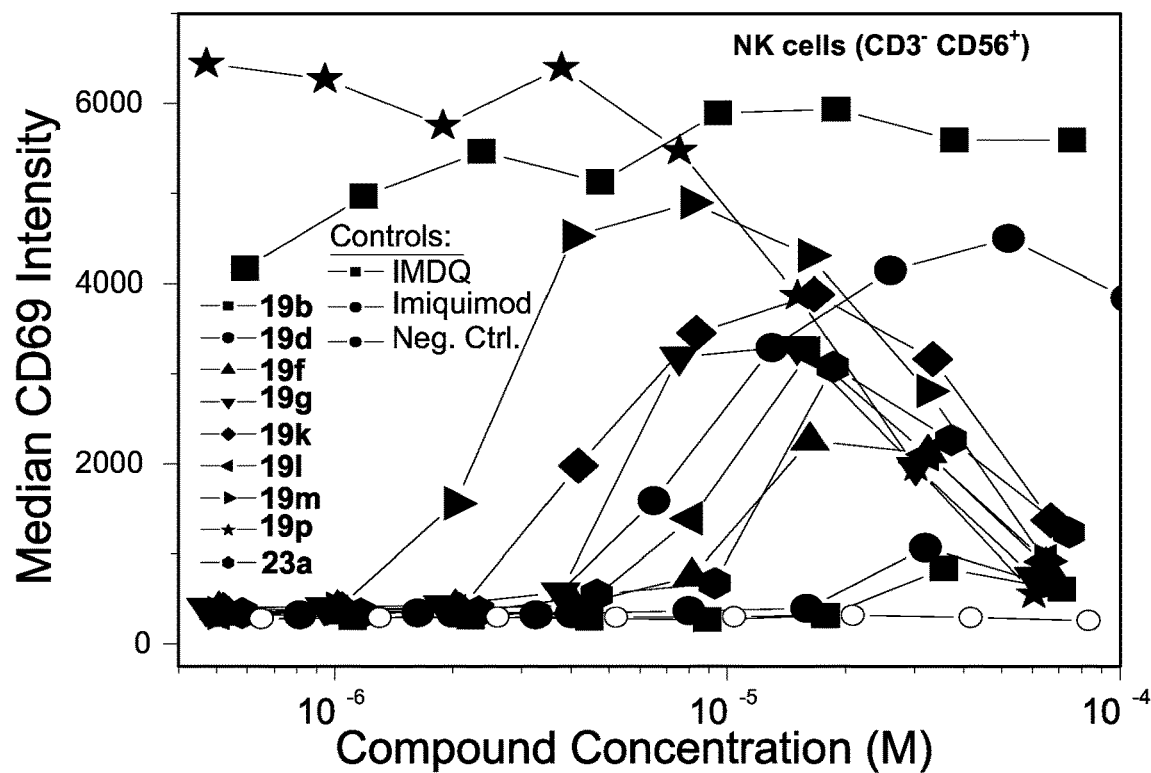
FIGS. 4A-4C includes graphs that show CD69 upregulation in human natural killer (NK), cytokine-induced killer (CIK) and nominal B lymphocytes by select imidazopyridine (and reference) compounds.
Figure 4B:
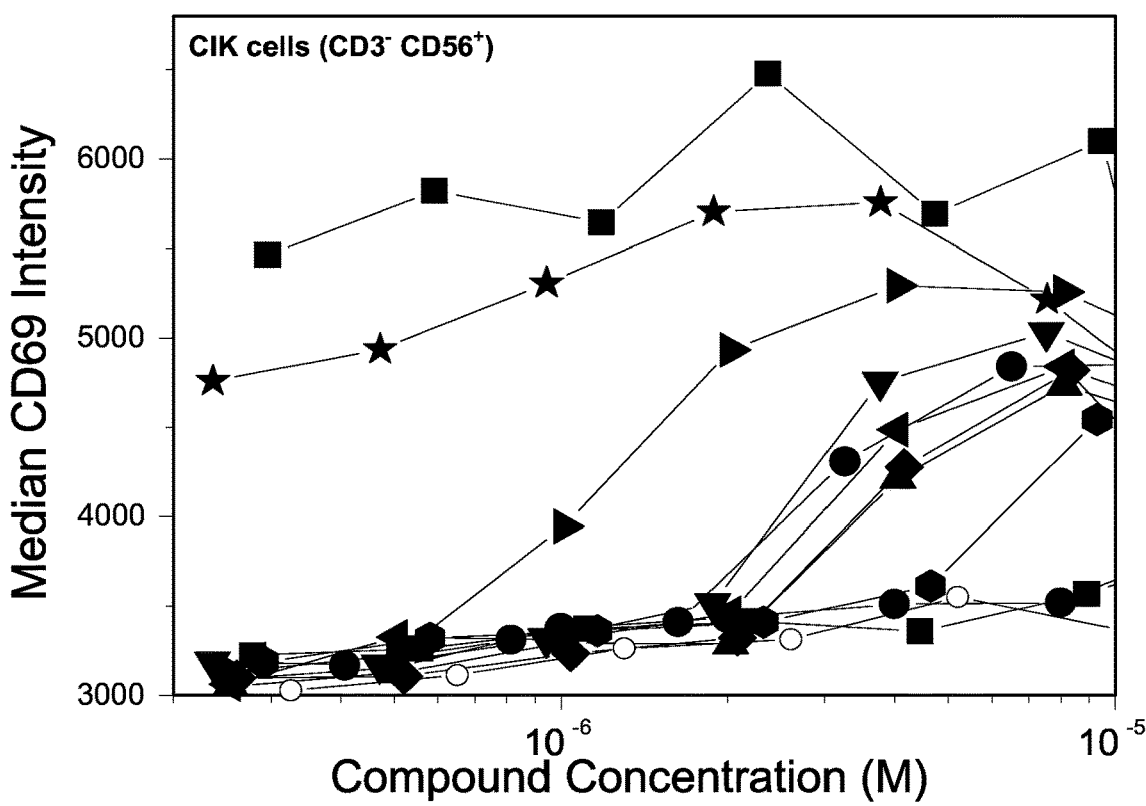
Figure 4C:
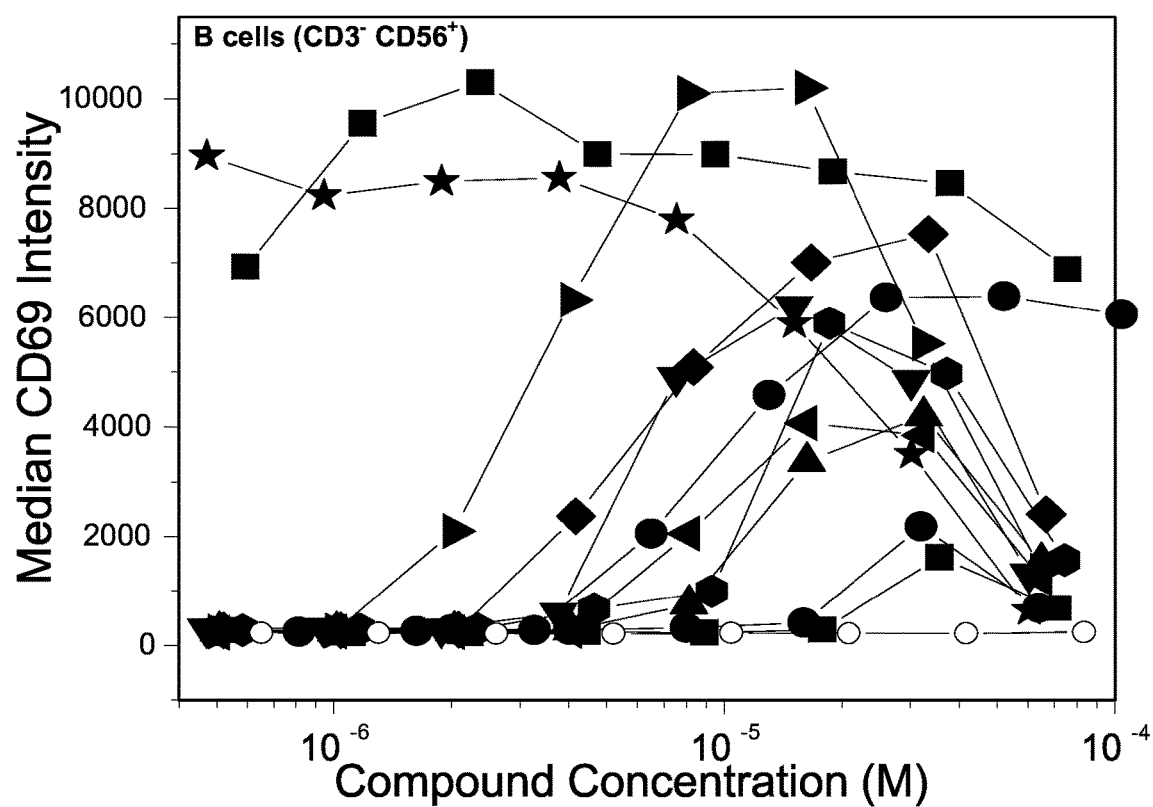

It has been shown that TLR7 agonists were extraordinarily immunostimulatory, stimulating virtually all subsets of lymphocytes (e.g., assessed by quantifying CD69 expression), and yet without inducing dominant proinflammatory cytokine responses. It was observed that there was considerable dissociation between Type I IFN induction on the one hand (FIG. 3A-3D), and CD69 upregulation in lymphocytic subsets on the other (FIG. 4A-4C). Whereas the subset of active compounds induced IFN-α with similar potencies (e.g., $EC_{50}$ values between 0.3-2 µM; FIG. 3A-3D), pronounced differences were observed in CD69 expression in natural killer, cytokine-induced killer and B lymphocytic subsets with compound 19p being as active as the reference TLR7 agonist IMDQ, and compound 19d showing virtually no activity (FIG. 4A-4C). The potential advantages of strong Type I IFN inducers as candidate vaccine adjuvants have been discussed earlier. Such compounds, especially in conjunction with attenuated proinflammatory cytokines, are expected to be potently adjuvantic without inducing prominent local or systemic inflammation. As mentioned earlier, the prominent Type I IFN inducing abilities of the imidazopyridines may also find utility as an alternative therapeutic strategy to address disease states wherein systemic IFN-α is of proven benefit. A clear delineation of structural features that confer TLR specificity not only charts a rational course for the development of effective, yet safe vaccine adjuvants, but also provides tools to understand innate immune function in greater detail.

Figure 5B:
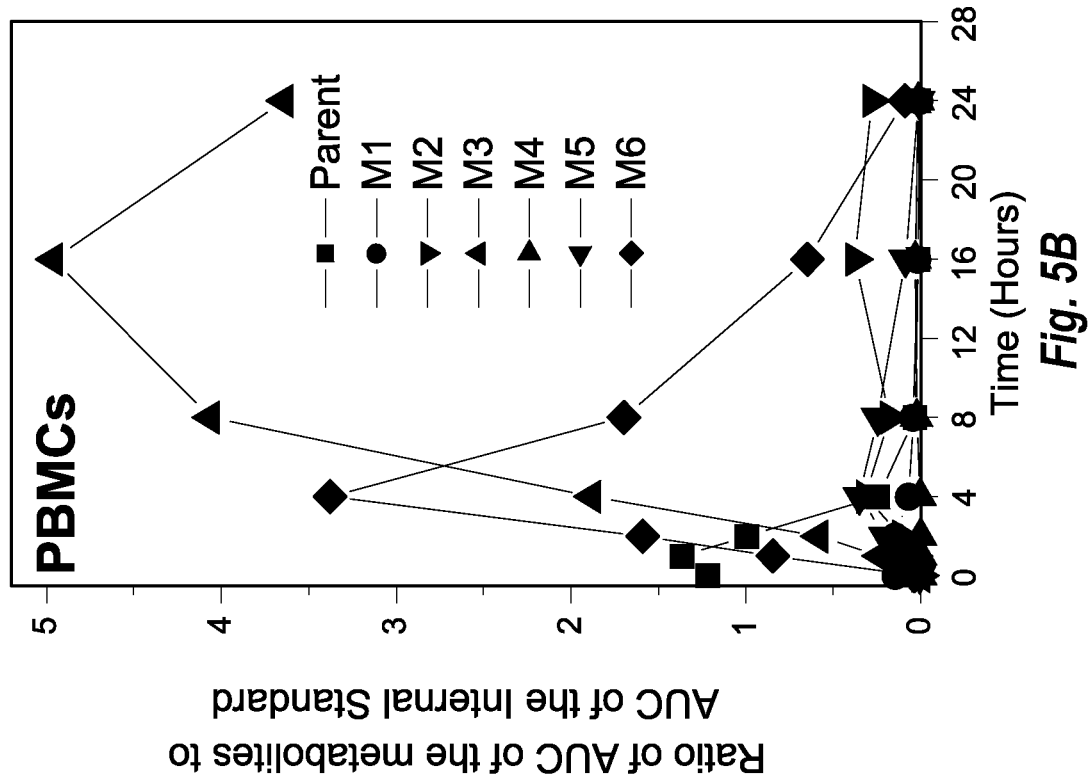
FIG. 5B includes a graph that shows 6 major metabolites of 19p identified by LC-MS/MS.
Figure 5A:
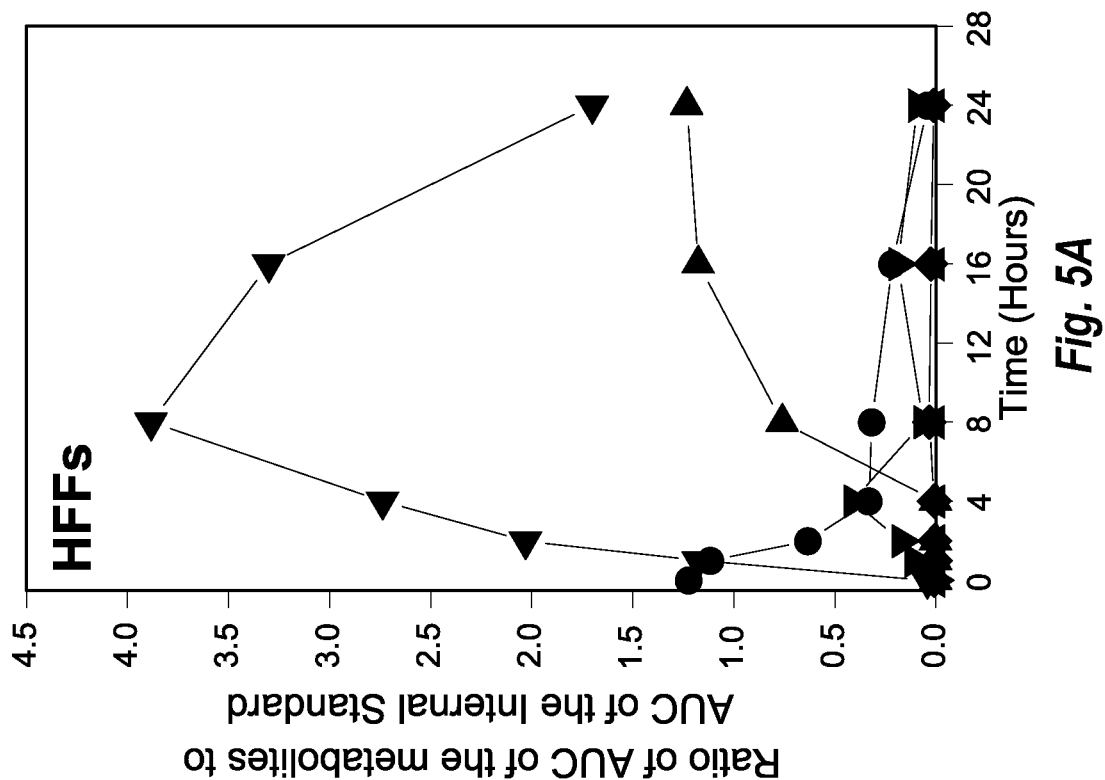
FIG. 5A includes a graph that shows compound 19p was rapidly metabolized in both HFFs and PBMCs. The parent was nearly undetectable by LC-MS at 1 hour in HFFs and was depleted in PBMCs by 8 hours.

The compound 19p was screened in non-hepatic cells, including human foreskin fibroblasts (HFFs) and peripheral blood mononuclear cells (PBMCs) to determine the metabolic stability of the compounds in a high throughput manner using microdialysis and LC-MS/MS. Compound 19p was rapidly metabolized in both HFFs and PBMCs with half-lives of <1 hour and 3 hours, respectively (summarized in FIGS. 5A-5B and Table A).

TABLE A

| Metabolites | Retention Time (min) | Experimental Accurate m/z | Theoretical Accurate m/z | Proposed Biotransformation |
|---|---|---|---|---|
| 19p | 7.95 | 415.2613 | 415.2605 | Parent Compound |
| M1 | 7.88 | 429.2411 | 429.2397 | Oxygenation |
| M2 | 10.52 | 430.2283 | 430.2238 | Oxygenation + Oxidative Deamination + Reduction of Aldehyde to Alcohol |
| M3 | 10.55 | 416.2487 | 416.2445 | Oxidative Deamination + Reduction of Aldehyde to Alcohol |
| M4 | 10.8 | 444.2077 | 444.2030 | Oxidative Deamination + Oxidation of Aldehyde to Carboxylic Acid |
| M5 | 11.55 | 428.2126 | 428.2081 | Oxygenation + Oxidative Deamination |
| M6 | 11.45 | 414.2332 | 414.2288 | Oxidative Deamination |

TABLE 1

$EC_{50}$ values of compounds in human TLR7-specific reporter gene assay.

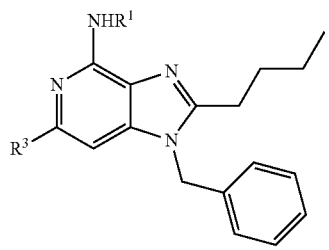

| Compound Number | $R^1$ | $R^3$ | hTLR7-agonistic Activity (μM) |
|---|---|---|---|
| 5 | H | H | 1.57 |
| 6a | $COCH_3$ | H | Inactive[a] |
| 6b | $COC_3H_7$ | H | Inactive |
| 11a | $C_4H_9$ | H | Inactive |
| 11b | $CH_2C_6H_5$ | H | Inactive |
| 17 | H | Cl | Inactive |
| 19a | H | $NH_2$ | 1.25 |
| 19b | H | $NHC_4H_9$ | 0.34 |
| 19c | H | $NHC_7H_{15}$ | 0.76 |
| 19d | H | cyclohexyl-CH$_2$-NH | 0.32 |
| 19e | H | $NHC_6H_5$ | 1.72 |
| 19f | H | $NHCH_2C_6H_5$ | 0.21 |
| 19g | H | 4-MeO-C$_6$H$_4$-CH$_2$-NH | 0.075 |
| 19h | H | 3-MeO-C$_6$H$_4$-CH$_2$-NH | 0.61 |
| 19i | H | 4-CF$_3$-C$_6$H$_4$-CH$_2$-NH | 1.04 |
| 19j | H | 4-Cl-C$_6$H$_4$-CH$_2$-NH | 0.64 |

TABLE 1-continued
EC$_{50}$ values of compounds in human TLR7-specific reporter gene assay.
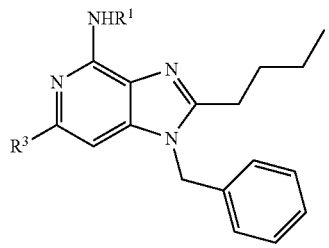
| Compound Number | R$^1$ | R$^3$ | hTLR7-agonistic Activity (μM) |
|---|---|---|---|
| 19k | H | furan-2-ylmethyl-NH | 0.075 |
| 19l | H | pyridin-4-ylmethyl-NH | 0.25 |
| 19m | H | pyridin-3-ylmethyl-NH | 0.25 |
| 19n | H | naphthalen-1-ylmethyl-NH | Inactive |
| 19o | H | biphenyl-4-ylmethyl-NH | 1.09 |
| 19p | H | 4-(aminomethyl)benzyl-NH | 0.26 |
| 19q | H | 3-(aminomethyl)benzyl-NH | 0.37 |
| 19r | H | (see structure) | 1.08 |

TABLE 1-continued
EC$_{50}$ values of compounds in human TLR7-specific reporter gene assay.
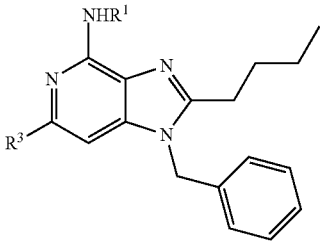
| Compound Number | R$^1$ | R$^3$ | hTLR7-agonistic Activity (μM) |
|---|---|---|---|
| 19s | H | 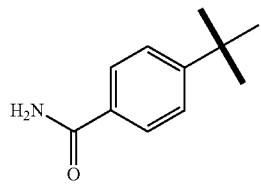 | Inactive |
| 23a | H | C$_4$H$_9$ | 0.28 |
| 23b | H | C$_6$H$_5$ | Inactive |
| 23c | H | 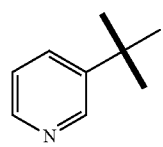 | Inactive |
| 23d | H | 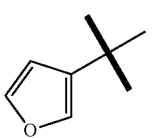 | Inactive |
| 23e | H | 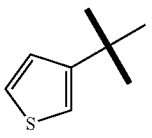 | Inactive |
| 23f | H | 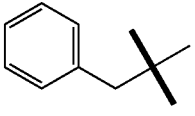 | Inactive |
| 23g | H | 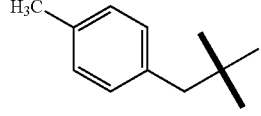 | 0.28 |
| 23h | H |  | 1.80 |

TABLE 1-continued

EC$_{50}$ values of compounds in human TLR7-specific reporter gene assay.

[Structure: 4-amino-imidazo[4,5-c]pyridine core with NHR$^1$ at 4-position, butyl at 2-position, benzyl on N1, R$^3$ at 6-position]

| Compound Number | R$^1$ | R$^3$ | hTLR7-agonistic Activity (μM) |
|---|---|---|---|
| 23i | H | 4-(F$_3$CO)-benzyl-C(CH$_3$)$_2$- | Inactive$^a$ |
| 23j | H | phenethyl-C(CH$_3$)$_2$- | 0.57 |
| 30 | | Benzologue (see structure in Scheme 7) | 0.22 |

$^a$Inactive: no activity was detected up to a concentration of 500 μg/mL

In view of the foregoing, the compounds of Table 1 can be used as adjuvants with vaccine agent. The vaccine agent is the substance used for the vaccination.

TLR

Toll-like receptor (TLR)-8 agonists strongly induce the production of T helper 1-polarizing cytokines, and may therefore serve as promising candidate vaccine adjuvants, especially for the very young and the elderly. Earlier structure-based ligand design led to the identification of 3-pentyl-quinoline-2-amine as a novel, human TLR8-specific agonist. Comprehensive structure-activity relationships in ring-contracted 1-alkyl-1H-benzimidazol-2-amines were undertaken, and the best-in-class compound, 4-methyl-1-pentyl-1H-benzo[d]imidazol-2-amine, was found to be a pure TLR8 agonist, evoking strong proinflammatory cytokine and Type II interferon responses in human PBMCs, with no attendant CD69 upregulation in natural lymphocytic subsets. The 1-alkyl-1H-benzimidazol-2-amines represent a novel, alternate chemotype with pure TLR8-agonistic activities, and will likely prove useful not only in understanding TLR8 signaling, but also perhaps as a candidate vaccine adjuvant.

It was found that small molecule agonists of TLR8 can be used as vaccine adjuvants. Some of the compounds of the invention (e.g., designated with compound identifier "A#") can pure TLR8 agonists with no detectable TLR7 activity. Accordingly, some compounds of the invention (e.g., designated with compound identifier without the leading "A") can be pure TLR7 agonists with no detectable TLR8 activity. It was found that the strongly Th1-biasing TLR8 agonists could be useful as candidate vaccine adjuvants for the newborn. Maternal immunoglobulins acquired by passive transplacental passage confer protection to the neonate for the first few weeks of life; thereafter, the newborn is susceptible to a wide range of pathogens until early infancy. The very young do not mount adequate adaptive immune responses and, consequently, even highly effective vaccines that confer excellent protection in adults may fail to elicit strong immune responses in them. The neonatal immunophenotype is characterized by decreased production of both type I and type II interferons, as well as Th1-biasing cytokines such as TNF-α, IL-12, IL-18, IL-23, the preferential induction of memory B lymphocytes rather than immunoglobulin-secreting plasma cells, as well as a pronounced T-helper type 2 (Th2) skewing of T-cell responses. TLR8 agonists induce the production of IL-12, IL-18 and IFN-γ, and may therefore be of value in developing vaccines for the neonate.

The theory that TLR8 agonists can be used as adjuvants has been sustained also by observations of impaired TLR signaling contributing to immune senescence in aging. In particular, substantial decreases in TNF-α, IL-6, and/or IL-12p40 production have been documented in myeloid dendritic cells isolated from older individuals in response to TLR8 engagement, reflecting parallels in immune ontogeny of TLR-driven cytokine responses between the very young and the aged.

A high-resolution (1.8 Å) structure of human TLR8 co-crystallized with a pure TLR8-agonistic lead compound (e.g., C2-butyl-furo[2,3-c]quinoline) suggested that the furan ring was dispensable, and led to the identification of 3-pentyl-quinoline-2-amine as a novel, structurally simple, and highly potent human TLR8-specific agonist. It has been found that structure-activity relationships in the ring-contracted 1-alkyl-1H-benzimidazol-2-amines can lead to TLR8 agonists. The best-in-class compound of this novel chemotype, 4-methyl-1-pentyl-1H-benzo[d]imidazol-2-amine, was found to retain a pure TLR8 agonistic activity profile.

A ring-contracted 2-amino-3-alkylindole analogue compound A4, accessed via sequential C-alkylation of commercially available 2-nitrophenylacetonitrile, reduction of the 2-nitro group, and Brønsted acid-promoted, microwave-assisted intramolecular cyclization (Scheme A1). The hydrochloride salt of compound A4 was isolated and found to be inactive; its free-base, however, was exceedingly unstable, leading to the rapid formation of the over-oxidized 3-ol derivative compound A5, presumably via autoxidation (Scheme A1), which was also inactive in primary screens.

Scheme A1 reagents and conditions:

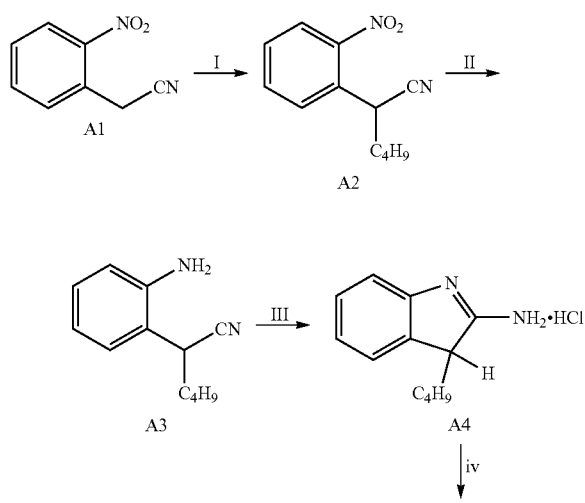

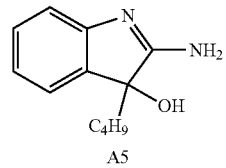

(i) $C_4H_9I$, $K_2CO_3$, DMSO, 3 h; (ii) $H_2$, Pt/C, 30 psi, EtOAc, 3 h; (iii) HCl, dioxane, MW 400W, 100° C., 20 min; (iv) $Et_3N$, MeOH, 3 h.

Figure 6:
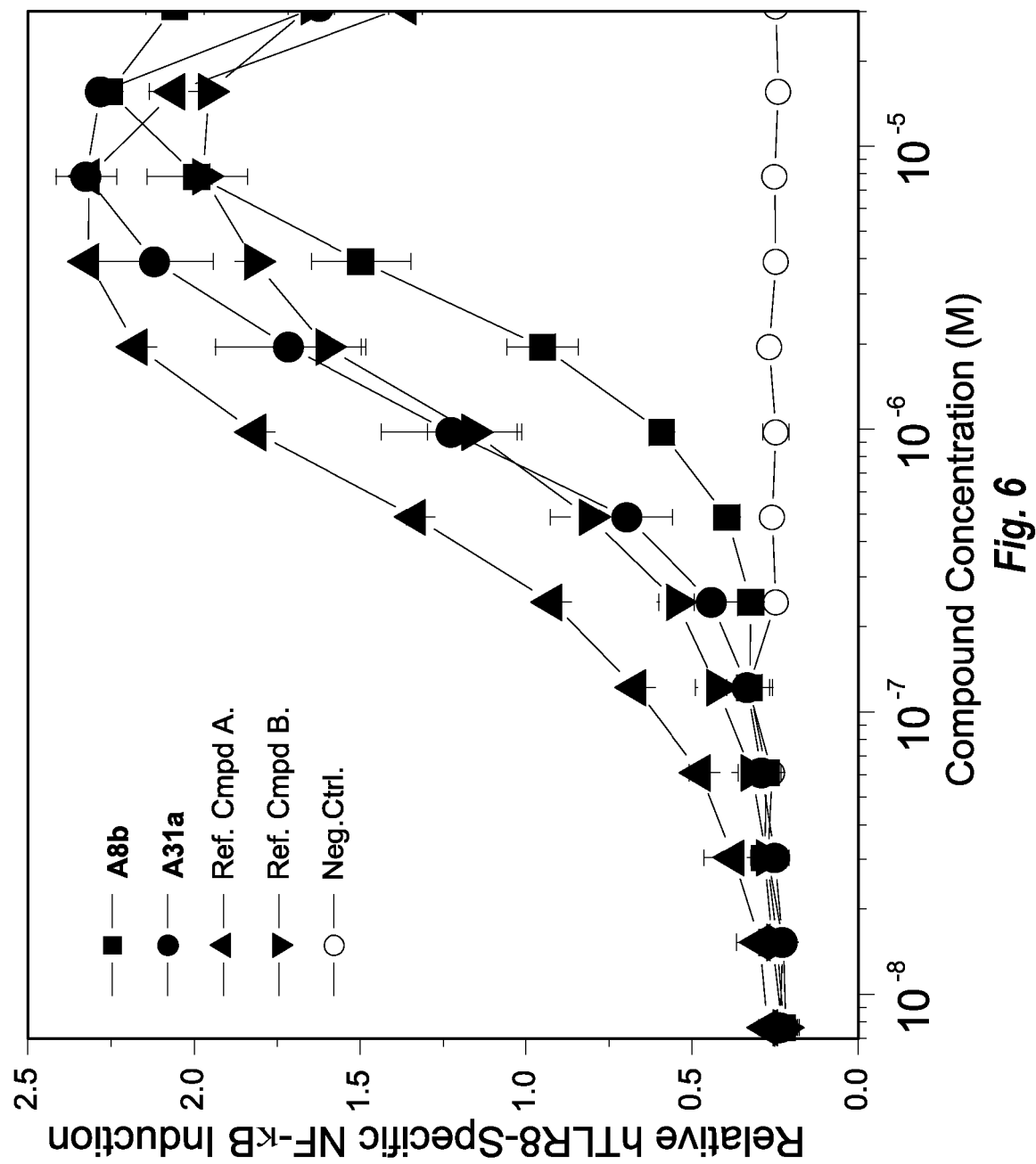
FIG. 6 includes a graph that shows dose-response profiles by select 1-alkyl-1H-benzimidazol-2-amines in reporter gene cells expressing human TLR8. Error bars represent standard deviations obtained on quadruplicates. Reference compounds A and B (pure TLR8 agonists) are 3-pentyl-quinoline-2-amine and C2-butyl-furo[2,3-c]quinoline, respectively.

Stable analogues possessing structural scaffolds similar to the 2-aminoindole compound A4, were sought to be synthesized through investigations with 1-alkyl-2-aminobenzimidazole analogues (Scheme A2). The 2-aminobenzimidazole scaffold was conveniently accessed via the reaction of o-phenylenediamine with cyanogen bromide (CNBr). The N1 position could be selectively derivatized (Scheme A2), furnishing analogues. In a focused SAR assessment of these analogues, a clear dependence of substituent chain length at N1 was noted, consistent with previous observations on other chemotypes, with the optimal analogue being compound A8b (N1-pentyl; $EC_{50}$=3.23 µM; FIG. 6). Analogues with benzyl (compound A8d) and 3-aminomethylbenzyl (compound A8f) substituents at N1 were obtained, for these substituents on the imidazoquinoline scaffold had yielded high-potency pure TLR7 and mixed TLR8/7 agonists, respectively. It was found that neither compound A8d nor compound A8f were active; substitution of the N1-pentyl group with butoxycarbonyl group (compound A9), or acylation of the N2 amine (compound A10) also completely abrogated activity, suggestive of stringent structural requirements for activity, and demonstrating that both the free amine at C2 and the N1 pentyl substituent are important for TLR8-agonistic activity.

Scheme A2 reagents and conditions:

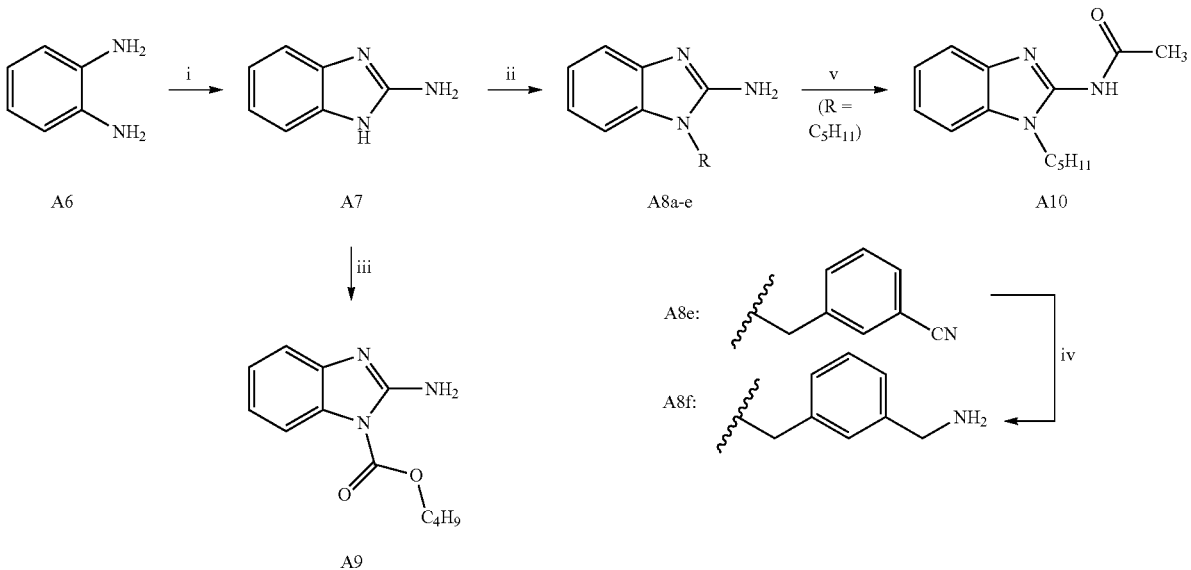

Compound A8a: R = $C_4H_9$
Compound A8b: R = $C_5H_{11}$
Compound A8c: R = $C_6H_{13}$
Compound A8d: R = Bn
(i) CNBr, MeOH:$H_2O$ (1:1), 60° C., 3 h; (ii) RI, KOH, acetone, 60° C., 3 h; (iii) $C_4H_9OCOCl$, THF, 25° C., 3 h; (iv) $LiAlH_4$, THF, 75° C., 5 h; (v) $CH_3COCl$, pyridine, 25° C., 3 h.

Modifications on the benzimidazole were prepared to synthesize all possible regioisomeric benzologues of compound A8b (Scheme A3). The naphtho[2,3-d]imidazole analogue compound A13 was accessed readily via cyclization of the naphthalene-2,3-diamine with CNBr. The symmetry-related regioisomers compound A18 and compound A23 could, in principle, have been obtained from the rather expensive 1,2-diaminonaphthalene, followed by resolution of the regioisomers. But given the near-identical $R_f$ values (and retention times in analytical HPLC) of these two regioisomers, it was fortunate to have opted for an alternative route. Conversion to the nitromethoxynaphthols compound A15 and compound A20, which underwent facile nucleophilic substitution reactions with pentylamine, affording the desired regioisomers compound A18 and compound A23 in good yields (Scheme A3). Of the three different regioisomers, only compound A23 ($EC_{50}$=3.16 µM) showed near-identical activity to that of compound A8b (Table A1). These observations, taken together, also suggested that substitutions could be tolerated at C4 and C5, but not at C6 and C7, which were borne out as described below.

Scheme A3 reagents and conditions:

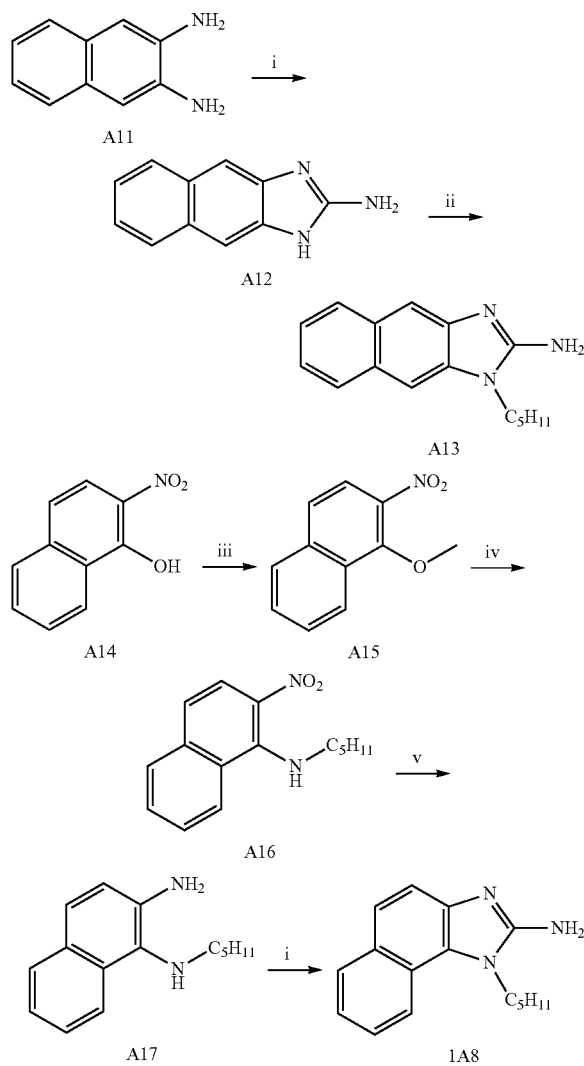

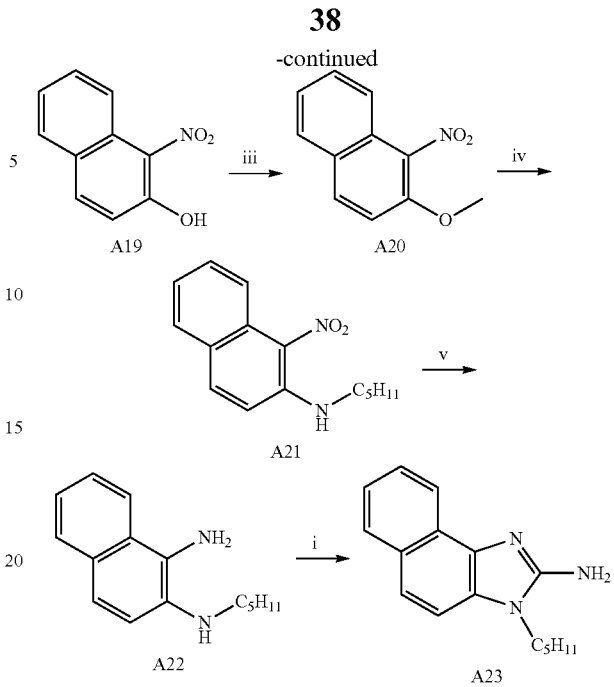

(i) CNBr, MeOH:H$_2$O (1:1), 60° C., 3 h; (ii) C$_5$H$_{11}$I, KOH, acetone, 60° C., 3 h; (iii) MeI, KOH, acetone, reflux, 12 h; (iv) C$_5$H$_{11}$NH$_2$, DMF, 60° C., 12 h; (v) H$_2$, Pt/C, 30 psi, EtOAc, 3 h.

Regioisomers of imidazopyridines (compounds A27a-d) were synthesized and studied for possible TLR7/8 activity, given that these analogues are congeneric to the imidazo[4,5-c]pyridines (Scheme A4). These analogues were synthesized via SNAr reactions of corresponding o-halonitropyridines with pentylamine, reduction of the nitro group, and final cyclization with CNBr (Scheme A4).

Scheme A4 reagents and conditions:

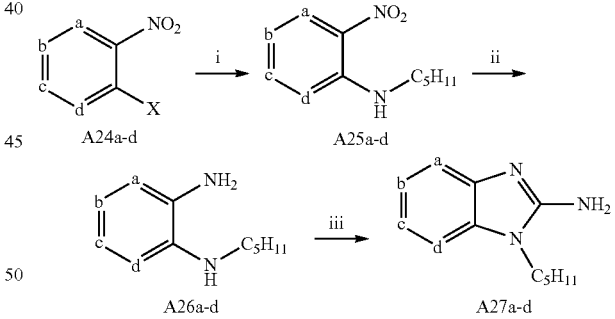

Compound A27a: b,c,d = CH; a = N
Compound A27b: a,c,d = CH; b = N
Compound A27c: a,b,d = CH; c = N
Compound A27d: a,b,c = CH; d = N
(i) C$_5$H$_{11}$NH$_2$, DIPEA, DMSO, 60° C., 6 h; (ii) H$_2$, Pt/C, 30 psi, EtOAc, 3 h; (iii) CNBr, MeOH:H$_2$O (1:1), 60° C., 3 h.

Methyl substituents at C4-C7 positions were performed (compounds A31a-A31d, Scheme A5) to ascertain steric effects of the benzimidazole ring, and their consequences on biological activity. Only compound A31a, with a C4-methyl group showed significantly more potent activity ($EC_{50}$=1.13 µM), relative to the parent compound A8b; the potency was comparable to that of C2-butyl-furo[2,3-c]quinoline, and marginally less than that of 3-pentyl-quinoline-2-amine (FIG. 6). Different electron-donating and -withdrawing substituents at C4 position were studied. The methoxy analogue compound A31e ($EC_{50}$=3.74 μM) showed comparable activity to that of compound A8b, but was less active than compound A31a (Table A1). Electron-withdrawing substitutions (compounds A31f-A31i) resulted in inactive compounds. Homologation of the methyl group at C4 to the ethyl-substituted analogue compound A31j (accomplished via Suzuki coupling of 3-bromo-2-nitro-N-pentylaniline with ethylboronic acid, and subsequent collaboration; Scheme A5) resulted in a slight reduction in TLR8-agonistic potency compared to compound A31a, alerting to the possibility that longer (or bulkier) substituents would not be favorable and, indeed, phenyl (compound A31l) benzyl (compound A31m), or benzyloxy (compound A35) substituents at C4 abrogated activity.

The 4-hydroxy analog compound A36 was prepared by Scheme A6. The electron-deficient 4-nitro analogue compound A39 (Scheme A7) was inactive, and analogues with electron-donating groups at C4 (compounds A31k, A36, A40; Schemes A5-A7) displayed attenuated potency relative to the 4-methyl compound A31a (Table A1).

Scheme A5 reagents and conditions:

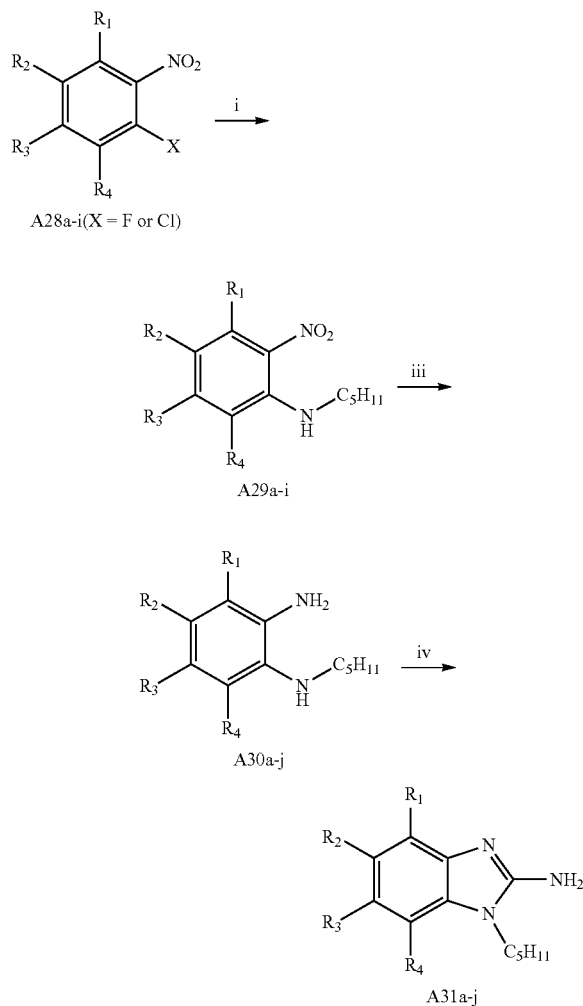

A31a: R2,R3,R4 = H, R1 = CH3
A31b: R1,R3,R4 = H, R2 = CH3
A31c: R1,R2,R4 = H, R3 = CH3
A31d: R1,R2,R3 = H, R4 = CH3
A31e: R2,R3,R4 = H, R1 = OCH3
A31f: R2,R3,R4 = H, R1 = F
A31g: R2,R3,R4 = H, R1 = Cl
A31h: R2,R3,R4 = H, R1 = CF3
A31i: R2,R3,R4 = H, R1 = Br
A31k: R2,R3,R4 = H, R1 = C6H5
A31l: R2,R3,R4 = H, R1 = CH2-C6H5
A31j: R2,R3,R4 = H, R1 = C2H5

(i) $C_5H_{11}NH_2$, DIPEA, DMSO, 60° C., 12 h; (ii) $C_2H_5$-B(OH)$_2$, $K_2CO_3$, Pd(dppf)Cl$_2$, 1,4-dioxane, 90° C., 12 h; (iii) $H_2$, Pt/C, 30 psi, EtOAc, 3 h; (iv) CNBr, MeOH:H$_2$O (1:1), 60° C., 3 h; (v) $C_6H_5$-B(OH)$_2$, $K_2CO_3$, Pd(dppf)Cl$_2$, 1,4-dioxane, 90° C., 12 h; (vi) benzylzinc bromide, Pd(dppf)Cl$_2$, THF, 70° C., 12 h.

Scheme A6 reagents and conditions:

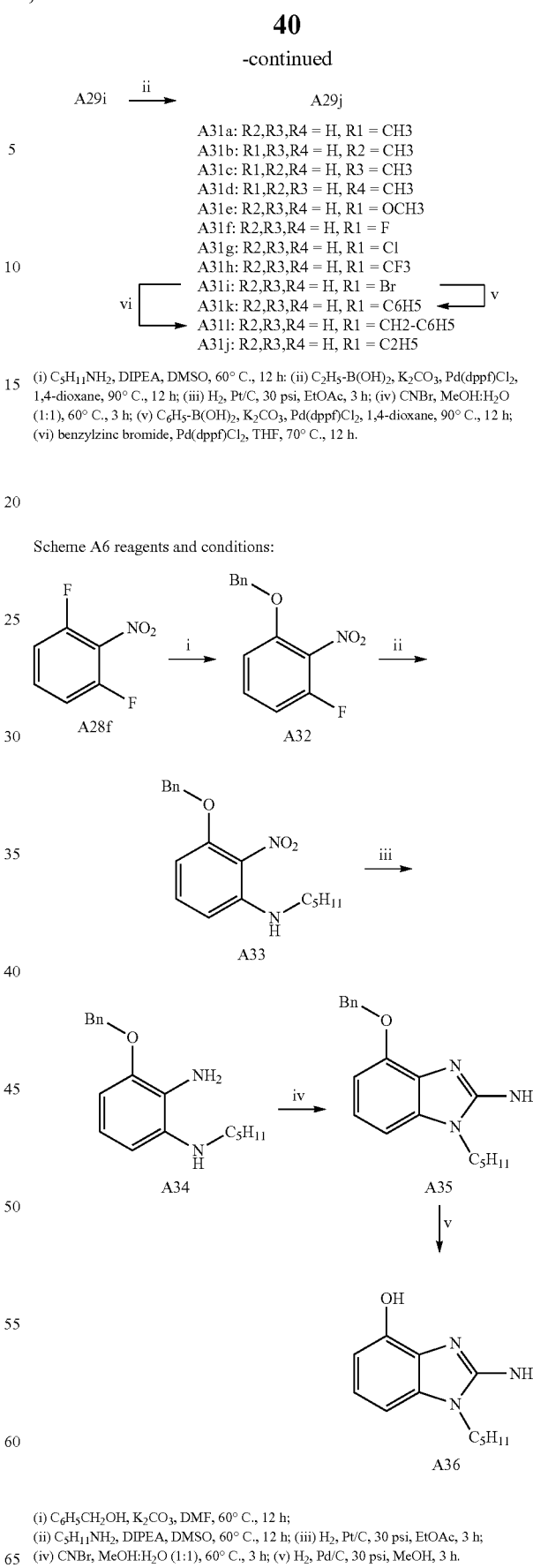

(i) $C_6H_5CH_2OH$, $K_2CO_3$, DMF, 60° C., 12 h;
(ii) $C_5H_{11}NH_2$, DIPEA, DMSO, 60° C., 12 h; (iii) $H_2$, Pt/C, 30 psi, EtOAc, 3 h;
(iv) CNBr, MeOH:H$_2$O (1:1), 60° C., 3 h; (v) $H_2$, Pd/C, 30 psi, MeOH, 3 h.

Scheme A7 reagents and conditions:

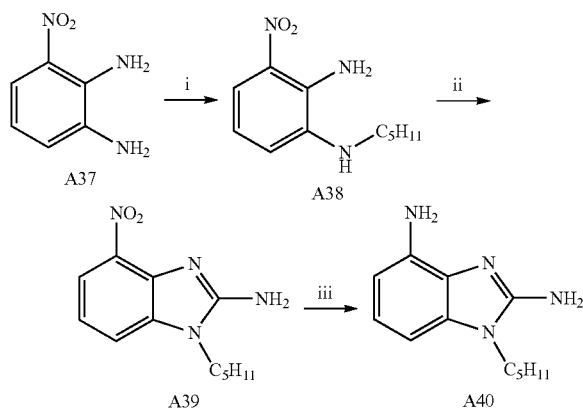

(i) C$_5$H$_{11}$I, K$_2$CO$_3$ DMF, 50° C., 12 h; (ii) CNBr, MeOH:H$_2$O (1:1), 60° C., 3 h; (iii) H$_2$, Pt/C, 30 psi, EtOAc, 3 h.

Induced-fit docking methods were used to compare the binding modes of the 2-aminobenzimidazole analogues with known TLR8 ligands, utilizing high-resolution crystal structures of human TLR8. The TLR8-active analogues such as compound A8b and compound A31a occupy the binding pocket formed by both of the TLR8 protomers with the expected binding geometry involving strong bidentate ionic H bonds between Asp543 of TLR8 and both the C2 amine as well as the N3 atom of the benzimidazole compounds. Stabilization derived from an H bond between Thr574 (protomer B) and the C2-NH$_2$ as well as hydrophobic interactions of the N1-alkyl group with the hydrophobic pocket lined by Phe346/Ile403/Gly376 within protomer A were also observed. Favorable π-π interactions of the phenyl ring of the benzimidazoles and Phe405 were observed. Only the C4-methyl analogue compound A31a, and not congeners bearing methyl groups at C5, C6, or C7 (e.g., compounds A31b-A31d, respectively) showed enhanced potency relative to compound A8b. An examination of compound A31a bound to TLR8 showed favorable van der Waals interactions (3.7 Å) between the C4-methyl and the side chain of Val520, which become unfavorable (5.2 Å) in the C5-methyl analogue compound A31b, and lost entirely in compound A31c and compound A31d (not shown). The occupancy of the benzologues compounds A13, A18 and A23 in the binding pocket is compromised by unfavorable sterics, exemplified in the case of compound A13, forcing the binding of the analogue in an inverted fashion with the consequent loss of the critical H-bond interactions between the C2 amine and Asp543.

All analogues were counter-screened in agonism screens using reporter cell lines specific for human TLR2, TLR3, TLR4, TLR5, TLR7, TLR9, NOD1 and NOD2. No off-target effects were detected, confirming the specificity of the active analogues for human TLR8. Certain benzimidazoles such as Noditinib-1 (1-[(4-methylphenyl)sulfonyl]-1H-benzimidazol-2-amine) have been shown to inhibit NOD-1 signaling, and it was therefore of interest to also characterize possible antagonistic activities. Weak antagonistic activities (IC$_{50}$: >10 μM) toward NOD-1 and NOD-2 were observed for compounds A10, A13, A18, A31l, A31m, and A35; these results suggested that bulky substituents at C4 may yield NOD-1/NOD-2 antagonists.

Figures 7A, 7B:
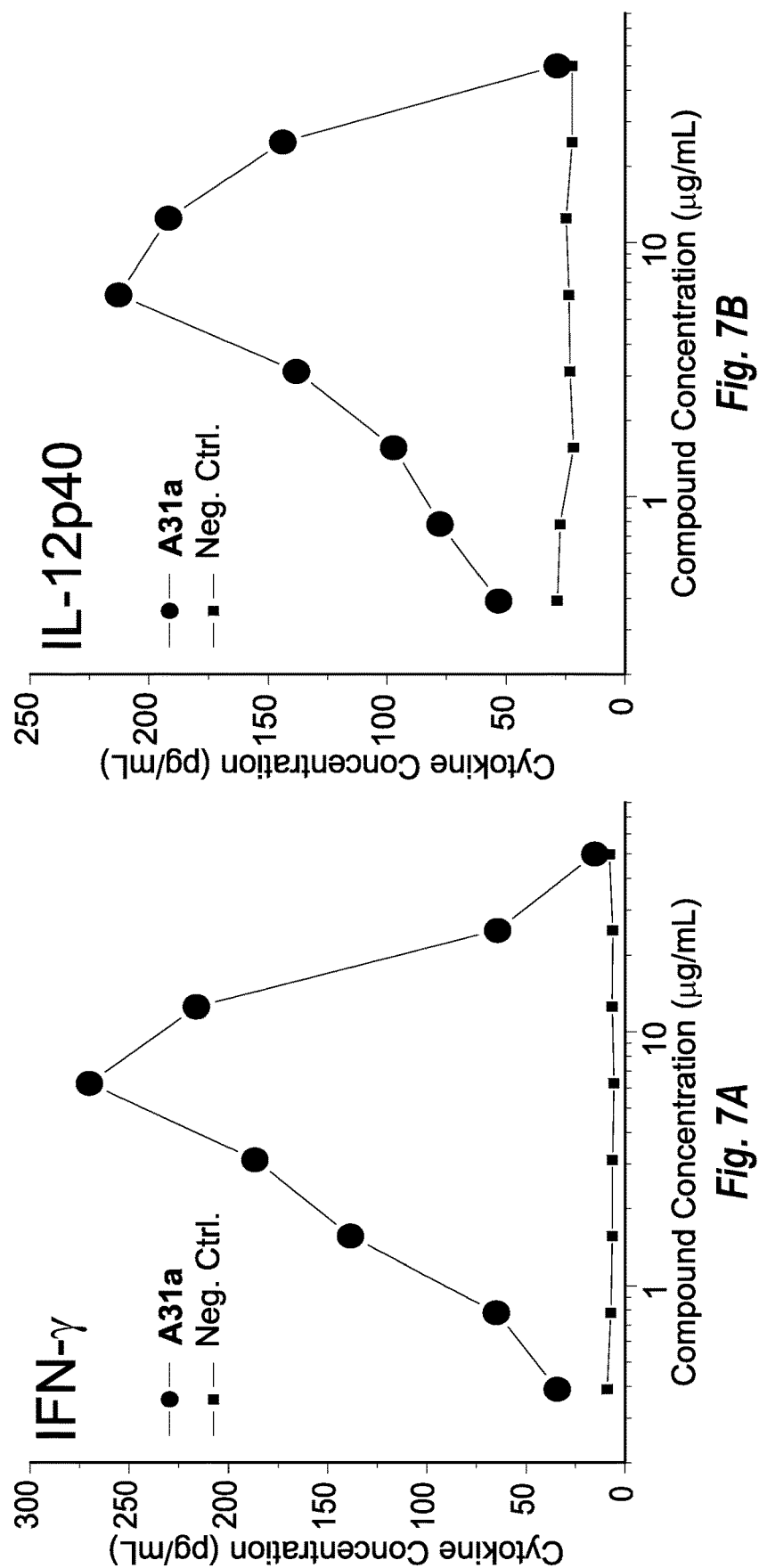
Figures 7E, 7F:
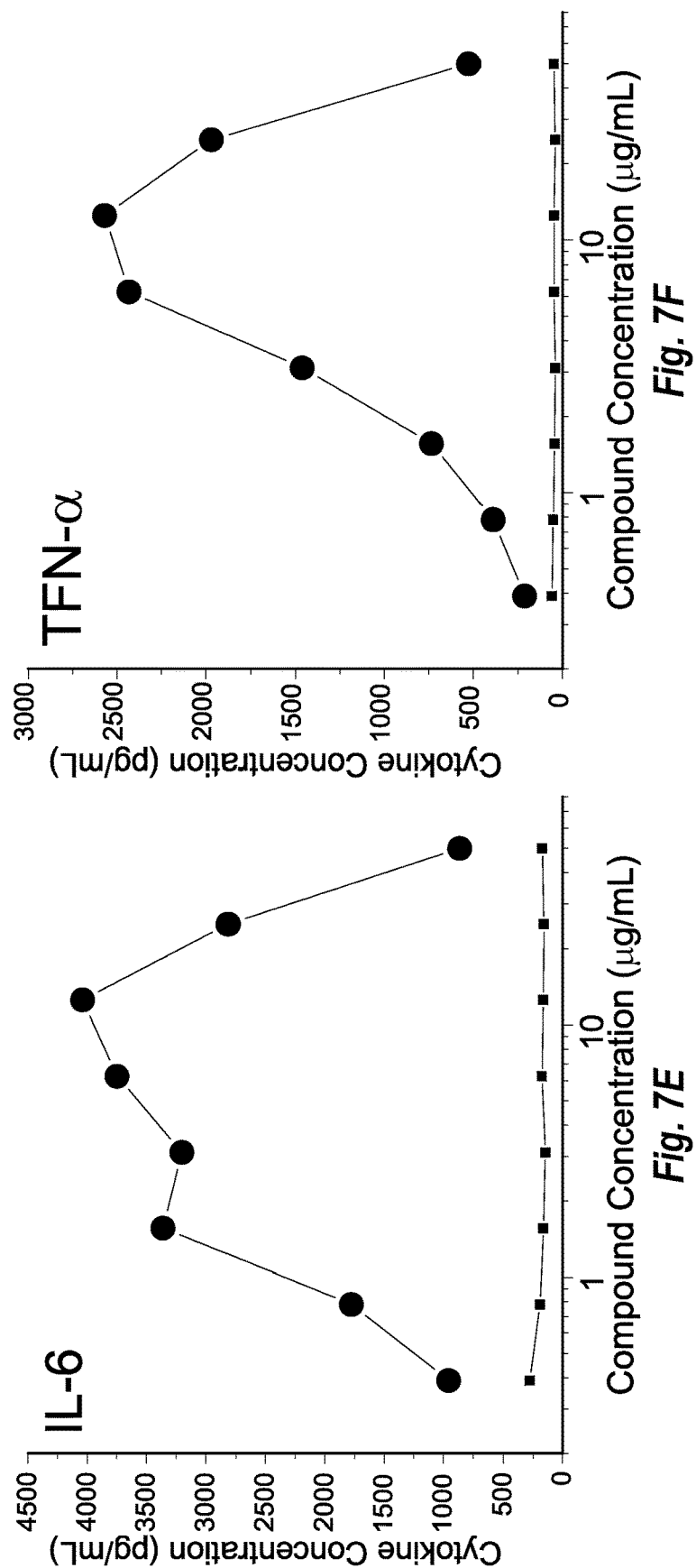
Figure 8B:
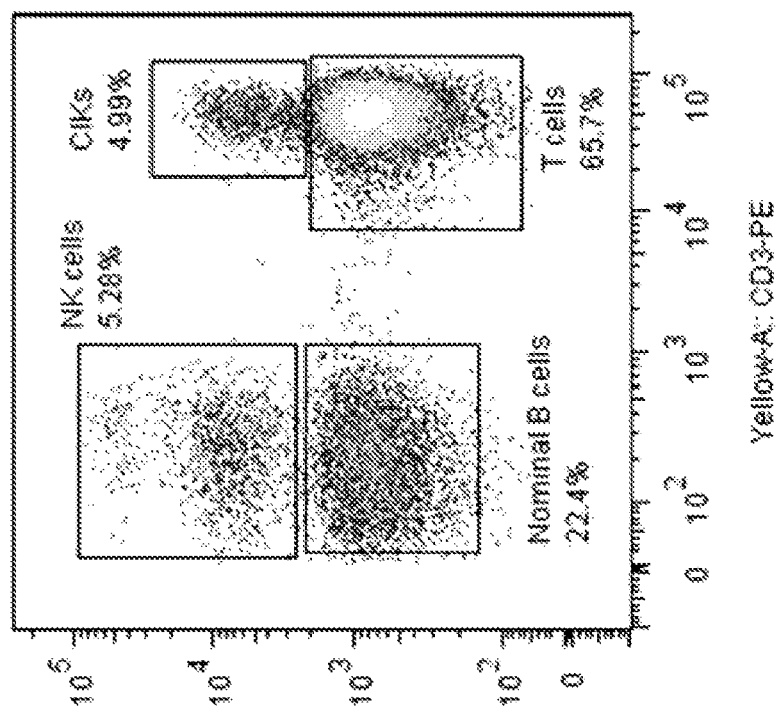
Figure 8A:
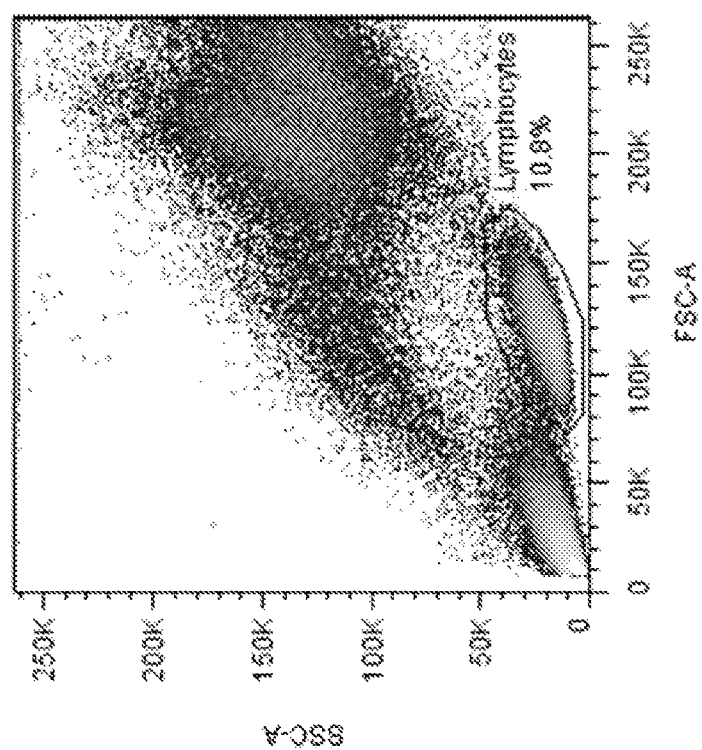
Figure 9:
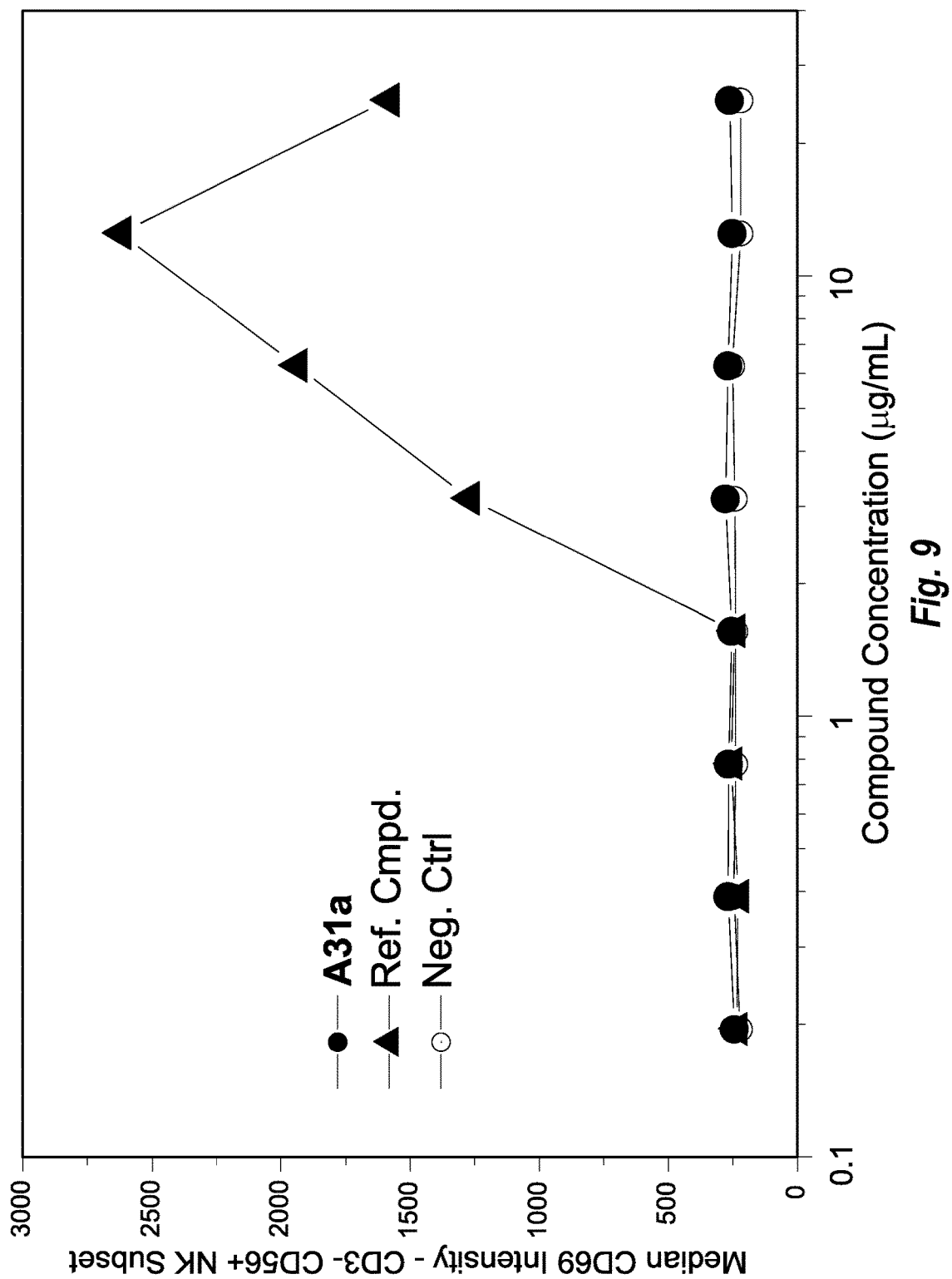
FIG. 9 includes a graph that shows CD69 expression in natural killer lymphocytes. Reference compound used was a pure TLR7 agonist (1-benzyl-2-butyl-1H-imidazo[4,5-c]quinolin-4-amine).

The best-in-class of this novel TLR8-agonistic chemotype, compound A31a was taken forward and characterized further in cytokine/chemokine induction profiles in a panel of secondary screens employing human peripheral blood mononuclear cells, as well as whole human blood. Consistent with its specificity for TLR8, observed induction of proinflammatory cytokines, as well as IL-12p40 and IFN-γ (FIG. 7), and a complete absence of CD69 upregulation in natural killer (NK) lymphocytes (FIG. 9). It had previously been shown that CD69 upregulation in NK cells is ascribable purely to TLR7 activity, and these results confirm absolute specificity of the lead 2-aminobenzimidazole compounds for human TLR8. CD69 is a type II C-lectin membrane receptor with immunoregulatory functions. The absence of CD69 (in CD69 knockout mice) is correlated with increased generation of Th1 lymphocytes and enhanced production of Th1-biasing cytokines, consistent with our observation of induction of high levels of IL-12 and IFN-γ in human PBMCs (FIG. 7).

In summary, the 1-alkyl-1H-benzimidazol-2-amines represent a novel chemotype with human TLR8-specific agonistic activities, which will likely prove useful not only as tools to dissect TLR7 vis-à-vis TLR8 signaling, but also as candidate vaccine adjuvants with strong Th1 bias. Any of the compounds recited as "inactive" in one of the tables can be useful as controls or included as kits for assaying TLR7 or TLR8 agonists or antagonists. Also, the compounds listed as "inactive" in one of the tables may be useful for TLR agonists in other organisms.

TABLE A1

EC$_{50}$ values of Compounds in Human TLR 8-specific Reporter Gene Assays

| Compound Number | Structure | hTLR8 Agonistic Activity (μM) |
|---|---|---|
| A4 | 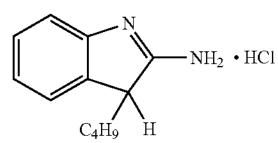 | Unstable |
| A5 | 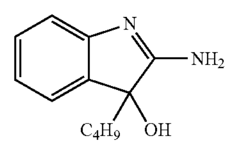 | Inactive |
| A8a | 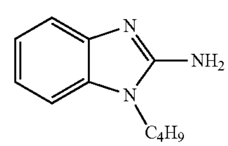 | 7.30 |
| A8b | 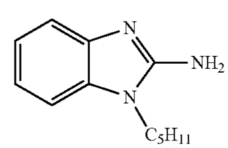 | 3.23 |
| A8c | 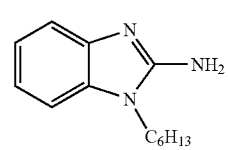 | 3.96 |

TABLE A1-continued

EC$_{50}$ values of Compounds in Human TLR 8-specific Reporter Gene Assays

| Compound Number | Structure | hTLR8 Agonistic Activity (μM) |
|---|---|---|
| A8d | | Inactive |
| A8f | | Inactive |
| A9 | | Inactive |
| A10 | | Inactive |
| A13 | | Inactive |
| A18 | | Inactive |
| A23 | | 3.16 |
| A27a | 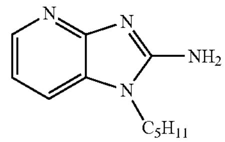 | Inactive |
| A27b | 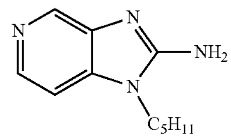 | Inactive |
| A27c | 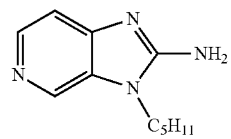 | Inactive |
| A27d | 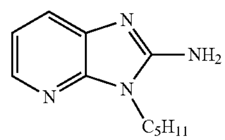 | Inactive |
| A31a | 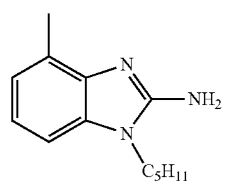 | 1.13 |
| A31b | 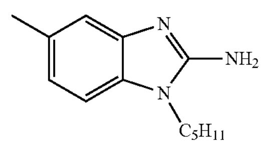 | 4.57 |
| A31c | 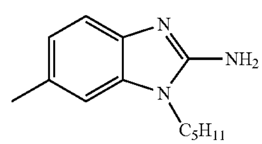 | 7.21 |
| A31d | 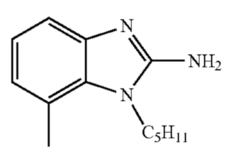 | 6.61 |
| A31e | 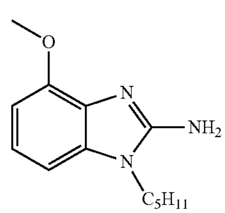 | 3.74 |

TABLE A1-continued

EC$_{50}$ values of Compounds in Human TLR 8-specific Reporter Gene Assays

| Compound Number | Structure | hTLR8 Agonistic Activity (μM) |
|---|---|---|
| A31f | 4-F, 1-C$_5$H$_{11}$ benzimidazol-2-amine | Inactive |
| A31g | 4-Cl, 1-C$_5$H$_{11}$ benzimidazol-2-amine | Inactive |
| A31h | 4-CF$_3$, 1-C$_5$H$_{11}$ benzimidazol-2-amine | Inactive |
| A31i | 4-Br, 1-C$_5$H$_{11}$ benzimidazol-2-amine | Inactive |
| A31j | 4-ethyl, 1-C$_5$H$_{11}$ benzimidazol-2-amine | 1.65 |
| A31k | 4-N(CH$_3$)$_2$, 1-C$_5$H$_{11}$ benzimidazol-2-amine | 7.12 |
| A31ll | 4-phenyl, 1-C$_5$H$_{11}$ benzimidazol-2-amine | Inactive |
| A31m | 4-benzyl, 1-C$_5$H$_{11}$ benzimidazol-2-amine | Inactive |
| A35 | 4-OBn, 1-C$_5$H$_{11}$ benzimidazol-2-amine | Inactive |
| A36 | 4-OH, 1-C$_5$H$_{11}$ benzimidazol-2-amine | 5.01 |
| A39 | 4-NO$_2$, 1-C$_5$H$_{11}$ benzimidazol-2-amine | Inactive |
| A40 | 4-NH$_2$, 1-C$_5$H$_{11}$ benzimidazol-2-amine | 6.60 |

Pharmaceutical Compositions

Provided herein are pharmaceutical compositions comprising a compound provided herein as an active ingredient, including a single enantiomer, a racemic mixture, a mixture of diastereomers, or an isotopic variant thereof; or a pharmaceutically acceptable salt, solvate, or prodrug thereof; or a pharmaceutically acceptable salt, solvate, hydrate, or prodrug; in combination with a pharmaceutically acceptable vehicle, carrier, diluent, or excipient, or a mixture thereof.

Suitable excipients are well known to those skilled in the art, and non-limiting examples of suitable excipients are provided herein. Whether a particular excipient is suitable for incorporation into a pharmaceutical composition or dosage form depends on a variety of factors well known in the art, including, but not limited to, the method of administration. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided herein are pharmaceutical compositions and dosage forms that contain little, if any, lactose, or other mono- or di-saccharides. As used herein, the term "lactose-free" means that the amount of lactose present, if any, is insufficient to substantially increase the degradation rate of an active ingredient. In one embodiment, lactose-free compositions comprise an active ingredient provided herein, a binder/filler, and a lubricant. In another embodiment, lactose-free dosage forms comprise an active ingredient, microcrystalline cellulose, pre-gelatinized starch, and magnesium stearate. The compounds provided herein may be administered alone, or in combination with one or more other compounds provided herein. The pharmaceutical compositions that comprise a compound provided herein including a single enantiomer, a racemic mixture, a mixture of diastereomers, or an isotopic variant thereof; or a pharmaceutically acceptable salt, solvate, or prodrug thereof, can be formulated in various dosage forms for oral, parenteral, intravenous, intramuscular, subcutaneous, and topical administration or the like. The pharmaceutical compositions can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art (see, *Remington: The Science and Practice of Pharmacy, supra; Modified-Release Drug Delivery Technology,* 2nd ed.; Rathbone et al., Eds.; Marcel Dekker, Inc.: New York, N.Y., 2008).

The pharmaceutical compositions provided herein can be provided in a unit-dosage form or multiple-dosage form. A unit-dosage form, as used herein, refers to a physically discrete unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. For example, a 100 mg unit dose contains about 100 mg of an active ingredient in a packaged tablet or capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

When the compound provided herein contains an acidic or basic moiety, it may also be provided as a pharmaceutically acceptable salt. See, Berge et al., *J. Pharm. Sci.* 1977, 66, 1-19; and *Handbook of Pharmaceutical Salts, Properties, and Use*; Stahl and Wermuth, Ed.; Wiley-VCH and VHCA: Zurich, Switzerland, 2002. Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1 S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-aminosalicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound provided herein may also be provided as a prodrug, which is a functional derivative of the compound, for example, of Formula 1 or 1A and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See, Harper, *Progress in Drug Research* 1962, 4, 221-294; Morozowich et al. in *Design of Biopharmaceutical Properties through Prodrugs and Analogs*; Roche Ed., APHA Acad. Pharm. Sci.: 1977.

In one embodiment, a compound can include a structure of Formula 1 or 1A or derivative, prodrug, salt, stereoisomer, tautomer, polymorph, solvate, or combination thereof, wherein: one of the dashed lines is a bond and the other nothing; $X^1$ and $X^2$ are independently C or N; $R^1$-$R^7$ are each independently selected from: (a) hydrogen; (b) —C(O)$R^{1a}$, —C(O)CH(N$R^{1b}R^{1c}$)$R^{1a}$, —C(O)CH(N($R^{1c}$)C(O)$R^{1b}$)$R^{1a}$, —C(O)CH(N(R)C(O)O$R^{1b}$)$R^{1a}$, —C(O)CH(N($R^{1c}$)C(O)N$R^{1b}R^{1d}$)$R^{1a}$, —C(O)O$R^{1a}$, —C(O)N$R^{1b}R^{1c}$, —C(N$R^{1a}$)N$R^{1b}R^{1c}$, —P(O)(O$R^{1a}$)$R^{1d}$, —CH$_2$P(O)(O$R^{1a}$)$R^{1d}$, —S(O)$R^{1a}$, —S(O)$_2R^{1a}$, —S(O)N$R^{1b}R^{1c}$, or S(O)$_2$N$R^{1b}R^{1c}$; (d) two adjacent R groups selected from $R^1$-$R^4$ form a cyclic group selected from an aryl, heteroaryl, polyaryl, polyheteroaryl, or cycloalkyl or cycloheteroaryl; or (c) $C_1$-$C_{24}$ alkyl, $C_2$-$C_{24}$ alkenyl, $C_2$-$C_{24}$ alkynyl, $C_3$-$C_{20}$ cycloalkyl, $C_5$-$C_{20}$ aryl, $C_5$-$C_{20}$ polyaryl, $C_6$-$C_{24}$ alkaryl, $C_6$-$C_{24}$ aralkyl, heteroaryl, heterocyclyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, $C_2$-$C_{24}$ alkylcarbonyl, $C_6$-$C_{20}$ arylcarbonyl, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, or phosphino; and (g) combinations thereof; wherein each R group is optionally substituted by a substituent Q, which substituent Q is defined as $R^1$; wherein $R^{1a}$, $R^{1b}$, $R^{1c}$, or Rid are each independently as defined for $R^1$; when $X^1$ is N, then $R^2$ can be nothing; when $X^2$ is N, then $R^3$ can be nothing; when one of the dashed lines is a bond and the other nothing, the N having the double bond is devoid of a substituent, such that one of $R^5$ or $R^7$ is nothing.

In one aspect, the compound is an active agonist of a TLR, such as TLR7 or TLR8. In one aspect, the compound is specific for one TLR over others, such as specific for TLR7 or TLR8.

In one aspect, the compound excludes compounds that do not agonize a TLR such as TLR7 or TLR8.

In one aspect, the structure is one of Formula 2 or Formula 2A.

In one aspect, when a TLR7 agonist the structure is selected from one of Formula 3, Formula 3A, Formula 4, Formula 4A, Formula 5, Formula 5A, Formula 6, Formula 6A, Formula 7, Formula 7A, Formula 8, Formula 8A, Formula 9, Formula 9A, Formula 10, Formula 10A, Formula 11, or Formula 11A, wherein $R^8$, $R^9$, $R^{10}$, and $R^{11}$ are each independently as defined for $R^1$. In one aspect, $R^1$ is hydrogen and $R^3$-$R^4$ are each independently selected from:

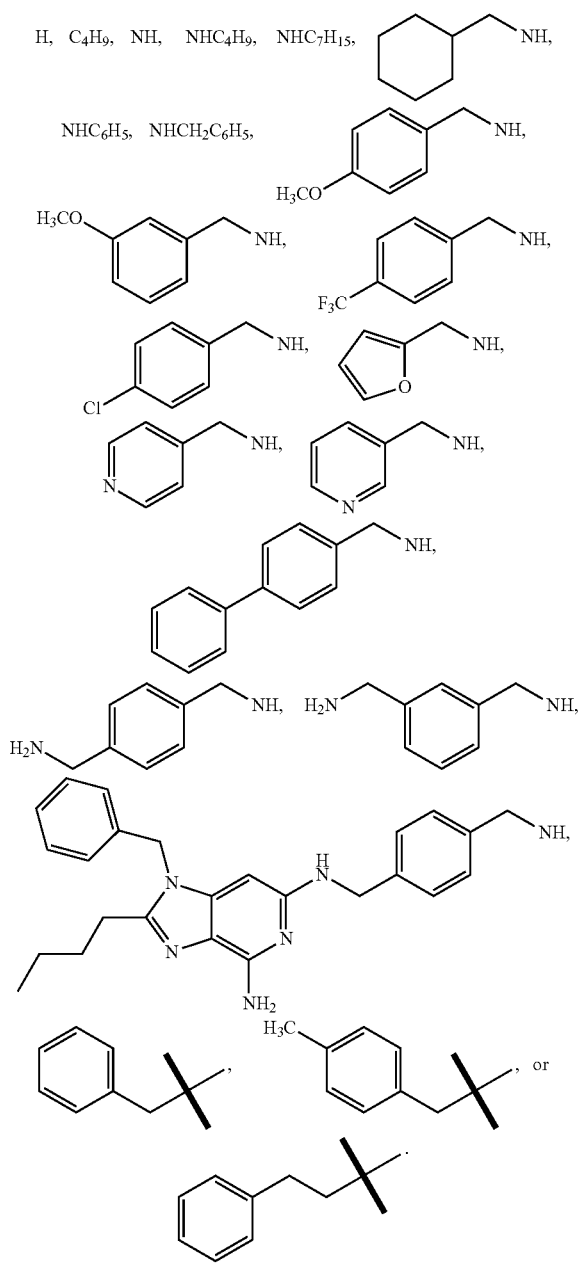

In one aspect, the compound is shown in Table 1 or is a derivative thereof, which derivative modifies an R group variable of one of the formulae. In one aspect, compound 19a can be modified so that the $R^3$ substituent is on $R^4$, which modification can be performed with any compound illustrated to move the $R^3$ substituent to the $R^4$ location. In one aspect, compounds 19b and 19c can have longer alkyl groups extending from the nitrogen or two alkyl groups on the nitrogen, and which may be substituted or unsubstituted, which modification can be performed with any compound illustrated on the $R^3$ substituent or on the $R^4$ location. In one aspect, compound 19d can include a longer alkyl group between the nitrogen and the cyclo alkyl group, and another alkyl group may optionally be meta, para, or ortho from the nitrogen, which modification can be performed with any compound illustrated on the $R^3$ substituent or on the $R^4$ location. In one aspect, compound 19g or 19h can include a longer alkyl group between the nitrogen and the aryl group, and another alkyl group may optionally be meta, para, or ortho from the nitrogen optionally with the alkoxy, which modification can be performed with any compound illustrated on the $R^3$ substituent or on the $R^4$ location. In one aspect, compounds 19i and 19j can have the halogens substituted with other halogens, which modification can be performed with any compound illustrated on the $R^3$ substituent or on the $R^4$ location.

In one aspect, the compound is a TLR7 agonist and is selected from one of compounds 5, 19a, 19b, 19c, 19d, 19e, 19f, 19g, 19h, 19i, 19j, 19k, 19l, 19m, 19o, 19p, 19q, 19r, 23a, 23g, 23h and 23j or 30. In one aspect, the compound is a TLR7 agonist that has the $R^3$ substituent of Table 1 on the $R^4$ location of one of compounds 5, 19a, 19b, 19c, 19d, 19e, 19f, 19g, 19h, 19i, 19j, 19k, 19l, 19m, 19o, 19p, 19q, 19r, 23a, 23g, 23h and 23j, and the $R^3$ substituent is H. In one aspect, the compound is a TLR7 agonist that has the $R^3$ substituent of Table 1 on the $R^3$ and $R^4$ location of one of compounds 5, 19a, 19b, 19c, 19d, 19e, 19f, 19g, 19h, 19i, 19j, 19k, 19l, 19m, 19o, 19p, 19q, 19r, 23a, 23g, 23h and 23j. In these embodiments, the other R groups are as illustrated in Table 1.

In one embodiment, the compound is a TLR7 agonist and $R^1$ is hydrogen, $R^2$ is nothing, $R^5$ is alkylaryl (e.g., benzyl), $R^6$ is short alkyl (e.g., C1-C6; butyl), and $R^7$ is nothing, where the substituent on $R^3$ in Table 1 is on $R^3$ and/or $R^4$, wherein the R3 substituent may be a derivative thereof, such as described herein. In this embodiment, $X^1$ is N and $X^2$ is C.

In one aspect, the phenyl group in compound 30 formed from $R^3$ and $R^4$ can be another aryl, heteroaryl, polyaryl, polyheteroaryl, substituted or unsubstituted with Q.

In one aspect, when a TLR8 agonist the structure is selected from one of Formula 12, Formula 13, Formula 14, Formula 15, Formula 16, Formula 17, Formula 18, or Formula 18A. In one aspect, $R^1$-$R^5$ are each independently selected from hydrogen; $C_{1-24}$ alkyl, $C_{2-24}$ alkenyl, $C_{2-24}$ alkynyl, or $C_{3-24}$ cycloalkyl; $R^6$ is $NH_2$; $R^7$ is nothing; and the dashed line linked to the N of $R^7$ is a bond and the other dashed line is nothing. In this embodiment, $X^1$ is C and $X^2$ is C.

In one aspect, the compound is shown in Table A1 or is a derivative thereof, which derivative modifies an R group variable of one of the formulae. In one aspect, a compound can be modified so that the $R^1$ substituent is on $R^2$, which modification can be performed with any compound illustrated to move the $R^1$ substituent to the $R^2$ location. In one aspect, compounds can have longer alkyl groups extending from the aryl or two alkyl groups on the aryl for the R groups, and which may be substituted or unsubstituted, which modification can be performed with any compound illustrated. In one aspect, a compound can include a longer alkyl group on the $R^5$ location.

In one aspect, compound is a TLR8 agonist selected from one of compounds A8a, A8b, A8c, A31a, A31b, A31c, A31d, A31e, A31j, A31k, A36, and A40 or A23. In one aspect, the compound is a TLR8 agonist that has the $R^1$ substituent of Table A1 on the $R^2$ location of one of compounds A8a, A8b, A8c, A31a, A31 b, A31c, A3 d, A31e, A31 j, A31 k, A36, and A40 or A23, where $R^1$, $R^3$, and $R^4$ are hydrogen. In one aspect, the compound is a TLR8 agonist that has the $R^1$ substituent of Table A1 on the $R^3$ location of one of compounds A8a, A8b, A8c, A31a, A31b, A31c, A31d, A31e, A31j, A31k, A36, and A40 or A23, where $R^1$, $R^2$, and $R^4$ are hydrogen. In one aspect, the compound is a TLR8 agonist that has the $R^1$ substituent of Table A1 on the $R^4$ location of one of compounds A8a, A8b, A8c, A31a, A31b, A31c, A31d, A31e, A31j, A31k, A36, and A40 or A23, where $R^1$, $R^2$, and $R^3$ are hydrogen. In these embodiments, the other R groups are as illustrated in Table A1.

In one embodiment, the compound is a TLR8 agonist and $R^1$ is hydrogen or alkyl (e.g., C1-C6), $R^2$ is hydrogen or an alkyl (e.g., C1-C6) or alkoxy or amine or alkylamine or hydroxyl, $R^3$ is hydrogen or an alkyl (e.g., C1-C6) or alkoxy or amine or alkylamine or hydroxyl, $R^4$ is hydrogen or an alkyl (e.g., C1-C6) or alkoxy or amine or alkylamine or hydroxyl, $R^5$ is alkyl (e.g., C1-C12, or C2-C10, C3-C8, or C4-C6), $R^6$ is amine, and $R^7$ is nothing, where the substituent on $R^1$ in Table A1 is on $R^1$ and/or $R^2$, wherein the R group substituent may be a derivative thereof, such as described herein. In this embodiment, $X^1$ is N and $X^2$ is C.

In one aspect, the phenyl group in compound A23 off $R^1$ and $R^2$ can be another aryl, heteroaryl, polyaryl, polyheteroaryl, substituted or unsubstituted with Q.

In one embodiment, the compound is compound 19p.

In one embodiment, the compound is compound A31a.

In one embodiment, a pharmaceutical composition can include a compound and a pharmaceutically acceptable carrier. In one aspect, the composition is configured for oral administration, parenteral administration, intravenous administration, topical administration, or subcutaneous administration. In one aspect, the compound is present in an amount sufficient for agonizing a Toll-Like Receptor (TLR), such as TLR7 or TLR8, and may be specific for only one TLR. In one aspect, the TLR is TLR7, and the structure of the compound is selected from one of Formula 1, Formula 1A, Formula 2, Formula 2A, Formula 3, Formula 3A, Formula 4, Formula 4A, Formula 5, Formula 5A, Formula 6, Formula 6A, Formula 7, Formula 7A, Formula 8, Formula 8A, Formula 9, Formula 9A, Formula 10, Formula 10A, Formula 11, or Formula 11A, such as a compound from Table 1. In one aspect, the TLR is TLR8, wherein the structure of the compound is selected from Formula 12, Formula 13, Formula 14, Formula 15, Formula 16, Formula 17, Formula 18, and Formula 18A, such as a compound from Table A1. In one aspect, the composition is a vaccine and includes a vaccine agent. The vaccine agent is the entity to which the vaccine provides for immunogenicity thereto.

In one embodiment, a method of agonizing a Toll-Like Receptor (TLR) can include providing a compound of one of the embodiments to a TLR in an amount sufficient to agonize the TLR. The TLR can be in vitro or in vivo. In one aspect, the TLR is TLR7, wherein the structure of the compound is selected from one of Formula 1, Formula 1A, Formula 2, Formula 2A, Formula 3, Formula 3A, Formula 4, Formula 4A, Formula 5, Formula 5A, Formula 6, Formula 6A, Formula 7, Formula 7A, Formula 8, Formula 8A, Formula 9, Formula 9A, Formula 10, Formula 10A, Formula 11, or Formula 11A, such as in Table 1 or derivative thereof. In one aspect, the TLR is TLR8, wherein the structure of the compound is selected from Formula 12, Formula 13, Formula 14, Formula 15, Formula 16, Formula 17, Formula 18, and Formula 18A, such as in Table A1 or derivative thereof.

In one embodiment, a method of improving vaccination can include administering a vaccine agent (e.g., having an antigen) to a subject along with a compound of one the embodiments in an amount sufficient to function as an adjuvant with regard to the vaccine agent. The compound can be from Table 1 or Table 1A, or derivative thereof. The improved vaccination method can include agonizing a Toll-Like Receptor (TLR) in the subject. In one aspect, the TLR is TLR7, wherein the structure of the compound is selected from one of Formula 1, Formula 1A, Formula 2, Formula 2A, Formula 3, Formula 3A, Formula 4, Formula 4A, Formula 5, Formula 5A, Formula 6, Formula 6A, Formula 7, Formula 7A, Formula 8, Formula 8A, Formula 9, Formula 9A, Formula 10, Formula 10A, Formula 11, or Formula 11A. In one aspect, the TLR is TLR8, wherein the structure of the compound is selected from Formula 12, Formula 13, Formula 14, Formula 15, Formula 16, Formula 17, Formula 18, and Formula 18A.

In one aspect, the method can include agonizing the TLR so as to increase production of inflammatory cytokines. In one aspect, the method can include agonizing the TLR so as to up-regulate major histocompatibility complex (MHC) molecules and co-stimulatory signals in antigen-presenting cells. In one aspect, the method can include agonizing the TLR so as to activate natural killer (NK) cells. In one aspect, the method can include agonizing the TLR so as to cause an adaptive immune response to the vaccine agent. In one aspect, the method can include agonizing the TLR so as to induce production of T helper 1-polarizing cytokines.

In one aspect, the subject is a youth under 10, 5, 4, 3, 2, or 1 years of age or a newborn younger than 12 months, 6 months, 4 months, 3 months, 2 months, or 1 month.

In one aspect, the subject is elderly, and the subject is elderly above 50, 60, or 70 years of age.

In one aspect, the compound is active for TLR7 and inactive to TLR8.

In one aspect, the compound active for TLR8 and inactive to TLR7.

In one embodiment, a method of activating an immune system can include administering an immunological agent to a subject along with a compound of one of the embodiments in an amount sufficient to function as an adjuvant with regard to the immunological agent. The compound can be from Table 1 or A1 or derivative thereof.

In one embodiment, a method of treating allergic bronchitis can include administering to a subject a compound of one of the embodiments, such as from Table 1 or 1A. In one aspect, the subject has allergic bronchitis and is in need of treatment. In one aspect, the compound is compound 19p.

In one aspect, the subject of a method is in need of a therapy, such as vaccination or treatment.

In one embodiment, a method of treating bronchospastic disorder can include administering to a subject a compound of one of the embodiments, such as from Table 1 or Table 1A. In one aspect, the subject has bronchospastic disorder and is in need of treatment. In one aspect, the compound is compound 19p.

In one embodiment, the compounds can be used as treatments for hepatitis, such as hepatitis C. The compounds can be from Table 1 or 1A, or derivative thereof.

In one embodiment, the compound can be degraded quickly upon administration. A potential advantage is that because the compounds can be broken down so quickly, systemic side effects that come from Type 1 interferon induction or pro inflammatory cytokine induction can be limited to just the site of injection. This can be useful for vaccination and minimize side effects. Thus, the compounds can be adjuvants that reduce adverse side effects of vaccination, such as reduced fever or inflammation. These compounds can be the TLR7 agonists, such as from Table 1 or derivative thereof.

In one embodiment, methods of treating bronchial asthma and atopic bronchitis can include administering the TLR8 agonists, such as from Table A1 or derivative thereof.

In one embodiment, a method of activating a cytotoxic T lymph response can include administering a TLR8 agonist, such as from Table A1 or derivative thereof.

In one embodiment, a TLR7 agonist can have R3 and/or R4 having a substituent that can hydrogen boding acceptors or donors. Here, the other R groups can be as shown in Table 1.

In one embodiment, a TLR agonist can have one or two atoms or more between the aryl ring and a group on the R3 or R4 substituent. The group can be a hydrogen donor or acceptor group. In one aspects, there are at least 2 atoms between the aryl ring and the hydrogen donor or acceptor group. The atoms can be a N and/or C.

Applicants submit that the activity of compound 30 indicates that the $R^3$ and/or $R^4$ locations can have substituents. That is, the $R^3$ groups in compounds that show activity may also be on the $R^4$ location or only on the $R^4$ location. These can be TLR7 agonists from Formulae 3-11.

Applicants submit that the activity of compound A23 indicates that the $R^1$ and/or $R^2$ locations can have substituents. That is, the R groups in compounds that show activity may be on the $R^1$ and $R^2$ location or only on the $R^1$ or $R^2$ location. These can be TLR8 agonists from Formulae 12-18.

EXPERIMENTAL

TLR7

Materials and Equipment.

All of the solvents and reagents used were obtained commercially and used as such unless noted otherwise. Moisture- or air-sensitive reactions were conducted under nitrogen atmosphere in oven-dried (120° C.) glass apparatus. The solvents were removed under reduced pressure using standard rotary evaporators. Flash column chromatography was carried out using RediSep $R_f$ 'Gold' high performance silica columns on CombiFlash $R_f$ instrument unless otherwise mentioned, while thin-layer chromatography was carried out on silica gel (200 μm) CCM pre-coated aluminum sheets. Purity for all final compounds was confirmed to be greater than 97% by LC-MS using a Zorbax Eclipse Plus 4.6 mm×150 mm, 5 μm analytical reverse phase $C_{18}$ column with $H_2O$-isopropanol or $H_2O$—$CH_3CN$ gradients and an Agilent 6520 ESI-QTOF Accurate Mass spectrometer (mass accuracy of 5 ppm) operating in the positive ion (or negative ion, as appropriate) acquisition mode.

Synthesis of Compound 1:
N-Benzyl-3-nitropyridin-4-amine

To a solution of 4-chloro-3-nitropyridine (1.0 g, 6.31 mmol) in 25 mL of $CH_2Cl_2$ were added triethylamine (1.32 mL, 9.47 mmol) and benzyl amine (0.83 mL, 7.57 mmol). The reaction mixture was refluxed for 18 h. The solvent was then evaporated under vacuum and $H_2O$ was added to the residue. The solution was extracted with $CH_2Cl_2$ (3×20 mL), washed with water and dried over sodium sulfate. The solvent was evaporated and the residue was purified using silica gel column chromatography (5% MeOH/$CH_2Cl_2$) to obtain compound 1 as a yellow solid (1.4 g, 94%).

Synthesis of Compound 2:
$N^4$-Benzylpyridine-3,4-diamine

To a solution of compound 1 (1.0 g, 4.36 mmol) in 40 mL of MeOH were added zinc dust (1.4 g, 21.8 mmol) and ammonium formate (1.4 g, 21.8 mmol). The reaction mixture was stirred at room temperature for 10 min and filtered through celite. Then the solvent was evaporated and the residue was dissolved in water. This was extracted with EtOAc (3×20 mL), washed with water and dried over sodium sulfate. The solvent was evaporated under vacuum to obtain the compound 2 (0.8 g, 92%).

Synthesis of Compound 3: 1-Benzyl-2-butyl-1H-imidazo[4,5-c]pyridine

To a solution of compound 2 (400 mg, 2.00 mmol) in 20 mL of anhydrous THF were added triethylamine (0.29 mL, 2.10 mmol) and valeryl chloride (0.27 mL, 2.20 mmol). The reaction mixture was refluxed for 2 h. The solvent was then removed under vacuum, and the residue was dissolved in EtOAc and washed with water. The EtOAc fraction was dried using sodium sulfate and evaporated under vacuum to obtain the intermediate amide compound. This was dissolved in 20 mL of EtOH and NaOH (160 mg, 4.00 mmol) in 2 mL of $H_2O$ was added. The reaction mixture was refluxed for 4 h. The solvent was then removed under vacuum, and the residue was dissolved in EtOAc and washed with water. The organic layer was dried using sodium sulfate and evaporated and purified using column chromatography (5% $MeOH/CH_2Cl_2$) to obtain the compound 3 (210 mg, 40%).

Synthesis of Compound 4: 1-Benzyl-2-butyl-1H-imidazo[4,5-c]pyridine 5-oxide

To a solution of compound 3 (210 mg, 0.79 mmol) in 15 mL of was added m-chloroperoxybenzoic acid (443 mg, 1.98 mmol), and the solution was refluxed at 45-50° C. for 1 h. The solvent was then removed and the residue was purified using column chromatography (10% $MeOH/CH_2Cl_2$) to obtain the N-oxide derivative (188 mg, 85%).

Synthesis of Compound 5: 1-Benzyl-2-butyl-1H-imidazo[4,5-c]pyridin-4-amine

To a solution of compound 4 (188 mg, 0.67 mol) in 15 mL of $CH_2Cl_2$ was added benzoyl isocyanate (197 mg, 1.34 mmol) and heated at 45° C. for 2 h. The solvent was then removed under vacuum, and the residue was dissolved in 15 mL of anhydrous MeOH, followed by the addition of excess sodium methoxide. The reaction mixture was then heated at 80° C. for 1 h. The solvent was removed under vacuum and the residue was purified using column chromatography (7% $MeOH/CH_2Cl_2$) to obtain the compound 5 (56 mg, 30%).

Synthesis of Compound 6a: N-(1-Benzyl-2-butyl-1H-imidazo[4,5-c]pyridin-4-yl)acetamide To a solution of compound 5 (30 mg, 0.11 mmol) in 2 mL of $CH_2Cl_2$ were added triethylamine (17 μL, 0.12 mmol) and acetyl chloride (8 μL, 0.11 mmol). The reaction mixture was stirred at room temperature for 3 h and purified using column chromatography (5% $MeOH/CH_2Cl_2$) to obtain the compound 6a as white solid (6 mg, 16%). Compound 6b was synthesized similarly as compound 6a.

N-(1-Benzyl-2-butyl-1H-imidazo[4,5-c]pyridin-4-yl) butyramide (6b)

Butyryl chloride was used as a reagent. (4 mg, 14%).

Synthesis of Compound 10a: 1-Benzyl-2-butyl-4-chloro-1H-imidazo[4,5-c]pyridine

4-Amino-2-chloropyridine (2.0 g, 15.6 mmol) was taken in 20 mL of conc. $H_2SO_4$ in an ice-bath to which was added 10 mL of conc. $HNO_3$ slowly. The reaction mixture was gradually brought to room temperature and stirred for 1 h. The reaction was quenched by pouring the reaction mixture on ice. Ammonium hydroxide solution was slowly added until a pH of 3.0 was reached. A white solid was obtained which was filtered, washed with water, and dried. This (N-nitro)aminopyridine intermediate was taken up in 10 mL of conc. $H_2SO_4$ and the reaction solution was heated at 90° C. for 30 min. It was cooled to room temperature and poured into ice. It was slowly neutralized with ammonium hydroxide solution until a pH of 7 and the formed yellow solid was filtered, washed with water and dried to obtain compound 7 as a mixture of 2-chloro-3-nitropyridin-4-amine and 2-chloro-5-nitropyridin-4-amine intermediates. Sodium hydride (275 mg, 6.90 mmol) was carefully added to 20 mL of THF under $N_2$ and compound 7 (1.0 g, 5.76 mmol) was slowly added to the solution at 0° C. The reaction mixture was stirred for 1 h, followed by the addition of benzyl bromide (0.75 mL, 6.34 mmol). The reaction mixture was stirred at room temperature for 2 h and poured into ice water. Then it was extracted with EtOAc (3×20 mL), washed with water, dried over sodium sulfate. The solvent was removed and the crude residue was purified using column chromatography (20% EtOAc/hexane) to obtain the compound 8 as a mixture of regioisomeric N-benzyl-2-chloro-3-nitropyridin-4-amine and N-benzyl-2-chloro-5-nitropyridin-4-amine intermediates. To this regioisomeric mixture (1.0 g, 4.2 mmol) in 20 mL of MeOH were added zinc dust (1.4 g, 21.0 mmol) and ammonium formate (1.4 g, 21.0 mmol). The reaction mixture was stirred at room temperature for 10 min and filtered through celite. Then the solvent was evaporated and the residue was dissolved in water. This was extracted with EtOAc (3×20 mL), washed with water and dried over sodium sulfate. The filtrate evaporated under vacuum, and chromatographed (20% EtOAc/hexane) to obtain the required $N^4$-benzyl-2-chloropyridine-3,4-diamine compound 9a. Also obtained was $N^4$-benzyl-6-chloropyridine-3,4-diamine as a side-product. To a solution of compound 9a (495 mg, 2.12 mmol) in 20 mL of anhydrous THF were added triethylamine (0.31 mL, 2.23 mmol) and valeryl chloride (0.28 mL, 2.33 mmol). The reaction mixture was refluxed for 1 h. The solvent was then removed under vacuum, and the residue was dissolved in 20 mL of EtOH and NaOH (170 mg, 4.24 mmol) in 2 mL of $H_2O$ was added. The reaction mixture was refluxed for 2 h. The solvent was then removed under vacuum, and the residue was dissolved in EtOAc and washed with water. The EtOAc fraction was dried using sodium sulfate and evaporated and purified using column chromatography (5% $MeOH/CH_2Cl_2$) to obtain the compound 10a (203 mg, 32%).

Synthesis of Compound 11a: 1-Benzyl-N,2-dibutyl-1H-imidazo[4,5-c]pyridin-4-amine To a solution of compound 10 (50 mg, 0.17 mmol) in 1 mL of dioxane were added potassium tert-butoxide (57 mg, 0.51 mmol), catalytic amount of 2-dicyclohexylphosphino-2'-(N,N-dimethylamino)biphenyl (DavePhos) and tris(dibenzylideneacetone)dipalladium(0) ($Pd_2(dba)_3$) and butyl amine (83 μL, 0.83 mmol). The reaction mixture was then heated under microwave conditions (500 W, 100° C.) in a sealed vial for 1 h. It was cooled to room temperature and filtered through celite and washed with MeOH. The solvent was removed and the crude residue was purified using column chromatography (5% MeOH/CH$_2$Cl$_2$) to obtain the compound 11a (21 mg, 36%). Compound 1b was synthesized similarly as compound 11a.

N,1-Dibenzyl-2-butyl-1H-imidazo[4,5-c]pyridin-4-amine (11b)

Benzyl amine was used as a reagent.

Synthesis of Compound 11c: 1-Benzyl-4-butoxy-2-butyl-1H-imidazo[4,5-c]pyridine

To a suspension of sodium hydride (48 mg, 2.00 mmol) in 2 mL of anhydrous THF was added 1-butanol (0.18 mL, 2.00 mmol). It was stirred at room temperature for 1 h, followed by the addition of compound 10 (100 mg, 0.33 mmol). The reaction mixture was heated at 60° C. for 18 h and then solvent was evaporated under vacuum. The residue was extracted with EtOAc (3×10 mL), washed with water and dried over sodium sulfate. The solvent was removed and the crude residue was purified using column chromatography (5% MeOH/CH$_2$C2) to obtain the compound 11c (61 mg, 55%).

Synthesis of Compound 12: 2,6-Dichloro-3-nitropyridin-4-amine

4-Amino-2,6-dichloropyridine (2.0 g, 12.27 mmol) was added to 20 mL of conc. H$_2$SO$_4$. The mixture was cooled to 0° C. and 10 mL of conc. HNO$_3$ was dropwise at 0° C. The reaction mixture was stirred at room temperature for 1 h and then poured into crushed ice. The white solid was filtered, washed with water and dried. This intermediate was dissolved in 10 mL of conc. H$_2$SO$_4$ and the reaction solution was heated at 90° C. for 30 min. It was cooled to room temperature and poured into ice. It was slowly neutralized with ammonium hydroxide solution until a pH of 9 and the formed yellow solid was filtered, washed with water and dried to obtain compound 12 as light yellow solid.

Synthesis of Compound 13: N-Benzyl-2,6-dichloro-3-nitro pyridin-4-amine

Sodium hydride (138 mg, 5.77 mmol) was carefully suspended in 10 mL of dry THF under N$_2$. The grey suspension was cooled to 0° C. and compound 12 (1.0 g, 4.81 mmol) was slowly added to the suspension at 0° C. The reaction mixture was stirred for 1 h, followed by the addition of benzyl bromide (0.5 mL, 5.29 mmol). The reaction mixture was stirred at room temperature for 2 h and poured into ice water. Then it was extracted with EtOAc (3×20 mL), washed with water, dried over sodium sulfate. The solvent was removed and the crude residue was purified using column chromatography (20% EtOAc/hexane) to obtain the compound 13 as yellow solid.

Synthesis of Compound 14: N$^4$-Benzyl-6-chloro-3-nitro-N$^2$-(2,4,4-trimethylpentan-2-yl)pyridine-2,4-diamine To a solution of compound 13 (300 mg, 1.02 mmol) in 20 mL of CH$_2$Cl$_2$ were added triethylamine (0.21 mL, 1.53 mmol) and tert-octylamine (0.5 mL, 3.06 mmol). The reaction mixture was refluxed for 48 h and the solvent was removed under vacuum. The crude residue was purified using column chromatography (20% EtOAc/hexane) to obtain the compound 14 as yellow solid (360 mg, 91%).

Synthesis of Compound 16: 1-Benzyl-2-butyl-6-chloro-N-(2,4,4-trimethylpentan-2-yl)-1H-imidazo[4,5-c]pyridin-4-amine To a solution of compound 14 (260 mg, 0.66 mmol) in 20 mL of MeOH were added zinc dust (434 mg, 6.60 mmol) and ammonium formate (416 mg, 6.60 mmol). The reaction mixture was stirred at room temperature for 10 min and filtered through celite. Then the solvent was evaporated and the residue was dissolved in water. This was extracted with EtOAc (3×20 mL), washed with water and dried over sodium sulfate. The solvent was removed under vacuum to obtain compound 15, brown oil (184 mg, 77%). To a solution of compound 15 (184 mg, 0.50 mmol) in 10 mL of anhydrous THF were added triethylamine (74 µL, 0.52 mmol) and valeryl chloride (62 µL, 0.50 mmol). The reaction mixture was refluxed for 1 h. The solvent was then removed under vacuum, and the residue was dissolved in 10 mL of EtOH and NaOH (40 mg, 1.00 mmol) in 1 mL of H$_2$O was added. The reaction mixture was refluxed for 5 h. The solvent was then removed under vacuum, and the residue was dissolved in EtOAc and washed with water. The EtOAc fraction was dried using sodium sulfate and evaporated and purified using column chromatography (20% EtOAc/hexane) to obtain the compound 16 as yellow solid (120 mg, 56%).

Synthesis of Compound 17: 1-Benzyl-2-butyl-6-chloro-1H-imidazo[4,5-c]pyridin-4-amine Compound 16 (34 mg, 0.082 mmol) was dissolved in 1 mL of HCl (4M in dioxane) and stirred at room temperature for 30 min. Then the solvent was removed under vacuum to obtain compound 17 (11 mg, 42%).

Synthesis of Compound 19a: 1-Benzyl-2-butyl-1H-imidazo[4,5-c]pyridine-4,6-diamine To a solution of compound 16 (70 mg, 0.16 mmol) in 1 mL of dioxane were added potassium tert-butoxide (92 mg, 0.82 mmol), catalytic amount of DavePhos and Pd$_2$(dba)$_3$ and tert-octylamine (83 µL, 0.83 mmol). The reaction mixture was then heated under microwave conditions (500 W, 100° C.) in a sealed vial for 1 h. It was cooled to room temperature and filtered through celite and washed with MeOH. The solvent was removed and the crude residue was purified using column chromatography (20% EtOAc/hexane) to obtain the compound 18a, brown solid (41 mg, 49%). Compound 18a (33 mg, 0.063 mmol) was dissolved in 1 mL of HCl (4M in dioxane) and stirred at room temperature for 30 min. Then the solvent was removed under vacuum to obtain compound 19a as brown solid (11 mg, 58%). Compounds 19b-19o were synthesized similarly as compound 19a.

1-Benzyl-N$^{6,2}$-dibutyl-1H-imidazo[4,5-c]pyridine-4,6-diamine (19b)

Butyl amine was used as a reagent to obtain a brown solid (23 mg, 79%).

1-Benzyl-2-butyl-N⁶-heptyl-N⁴-(2,4,4-trimethylpentan-2-yl)-1H-imidazo[4,5-c]pyridine-4,6-diamine (18c)

Heptylamine was used as a reagent to obtain a brown oil (43 mg, 65%).

1-Benzyl-2-butyl-N⁶-heptyl-1H-imidazo[4,5-c]pyridine-4,6-diamine (19c)

Light brown solid (24 mg, 80%).

1-Benzyl-2-butyl-N⁶-(cyclohexylmethyl)-N-(2,4,4-trimethylpentan-2-yl)-1H-imidazo[4,5-c]pyridine-4,6-diamine (18d)

N-Cyclohexylmethylamine was used as a reagent to obtain yellow solid (50 mg, 62%).

1-Benzyl-2-butyl-N-(cyclohexylmethyl)-1H-imidazo[4,5-c]pyridine-4,6-diamine (19d)

Light brown (28 mg, 80%).

1-Benzyl-2-butyl-N⁶-phenyl-N⁴-(2,4,4-trimethylpentan-2-yl)-1H-imidazo[4,5-c]pyridine-4,6-diamine (18e)

Aniline was used as a reagent to obtain yellow solid (51 mg, 55%).

1-Benzyl-2-butyl-N⁶-phenyl-1H-imidazo[4,5-c]pyridine-4,6-diamine (19e)

Light yellow solid (28 mg, 76%).

N⁶,¹-Dibenzyl-2-butyl-N⁴-(2,4,4-trimethylpentan-2-yl)-1H-imidazo[4,5-c]pyridine-4,6-diamine (18f)

Benzyl amine was used as a reagent to obtain light brown solid (30 mg, 46%).

N⁶,¹-Dibenzyl-2-butyl-1H-imidazo[4,5-c]pyridine-4,6-diamine (19f)

White solid (22 mg, 85%).

1-Benzyl-2-butyl-N-(4-methoxybenzyl)-1H-imidazo[4,5-c]pyridine-4,6-diamine (19g)

4-Methoxybenzyl amine was used as a reagent to obtain light yellow solid (22 mg, 69%).

1-Benzyl-2-butyl-N⁶-(3-methoxybenzyl)-1H-imidazo[4,5-c]pyridine-4,6-diamine (19h)

3-Methoxybenzyl amine was used as a reagent to obtain brown solid (27 mg, 69%).

1-Benzyl-2-butyl-N⁶-(4-(trifluoromethyl)benzyl)-1H-imidazo[4,5-c]pyridine-4,6-diamine (19i)

4-(Trifluoromethyl)benzyl amine was used as a reagent to obtain brown solid (17 mg, 77%).

1-Benzyl-2-butyl-N⁶-(4-chlorobenzyl)-1H-imidazo[4,5-c]pyridine-4,6-diamine (19j)

4-Chlorobenzylamine was used as a reagent to obtain yellow solid (15 mg, 63%).

1-Benzyl-2-butyl-N⁶-(furan-2-ylmethyl)-N⁴-(2,4,4-trimethylpentan-2-yl)-1H-imidazo[4,5-c]pyridine-4,6-diamine (18k)

Furfuryl amine was used as a reagent to obtain yellow oil (53 mg, 54%).

1-Benzyl-2-butyl-N⁶-(furan-2-ylmethyl)-1H-imidazo[4,5-c]pyridine-4,6-diamine (19k)

Brown solid (21 mg, 55%).

1-Benzyl-2-butyl-N⁶-(pyridin-4-ylmethyl)-N⁴-(2,4,4-trimethyl pentan-2-yl)-1H-imidazo[4,5-c]pyridine-4,6-diamine (18l)

4-Picolylamine was used as a reagent to obtain yellow solid (25 mg, 31%).

1-Benzyl-2-butyl-N⁶-(pyridin-4-ylmethyl)-1H-imidazo[4,5-c]pyridine-4,6-diamine (19l)

Brown solid (7 mg, 47%).

1-Benzyl-2-butyl-N-(pyridin-3-ylmethyl)-1H-imidazo[4,5-c]pyridine-4,6-diamine (19m)

3-Picolylamine was used as a reagent to obtain light brown solid (33 mg, 63%).

1-Benzyl-2-butyl-N⁶-(naphthalen-1-ylmethyl)-1H-imidazo[4,5-c]pyridine-4,6-diamine (19n)

1-Naphthylmethylamine was used as a reagent to obtain light brown solid (28 mg, 70%).

N⁶-([1,1'-Biphenyl]-4-ylmethyl)-1-benzyl-2-butyl-1H-imidazo[4,5-c]pyridine-4,6-diamine (19o)

[1,1'-biphenyl]-4-yl methane amine was used as a reagent to obtain light brown solid (21 mg, 51%).

Synthesis of Compound 19p and 19r: N⁶-(4-(aminomethyl) benzyl)-1-benzyl-2-butyl-1H-imidazo[4,5-c]pyridine-4,6-diamine To a solution of compound 16 (70 mg, 0.16 mmol) in 1 mL of dioxane were added potassium tert-butoxide (90 mg, 0.80 mmol), catalytic amount of DavePhos and Pd₂(dba)₃ and p-xylylenediamine (109 mg, 0.80 mmol). The reaction mixture was then heated under microwave conditions (500 W, 100° C.) in a sealed vial for 1 h. It was cooled to room temperature and filtered through celite and washed with MeOH. The solvent was removed and the crude residue was purified using column chromatography (20% EtOAc/hexane) to obtain the compound 18p and 18r. Compound 18p (33 mg, 0.063 mmol) was dissolved in 1 mL of HCl (4M in dioxane) and stirred at room temperature for 30 min. Then the solvent was removed under vacuum to obtain compound 19p as light yellow solid (5 mg, 63%).

$N^6,N^{6'}$-(1,4-phenylenebis(methylene))bis(1-benzyl-2-butyl-1H-imidazo[4,5-c]pyridine-4,6-diamine) (19r)

Compound 18r (35 mg, 0.038 mmol) was dissolved in 1 mL of HCl (4M in dioxane) and stirred at room temperature for 30 min. Then the solvent was removed under vacuum to obtain compound 19r as light yellow solid (12 mg, 45%). Compounds 19q and 19s were synthesized similarly as compounds 19p and 19r.

$N^6$-(3-(aminomethyl)benzyl)-1-benzyl-2-butyl-1H-imidazo[4,5-c]pyridine-4,6-diamine (19q)

m-xylylenediamine was used as a reagent to obtain light yellow solid.

$N^6,N^{6'}$-(1,3-phenylenebis(methylene))bis(1-benzyl-2-butyl-1H-imidazo[4,5-c]pyridine-4,6-diamine) (19s)

Light yellow solid.

Synthesis of Compound 23a

To a solution of compound 14 (120 mg, 0.31 mmol) in 1 mL of dioxane were added cesium carbonate (303 mg, 0.93 mmol) in $H_2O$ (0.5 mL), [1,1'-bis(diphenylphosphino)ferrocene]dichloropalladium(II) (Pd(dppf)Cl$_2$) (15 mg, 0.019 mmol) and n-butylboronic acid (98 μL, 0.46 mmol) under $N_2$. The reaction mixture was then heated at 90° C. in a sealed vial for 18 h. It was cooled to room temperature and filtered through celite and washed with MeOH. The solvent was removed and the crude residue was purified using column chromatography (15% EtOAc/hexane) to obtain the compound 20a (97 mg, 76%). To a solution of compound 20a (94 mg, 0.23 mmol) in 10 mL of MeOH were added zinc dust (149 mg, 2.30 mmol) and ammonium formate (145 mg, 2.30 mmol). The reaction mixture was stirred at room temperature for 10 min and filtered through celite. Then the solvent was evaporated and the residue was dissolved in water. This was extracted with EtOAc (3×20 mL), washed with water and dried over sodium sulfate. The solvent was removed under vacuum to obtain compound 21a (45 mg, 51%). To a solution of compound 21a (42 mg, 0.11 mmol) in 7 mL of anhydrous THF were added triethylamine (16 μL, 0.12 mmol) and valeryl chloride (13 μL, 0.11 mmol). The reaction mixture was refluxed for 1 h. The solvent was then removed under vacuum, and the residue was dissolved in 5 mL of EtOH and NaOH (10 mg, 0.22 mmol) in 1 mL of $H_2O$ was added. The reaction mixture was refluxed for 18 h. The solvent was then removed under vacuum, and the residue was dissolved in EtOAc and washed with water. The EtOAc fraction was dried using sodium sulfate and evaporated and purified using column chromatography (20% EtOAc/hexane) to obtain the compound 22a (25 mg, 51%). Compound 22a (22 mg, 0.049 mmol) was dissolved in 1 mL of HCl (4M in dioxane) and stirred at room temperature for 30 min. Then the solvent was removed under vacuum to obtain compound 23a (11 mg, 69%).

$N^4$-Benzyl-6-butyl-3-nitro-N-(2,4,4-trimethylpentan-2-yl)pyridine-2,4-damine (20a)

Yellow oil (97 mg, 76%).

1-Benzyl-2,6-dibutyl-1H-imidazo[4,5-c]pyridin-4-amine (23a). White solid (11 mg, 69%)

Compounds 23b-23j were synthesized similarly as compound 23a.

$N^4$-Benzyl-3-nitro-6-phenyl-$N^2$-(2,4,4-trimethylpentan-2-yl)pyridine-2,4-damine (20b)

Phenylboronic acid was used as a reagent to obtain yellow solid (28 mg, 57%).

1-Benzyl-2-butyl-6-phenyl-N-(2,4,4-trimethylpentan-2-yl)-1H-imidazo[4,5-c]pyridin-4-amine (22b)

Yellow solid (31 mg, 47%).

1-Benzyl-2-butyl-6-phenyl-1H-imidazo[4,5-c]pyridin-4-amine (23b)

White solid (13 mg, 73%).

4-(4-(Benzylamino)-5-nitro-6-((2,4,4-trimethylpentan-2-yl)amino)pyridin-2-yl)benzonitrile (20c)

4-Cyanophenylboronic acid was used as a reagent to obtain yellow solid (30 mg, 55%).

4-(1-Benzyl-2-butyl-4-((2,4,4-trimethylpentan-2-yl)amino)-1H-imidazo[4,5-c]pyridin-6-yl)benzamide (22c)

Cyano group was converted into amide in the basic condition. Yellow solid (22 mg, 41%).

4-(4-Amino-1-benzyl-2-butyl-1H-imidazo[4,5-c]pyridin-6-yl)benzamide (23c)

White solid (11 mg, 79%).

$N^4$-Benzyl-5-nitro-$N^6$-(2,4,4-trimethylpentan-2-yl)-[2,3'-bipyridine]-4,6-diamine (20d)

4-Pyridinylboronic acid was used as a reagent. Orange solid (135 mg, 82%).

1-Benzyl-2-butyl-6-(pyridin-3-yl)-1H-imidazo[4,5-c]pyridin-4-amine (23d)

Light yellow solid (10 mg, 72%).

$N^4$-Benzyl-6-(furan-3-yl)-3-nitro-N-(2,4,4-trimethylpentan-2-yl)pyridine-2,4-diamine (20e)

3-Furylboronic acid was used as a reagent. Yellow solid (95 mg, 70%).

1-Benzyl-2-butyl-6-(furan-3-yl)-N-(2,4,4-trimethylpentan-2-yl)-1H-imidazo[4,5-c]pyridin-4-amine (22e)

Brown oil (30 mg, 41%).

1-Benzyl-2-butyl-6-(furan-3-yl)-1H-imidazo[4,5-c]pyridin-4-amine (23e)

Light yellow solid (12 mg, 64%).

N⁴-Benzyl-3-nitro-6-(thiophen-3-yl)-N-(2,4,4-trimethylpentan-2-yl)pyridine-2,4-diamine (20f)

3-Thienylboronic acid was used as a reagent. Yellow solid (107 mg, 76%).

1-Benzyl-2-butyl-6-(thiophen-3-yl)-N-(2,4,4-trimethylpentan-2-yl)-1H-imidazo[4,5-c]pyridin-4-amine (22f)

Brown solid (25 mg, 35%).

1-Benzyl-2-butyl-6-(thiophen-3-yl)-1H-imidazo[4,5-c]pyridin-4-amine (23f)

White solid (9 mg, 53%).

N$^{4,6}$-Dibenzyl-3-nitro-N-(2,4,4-trimethylpentan-2-yl)pyridine-2,4-diamine (20g)

Benzylboronic acid pinacol ester was used as a reagent. Orange oil (135 mg, 91%).

1,6-Dibenzyl-2-butyl-N-(2,4,4-trimethylpentan-2-yl)-1H-imidazo[4,5-c]pyridin-4-amine (22g)

Light brown solid (55 mg, 60%).

1,6-Dibenzyl-2-butyl-1H-imidazo[4,5-c]pyridin-4-amine (23g)

White solid (23 mg, 58%).

N⁴-Benzyl-6-(4-methylbenzyl)-3-nitro-N²-(2,4,4-trimethylpentan-2-yl)pyridine-2,4-diamine (20h)

4-Methyl benzylboronic acid pinacol ester was used as a reagent. Yellow oil (130 mg, 91%).

1-Benzyl-2-butyl-6-(4-methylbenzyl)-1H-imidazo[4,5-c]pyridin-4-amine (23h)

White solid (19 mg, 66%).

N⁴-Benzyl-3-nitro-6-(4-(trifluoromethoxy)benzyl)-N-(2,4,4-trimethylpentan-2-yl)pyridine-2,4-diamine (20i)

4-(Trifluoromethoxy)benzylboronic acid pinacol ester was used as a reagent. Yellow solid (115 mg, 70%).

1-Benzyl-2-butyl-6-(4-(trifluoromethoxy)benzyl)-1H-imidazo[4,5-c]pyridin-4-amine (23i)

White solid (21 mg, 47%).

N⁴-Benzyl-3-nitro-6-phenethyl-N²-(2,4,4-trimethylpentan-2-yl)pyridine-2,4-diamine (20j)

2-Phenylethylboronic acid was used as a reagent. Yellow oil (85 mg, 59%).

1-Benzyl-2-butyl-6-phenethyl-1H-imidazo[4,5-c]pyridin-4-amine (23j)

Yellow solid (11 mg, 42%).

Synthesis of Compound 24: 3-Nitrobenzo[g]quinolin-4-ol

Nitromethane (0.96 mL, 18 mmol) was added dropwise to a solution of NaOH (2.2 g, 54 mmol) in water (5 mL), at 0° C. The mixture was then warmed to 40° C. and nitromethane (0.96 mL, 18 mmol) was again added slowly at 40-45° C. The temperature was maintained until a clear solution was obtained. The reaction mixture was then heated to 55° C. for 2-5 minutes, cooled to 30° C., poured onto crushed ice and acidified with conc. HCl (5 mL). The resultant solution of methazoic acid was added immediately to a filtered solution of 3-amino-2-naphtholic acid (3 g, 16 mmol) and conc. HCl (1 mL) in water (20 mL). The reaction mixture was allowed to stand at room temperature for 12 h. After filtration, the residue obtained was washed with water, and dried (1.1 g, 90%). A solution of intermediate (2 g, 7.75 mmol) in acetic anhydride (10 mL) was placed in a 2-neck flask fitted with a reflux condenser. It was stirred and heated to 105° C. until a clear solution was obtained. Heating was then discontinued and potassium acetate (0.77 g, 7.90 mmol) was added. The mixture was then refluxed for 15 min with vigorous stirring, until a solid started to precipitate. The reaction mixture was then slowly cooled to room temperature. The residue was filtered, washed with glacial acetic acid until the washings were colorless, then suspended in water, filtered, washed with water and dried at 110° C. to get compound 24 (0.93 g, 50%).

Synthesis of Compound 25: 4-Chloro-3-nitrobenzo[g]quinoline

A suspension of compound 24 (2.0 g, 8.30 mmol) in phosphorus(V) oxychloride was placed in a pressure vessel and it was heated at 150° C. After a clear solution was obtained, the reaction mixture was kept at 150° C. for 1 h. Then it was slowly cooled to room temperature and the solvent was evaporated under vacuum. The residue was poured over crushed ice while stirring and the formed solid was filtered, washed with water and dried to obtain compound 25 (1.95 g, 91%).

Synthesis of Compound 26: N-Benzyl-3-nitrobenzo[g]quinolin-4-amine

To a solution of compound 25 (1.0 g, 3.90 mol) in 20 mL of CH$_2$Cl$_2$ was added triethylamine (0.81 mL, 5.80 mmol) and benzylamine (0.50 mL, 4.60 mmol). The reaction mixture was refluxed for 2 h. The solvent was then evaporated under vacuum and H$_2$O was added to the residue. The solution was extracted with CH$_2$Cl$_2$ (3×20 mL), washed with water and dried over sodium sulfate. The solvent was evaporated and the residue was purified using silica gel column chromatography (5% MeOH/CH$_2$Cl$_2$) to obtain compound 26 as a yellow solid (1.1 g, 88%).

Synthesis of Compound 30: 1-Benzyl-2-butyl-1H-benzo[g]imidazo[4,5-c]quinolin-4-amine To a solution of compound 26 (300 mg, 0.91 mmol) in 20 mL of MeOH were added zinc dust (594 mg, 9.10 mmol) and ammonium formate (574 mg, 9.10 mmol). The reaction mixture was stirred at room temperature for 30 min and filtered through celite. Then the solvent was evaporated and the residue was dissolved in water. This was extracted with EtOAc (3×20 mL), washed with water and dried over sodium sulfate. The solvent was removed under vacuum to obtain compound 27 (100 mg, 37%). To a solution of compound 27 (98 mg, 0.33 mmol) in 10 mL of anhydrous THF were added triethylamine (48 µL, 0.35 mmol) and valeryl chloride (40 µL, 0.33 mmol). The reaction mixture was refluxed for 2 h. The solvent was then removed under vacuum, and the residue was dissolved in 10 mL of EtOH and NaOH (26 mg, 0.66 mmol) in 1 mL of $H_2O$ was added. The reaction mixture was refluxed for 2 h. The solvent was then removed under vacuum, and the residue was dissolved in EtOAc and washed with water. The EtOAc fraction was dried using sodium sulfate and evaporated and purified using column chromatography (10% $MeOH/CH_2Cl_2$) to obtain the compound 28 (76 mg, 63%). To a solution of compound 28 (76 mg, 0.21 mmol) in a solvent mixture of $MeOH:CH_2C2:CHCl_3$ (1:10:10) was added 3-chloroperoxy benzoic acid (443 mg, 1.98 mmol), and the solution was refluxed at 45-50° C. for 1 h. The solvent was then removed and the residue was purified using column chromatography (10% $MeOH/CH_2Cl_2$) to obtain the N-oxide derivative 29 (64 mg, 80%). To a solution of compound 29 (64 mg, 0.17 mol) in 10 mL of $CH_2Cl_2$ was added benzoyl isocyanate (37 mg, 0.25 mmol) and heated at 45° C. for 18 h. The solvent was then removed under vacuum, and the residue was dissolved in 15 mL of anhydrous MeOH, followed by the addition of excess sodium methoxide. The reaction mixture was then heated at 80° C. for 2 h. The solvent was removed under vacuum and the residue was purified using column chromatography (10% $MeOH/CH_2Cl_2$) to obtain the compound 30 (20 mg, 30%).

Human TLR-7/-8 Reporter Gene Assays (NF-κB Induction).

The induction of NF-κB was quantified using HEK-Blue-7 (hTLR7-specific) and HEK-Blue-8 (hTLR8-specific) cells. HEK293 cells stably co-transfected with human TLR7 or human TLR8, MD2, and secreted alkaline phosphatase (sAP), were maintained in HEK-Blue™ Selection medium containing zeocin and normocin. Stable expression of secreted alkaline phosphatase (sAP) under control of NF-κB/AP-1 promoters is inducible by appropriate TLR agonists, and extracellular sAP in the supernatant is proportional to NF-κB induction. HEK-Blue cells were incubated at a density of ~$10^5$ cells/ml in a volume of 80 µl/well, in 384-well, flat-bottomed, cell culture-treated microtiter plates until confluency was achieved, and subsequently stimulated with graded concentrations of stimuli. sAP was assayed spectrophotometrically using an alkaline phosphatase-specific chromogen (present in HEK-detection medium as supplied by the vendor) at 620 nm.

Immunoassays for Interferon (IFN)-α, and Cytokines.

Fresh human peripheral blood mononuclear cells (hPBMC) were isolated from human blood obtained by venipuncture with informed consent and as per institutional guidelines on Ficoll-Hypaque gradients as described elsewhere. Aliquots of PBMCs ($10^5$ cells in 100 µL/well) were stimulated for 12 h with graded concentrations of test compounds. Supernatants were isolated by centrifugation, and were assayed in triplicates using either high-sensitivity multi-subtype IFN-α ELISA kits (PBL Interferon Source, Piscataway, N.J. and R&D Systems, Inc., Minneapolis, Minn.), or analyte-specific multiplexed cytokine/chemokine bead array assays as reported by us previously.

Flow-Cytometric Immunostimulation Experiments.

CD69 upregulation was determined by flow cytometry and modified for rapid-throughput. Briefly, heparin-anticoagulated whole blood samples were obtained by venipuncture from healthy human volunteers with informed consent and as per guidelines approved by the University of Kansas Human Subjects Experimentation Committee. Serial dilutions of selected imidazopyridine compounds (and imiquimod, used as a reference compound) were performed using a Bio-Tek Precision 2000 XS liquid handler in sterile 96-well polypropylene plates, to which were added 100 µL aliquots of anticoagulated whole human blood. The plates were incubated at 37° C. for 16.5 h. Negative (endotoxin free water) controls were included in each experiment. Following incubation, fluorochrome-conjugated antibodies (CD3-PE, CD56-APC, CD69-PE-Cy7, 10 µL of each antibody, Becton-Dickinson Biosciences, San Jose, Calif.) were added to each well with a liquid handler, and incubated at 37° C. in the dark for 30 min. Following staining, erythrocytes were lysed and leukocytes fixed by mixing 200 L of the samples in 2 mL pre-warmed Whole Blood Lyse/Fix Buffer (Becton-Dickinson Biosciences, San Jose, Calif.) in 96 deep-well plates. After washing the cells twice at 200 g for 8 minutes in saline, the cells were transferred to a 96-well plate. Flow cytometry was performed using a BD FACSArray instrument in the tri-color mode (tri-color flow experiment) and two-color mode (two-color flow experiment) for acquisition on 100,000 gated events. Compensation for spillover was computed for each experiment on singly-stained samples. CD69 activation in the major lymphocytic populations, viz., natural killer lymphocytes (NK cells: $CD3^-CD56^+$), cytokine-induced killer phenotype (CIK cells: $CD3^+CD56^+$), nominal B lymphocytes ($CD3^-CD56^-$), and nominal T lymphocytes ($CD3^+CD56^-$) were quantified using FlowJo v 7.0 software (Treestar, Ashland, Oreg.).

A lead compound for TLR7 agonism can be compound 19p. Its substituents are such that it becomes a substrate for metabolism (e.g., monoamine oxidase and Cyp450 enzymes, for instance). Surprisingly and unexpectedly even fibroblasts metabolize compound 19p rapidly and extensively. In one aspect, compound 19p may be omitted for use as an adjuvant. However, the very evanescence is a vaunted property when one designs drugs for allergic bronchitis and bronchospastic disorders associated with atopy or allergy. As such, a method of the invention may include using compound 19p in a treatment for allergic bronchitis and/or bronchospastic disorder, such as when associated with atopy or allergy.

TLR8

Chemistry.

All of the solvents and reagents used were obtained commercially and used as such unless noted otherwise. Moisture- or air-sensitive reactions were conducted under nitrogen atmosphere in oven-dried (120° C.) glass apparatus. Solvents were removed under reduced pressure using standard rotary evaporators. Flash column chromatography was carried out using RediSep Rf 'Gold' high performance silica columns on CombiFlash $R_f$ instruments unless otherwise mentioned, while thin-layer chromatography was carried out on silica gel CCM pre-coated aluminum sheets. Purity for all final compounds was confirmed to be greater than 98% by LC-MS using a Zorbax Eclipse Plus 4.6 mm×150 mm, 5 µm analytical reverse phase $C_{18}$ column with $H_2O$—$CH_3CN$ and $H_2O$-MeOH gradients and an Agilent 6520 ESI-QTOF Accurate Mass spectrometer (mass accuracy of 5 ppm) operating in the positive ion acquisition mode.

Synthesis of 2-(2-nitrophenyl)hexanenitrile (Compound A2)

To a solution of 2-nitrophenylacetonitrile (162 mg, 1 mmol) in anhydrous DMSO (5 mL) was added $K_2CO_3$ (152 mg, 1.1 mmol) and the reaction mixture was stirred for 10 min under nitrogen atmosphere. Butyl iodide (125 µL, 1.1 mmol) was added to the reaction mixture and the stirring was continued for 3 h. Water was added to the reaction mixture and it was extracted with EtOAc (3×20 mL). The combined organic layer was dried over $Na_2SO_4$, concentrated under reduced pressure, and the crude material was purified by silica gel column chromatography (10% EtOAc/hexanes) to afford compound A2 as a pale yellow oil (174 mg, 80%). $R_f$=0.50 (10% EtOAc/hexanes).

Synthesis of 2-(2-aminophenyl)hexanenitrile (Compound A3)

To a solution of compound A2 (109 mg, 0.5 mmol) in anhydrous EtOAc (10 mL) was added a catalytic amount of Pt/C (39 mg, 1 mol %), and the reaction mixture was subjected to hydrogenation at 30 psi hydrogen pressure for 3 h. The reaction mixture was filtered, and the filtrate concentrated under reduced pressure. The crude material was purified using silica gel column chromatography (10% MeOH/$CH_2Cl_2$) to obtain compound A3 as a pale yellow oil (70 mg, 74%). $R_f$=0.40 (10% MeOH/$CH_2Cl_2$).

Synthesis of 2-amino-3-butyl-3H-indol-3-ol (Compound A5)

To a solution of compound A3 (38 mg, 0.2 mmol) in anhydrous dioxane (1 mL) was added 4N HCl/dioxane (0.1 mL). The reaction mixture was then heated under microwave conditions (400 W, 100° C.) in a sealed vial for 20 min. The reaction mixture was cooled to room temperature and the solvent was removed under reduced pressure to obtain the compound A4. To a solution of compound A4 in MeOH (1 mL) was added $Et_3N$ (56 µL, 0.4 mmol). The reaction mixture was then stirred for 3 h. The solvent was removed under reduced pressure and the crude material was purified using silica gel column chromatography (20% MeOH/$CH_2Cl_2$) to obtain the compound A5 as white solid (23 mg, 56%). $R_f$=0.30 (20% MeOH/$CH_2Cl_2$).

Synthesis of 2-aminobenzimidazole (Compound A7)

To a solution of compound o-phenylenediamine (108 mg, 1 mmol) in 1:1 mixture of MeOH (5 mL) and water (5 mL) was added CNBr (318 mg, 3 mmol). The reaction mixture was stirred for 3 h at 60° C. The reaction mixture was cooled to room temperature; the MeOH was removed under reduced pressure, and the remaining mixture was basified with 1.0 M aq. NaOH (to pH=8.0) and extracted with EtOAc (3×30 mL). The combined organic layer was dried over $Na_2SO_4$, concentrated under reduced pressure, and the crude material was purified by silica gel column chromatography (20% MeOH/$CH_2Cl_2$) to obtain the compound A7 as a white solid (109 mg, 82%). $R_f$=0.20 (20% MeOH/$CH_2C2$).

Synthesis of 1-butyl-1H-benz[d]imidazol-2-amine (Compound A8a)

To a solution of 2-aminobenzimidazole (compound A7) (27 mg, 0.2 mmol) in acetone (1 mL) were added KOH (22 mg, 0.4 mmol) and butyl iodide (23 µL, 0.2 mmol). The reaction mixture was stirred for 3 h at 60° C. The reaction mixture was cooled to room temperature and the solvent was removed under reduced pressure. The reaction mixture was diluted with water and extracted with EtOAc (3×10 mL). The combined organic layer was dried over $Na_2SO_4$, concentrated under reduced pressure, and the crude material was purified by silica gel column chromatography (20% MeOH/$CH_2Cl_2$) to obtain the compound A8a as a white solid (28 mg, 74%). $R_f$=0.45 (20% MeOH/$CH_2Cl_2$). Compounds A8b-A8e were synthesized similarly as compound A8a.

1-Pentyl-1H-benzo[d]imidazol-2-amine (Compound A8b)

1-Iodopentane was used as reagent. White solid (25 mg, 61%). $R_f$=0.50 (20% MeOH/$CH_2Cl_2$).

1-Hexyl-1H-benzo[d]imidazol-2-amine (Compound A8c)

1-Iodohexane was used as reagent. White solid (30 mg, 69%). $R_f$=0.52 (20% MeOH/$CH_2Cl_2$).

1-Benzyl-1H-benzo[d]imidazol-2-amine (Compound A8d)

Benzyl bromide was used as reagent. White solid (28 mg, 63%). $R_f$=0.44 (10% 20% MeOH/$CH_2Cl_2$).

3-((2-amino-1H-benzo[d]imidazol-1-yl)methyl)benzonitrile (Compound A8e)

3-Cyanobenzyl bromide was used as reagent. White solid (38 mg, 76%). $R_f$=0.40 (20% MeOH/$CH_2Cl_2$).

Synthesis of 1-(3-(aminomethyl)benzyl)-1H-benzo [d]imidazol-2-amine (Compound A8f)

To a solution of compound A8e (25 mg, 0.1 mmol) in THF (2 mL) was added $LiAlH_4$ (0.4 mL, 0.4 mmol, 1.0 M in THF) at 0° C. under nitrogen atmosphere. The reaction mixture was stirred for 1 h at 25° C. and 5 h at 75° C. The reaction mixture was cooled to room temperature and quenched carefully with ice-cold water. The resulting mixture was basified with 10% NaOH (to pH=8.0) and extracted with $CH_2Cl_2$ (3×10 mL). The combined organic layer was dried over $Na_2SO_4$, concentrated under reduced pressure, and the crude material was purified by neutral-alumina column chromatography (30% MeOH/$CH_2Cl_2$) to obtain the compound A8f as a white solid (17 mg, 67%). $R_f$=0.20 (40% MeOH/$CH_2Cl_2$).

Synthesis of butyl 2-amino-1H-benzo[d]imidazole-1-carboxylate (Compound A9)

To a solution of 2-aminobenzimidazole (compound A7) (27 mg, 0.2 mmol) in anhydrous THF (2 mL) was added butyl chloroformate (27 µL, 0.2 mmol) under nitrogen atmosphere. The reaction mixture was stirred for 3 h. The reaction mixture was diluted with water and extracted with EtOAc (3×10 mL). The combined organic layer was dried over $Na_2SO_4$, concentrated under reduced pressure, and the crude material was purified by silica gel column chromatography (20% MeOH/$CH_2Cl_2$) to afford the compound A9 as a white solid (28 mg, 60%). $R_f$=0.65 (10% MeOH/$CH_2Cl_2$).

Synthesis of N-(1-pentyl-1H-benzo[d]imidazol-2-yl) acetamide (Compound A10)

To a stirred solution of compound A8b (41 mg, 0.2 mmol) in pyridine (2 mL) was added acetyl chloride (14 µL, 0.2 mmol). The reaction mixture was stirred for 3 h. The solvent was removed under reduced pressure. The reaction mixture was diluted with water and extracted with EtOAc (3×10 mL). The combined organic layer was dried over $Na_2SO_4$, concentrated under reduced pressure, and the crude material was purified by silica gel column chromatography (10% MeOH/$CH_2Cl_2$) to afford the compound A10 as a white solid (32 mg, 65%). $R_f$=0.62 (10% MeOH/$CH_2C2$).

1H-Naphtho[2,3-d]imidazol-2-amine (Compound A12)

Compound A12 was synthesized similarly as compound A7. Naphthalene-2,3-diamine was used as reagent. Off-white solid (135 mg, 74%). $R_f$=0.35 (20% MeOH/$CH_2Cl_2$).

1-Pentyl-1H-naphtho[2,3-d]imidazol-2-amine (Compound A13)

Compound A13 was synthesized similarly as compound A8a. Compound A12 was used as reagent. Off-white solid (40 mg, 79%). $R_f$=0.45 (10% MeOH/$CH_2Cl_2$).

Synthesis of 1-methoxy-2-nitronaphthalene (Compound A15)

To a solution of compound 2-Nitro-1-naphthol (189 mg, 1 mmol) in acetone (5 mL) were added KOH (168 mg, 3 mmol) and MeI (124 µL, 2 mmol). The reaction mixture was refluxed for 12 h. The reaction mixture was cooled to room temperature and solvent was removed under reduced pressure. Water was then added to the reaction mixture and extracted with EtOAc (3×30 mL). The combined organic layer was dried over $Na_2SO_4$, concentrated under reduced pressure, and the crude material was purified by silica gel column chromatography (10% EtOAc/hexanes) to obtain the compound A15 as a pale yellow solid (178 mg, 88%). $R_f$=0.50 (10% EtOAc/hexanes).

Synthesis of 2-nitro-N-pentylnaphthalen-1-amine (Compound A16)

To a solution of compound A15 (102 mg, 0.5 mmol) in DMF (3 mL), was added amyl amine (87 µL, 0.75 mmol). The reaction mixture was stirred for 10 h at 60° C. The reaction mixture was diluted with water and extracted with EtOAc (3×20 mL). The combined organic layer was dried over $Na_2SO_4$, concentrated under reduced pressure, and the crude material was purified by silica gel column chromatography (10% EtOAc/hexanes) to obtain the compound A16 as a red solid (115 mg, 89%). $R_f$=0.62 (10% EtOAc/hexanes).

Synthesis of 1-pentyl-1H-naphtho[1,2-d]imidazol-2-amine (Compound A18)

To a solution of compound A16 (52 mg, 0.2 mmol) in anhydrous EtOAc (5 mL) was added a catalytic amount of 5% Pt on carbon (16 mg, 2 mol %). The reaction mixture was subjected to hydrogenation at 30 psi $H_2$ pressure for 3 h. The reaction mixture was filtered, and the filtrate was concentrated under the reduced pressure to obtain compound A17. To a solution of compound A17 in a 1:1 mixture of MeOH (1 mL) and water (1 mL) was added CNBr (64 mg, 0.6 mmol). The reaction mixture was stirred for 3 h at 60° C. The reaction mixture was cooled to room temperature, and MeOH removed under reduced pressure. The remaining mixture was basified with 1.0 M aq. NaOH (to pH=8.0) and extracted with EtOAc (3×10 mL). The combined organic layer was dried over $Na_2SO_4$, concentrated under reduced pressure, and the crude material was purified by silica gel column chromatography (10% MeOH/$CH_2C2$) to obtain the compound A18 as a purple solid (35 mg, 69%). $R_f$=0.45 (10% MeOH/$CH_2Cl_2$).

2-Methoxy-1-nitronaphthalene (Compound A20)

Compound A20 was synthesized similarly as compound A15. 1-Nitro-2-naphthol was used as reagent. Green solid (164 mg, 81%). $R_f$=0.50 (10% EtOAc/hexanes).

1-Nitro-N-pentylnaphthalen-2-amine (Compound A21)

Compound A21 was synthesized similarly as compound A16. Compound A20 was used as reagent. Orange solid (102 mg, 79%). $R_f$=0.60 (10% EtOAc/hexanes).

3-Pentyl-3H-naphtho[1,2-d]imidazol-2-amine (Compound A23)

Compound A23 was synthesised similarly as compound A18. Compound A21 was used as reagent. Purple solid (37 mg, 73%). $R_f$=0.45 (10% MeOH/$CH_2Cl_2$).

Synthesis of 2-nitro-N-pentylpyridin-3-amine (Compound A25a)

To a solution of compound 3-fluoro-2-nitropyridine (142 mg, 1 mmol) in DMSO (2 mL), were added amyl amine (116 µL, 1 mmol) and DIPEA (174 µL, 1 mmol). The reaction mixture was stirred for 6 h at 60° C. After the completion of the reaction (monitored by TLC), the reaction mixture was diluted with water and extracted with EtOAc (3×20 mL). The combined organic layer was dried over $Na_2SO_4$ and concentrated under reduced pressure, and the crude material was purified by flash chromatography (10% EtOAc/hexanes) to afford the compound A25a as a yellow oil (184 mg, 88%). $R_f$=0.30 (10% EtOAc/hexanes).

3-Nitro-N-pentylpyridin-4-amine (Compound A25b)

Compounds A25b-A25d and A29a-A29i were synthesized similarly as compound A25a. 4-Chloro-3-nitropyridine was used as reagent. Yellow oil (179 mg, 86%). $R_f$=0.20 (10% EtOAc/hexanes).

4-Nitro-N-pentylpyridin-3-amine (Compound A25c)

3-Fluoro-4-nitropyridine was used as reagent. Yellow solid (184 mg, 88%). $R_f$=0.20 (10% EtOAc/hexanes).

3-Nitro-N-pentylpyridin-2-amine (Compound A25d)

2-Chloro-3-nitropyridine was used as reagent. Yellow oil (188 mg, 90%). $R_f$=0.22 (10% EtOAc/hexanes).

3-Methyl-2-nitro-N-pentylaniline (Compound A29a)

1-Fluoro-3-methyl-2-nitrobenzene was used as reagent. Red oil (200 mg, 90%). $R_f$=0.70 (10% EtOAc/hexanes).

4-Methyl-2-nitro-N-pentylaniline (Compound A29b)

1-Fluoro-4-methyl-2-nitrobenzene was used as reagent. Red oil (180 mg, 81%). $R_f$=0.65 (10% EtOAc/hexanes).

5-Methyl-2-nitro-N-pentylaniline (Compound A29c)

2-Chloro-4-methyl-1-nitrobenzene was used as reagent. Orange solid (180 mg, 81%). $R_f$=0.68 (10% EtOAc/hexanes).

2-Methyl-6-nitro-N-pentylaniline (Compound A29d)

2-Chloro-1-methyl-3-nitrobenzene was used as reagent. Red oil (175 mg, 79%). $R_f$=0.70 (10% EtOAc/hexanes).

3-Methoxy-2-nitro-N-pentylaniline (Compound A29e)

1-Fluoro-3-methoxy-2-nitrobenzene was used as reagent. Red oil (200 mg, 84%). $R_f$=0.62 (10% EtOAc/hexanes).

3-Fluoro-2-nitro-N-pentylaniline (Compound A29f)

1,3-Difluoro-2-nitrobenzene was used as reagent. Red oil (169 mg, 75%). $R_f$=0.62 (5% EtOAc/hexanes).

3-Chloro-2-nitro-N-pentylaniline (Compound 29g)

1-Chloro-3-fluoro-2-nitrobenzene was used as reagent. Orange solid (200 mg, 83%). $R_f$=0.65 (5% EtOAc/hexanes).

2-Nitro-N-pentyl-3-(trifluoromethyl)aniline (Compound A29h)

1-Chloro-2-nitro-3-(trifluoromethyl) benzene was used as reagent. Orange solid (179 mg, 65%). $R_f$=0.70 (5% EtOAc/hexanes).

3-Bromo-2-nitro-N-pentylaniline (Compound A29i)

1-Bromo-3-fluoro-2-nitrobenzene was used as reagent. Orange solid (250 mg, 87%). $R_f$=0.70 (5% EtOAc/hexanes).

Synthesis of 3-ethyl-2-nitro-N-pentylaniline (Compound A29j)

To a stirred solution of compound A29i (144 mg, 0.5 mmol) in 1,4-dioxane (3 mL) were added ethylboronic acid (56 mg, 0.75 mmol), Pd(dppf)Cl$_2$ (36 mg, 0.05 mmol) and K$_2$CO$_3$ (207 mg, 1.5 mmol). The resulting reaction mixture was stirred at 90° C. under nitrogen atmosphere for 12 h. The reaction mixture was diluted with water and extracted with EtOAc (3×20 mL). The combined organic layer was dried over Na$_2$SO$_4$ and concentrated under reduced pressure, crude material was purified by flash chromatography (10% EtOAc/hexanes) to obtain the compound A29j as a red oil (72 mg, 61%). $R_f$=0.70 (10% EtOAc/hexanes).

Synthesis of N,N-Dimethyl-2-nitro-N'-pentyl-benzene-1,3-diamine (Compound A29k)

To a solution of compound A29g (242 mg, 1 mmol) in DMF (3 mL), was added dimethyl amine (2 mL, 4 mmol, 2.0 M in MeOH). The reaction mixture was stirred for 12 h at 75° C. The reaction mixture was cooled to room temperature, diluted with water and extracted with EtOAc (3×30 mL). The combined organic layer was dried over Na$_2$SO$_4$, concentrated under reduced pressure, and the crude material was purified by silica gel column chromatography (10% EtOAc/hexanes) to obtain the compound A29k as a red solid (200 mg, 80%). $R_f$=0.3 (10% EtOAc/hexanes).

1-Pentyl-1H-imidazo[4,5-b]pyridin-2-amine (Compound A27a)

Compounds A27a-A27d and A31a-A31k were synthesized similarly as compound A18. Compound A25a was used as reagent. White solid (29 mg, 71%). $R_f$=0.42 (10% MeOH/CH$_2$Cl$_2$).

1-Pentyl-1H-imidazo[4,5-c]pyridin-2-amine (Compound A27b)

Compound A25b was used as reagent. White solid (29 mg, 71%). $R_f$=0.20 (10% MeOH/CH$_2$Cl$_2$).

3-Pentyl-3H-imidazo[4,5-c]pyridin-2-amine (Compound A27c)

Compound A25c was used as reagent. White solid (30 mg, 74%). $R_f$=0.40 (10% MeOH/CH$_2$Cl$_2$).

3-Pentyl-3H-imidazo[4,5-b]pyridin-2-amine (Compound A27d)

Compound A25d was used as reagent. White solid (34 mg, 83%). $R_f$=0.45 (10% MeOH/CH$_2$Cl$_2$).

4-Methyl-1-pentyl-1H-benzo[d]imidazol-2-amine (Compound A31a)

Compound A29a was used as reagent. White solid (33 mg, 76%). $R_f$=0.50 (10% MeOH/CH$_2$C2).

5-Methyl-1-pentyl-1H-benzo[d]imidazol-2-amine (Compound A3 b)

Compound A29b was used as reagent. White solid (35 mg, 81%). $R_f$=0.47 (10% MeOH/CH$_2$Cl$_2$).

6-Methyl-1-pentyl-1H-benzo[d]imidazol-2-amine (Compound A31c)

Compound A29c was used as reagent. White solid (32 mg, 74%). $R_f$=0.44 (10% MeOH/CH$_2$Cl$_2$).

7-Methyl-1-pentyl-1H-benzo[d]imidazol-2-amine (Compound A31d)

Compound A29d was used as reagent. White solid (30 mg, 69%). $R_f$=0.45 (10% MeOH/CH$_2$Cl$_2$).

4-Methoxy-1-pentyl-1H-benzo[d]imidazol-2-amine (Compound A31e)

Compound A29e was used as reagent. White solid (33 mg, 71%). $R_f$=0.40 (10% MeOH/CH$_2$Cl$_2$).

4-Fluoro-1-pentyl-1H-benzo[d]imidazol-2-amine (Compound A31f)

Compound A29f was used as reagent. White solid (35 mg, 79%). $R_f$=0.50 (10% MeOH/CH$_2$Cl$_2$).

4-Chloro-1-pentyl-1H-benzo[d]imidazol-2-amine (Compound A31g)

Compound A29g was used as reagent. White solid (35 mg, 74%).

1-Pentyl-4-(trifluoromethyl)-1H-benzo[d]imidazol-2-amine (Compound A31h)

Compound A29h was used as a reagent. White solid (38 mg, 70%). $R_f$=0.70 (10% MeOH/$CH_2Cl_2$).

4-Bromo-1-pentyl-1H-benzo[d]imidazol-2-amine (Compound A31i)

Compound A29i was used as reagent. White solid (44 mg, 78%). $R_f$=0.68 (10% MeOH/$CH_2Cl_2$).

4-Ethyl-1-pentyl-1H-benzo[d]imidazol-2-amine (Compound A31j)

Compound A29j was used as reagent. White solid (35 mg, 76%). $R_f$=0.55 (10% MeOH/$CH_2Cl_2$).

$N^4,N^4$-demethyl-1-pentyl-1H-benzo[d]imidazole-2,4-diamine (Compound A31k)

Compound A29k was used as reagent. Off-white solid (36 mg, 73%). $R_f$=0.5 (20% MeOH/$CH_2Cl_2$).

Synthesis of 1-pentyl-4-phenyl-1H-benzo[d]imidazol-2-amine (Compound A31l)

To a stirred solution of compound A31i (56 mg, 0.2 mmol) in 1,4-dioxane (2 mL) were added phenylboronic acid (36 mg, 0.3 mmol), Pd(dppf)$Cl_2$ (15 mg, 0.02 mmol) and $K_2CO_3$ (83 mg, 0.6 mmol). The resulting reaction mixture was stirred at 90° C. under nitrogen atmosphere for 12 h. The reaction mixture was diluted with water and extracted with EtOAc (3×10 mL). The combined organic layer was dried over $Na_2SO_4$ and concentrated under reduced pressure, the crude material was purified by flash chromatography (10% MeOH/$CH_2C2$) to obtain compound A31l as a white solid (40 mg, 71.6%). $R_f$=0.58 (10% MeOH/$CH_2C2$).

Synthesis of 4-benzyl-1-pentyl-1H-benzo[d]imidazol-2-amine (Compound A31m)

To a solution of compound A31 i (56 mg, 0.2 mmol) in THF (1 mL) were added benzylzinc bromide (1.2 mL, 0.6 mmol, 0.5 M in THF) and Pd(dppf)$Cl_2$ (15 mg, 0.02 mmol). The resulting reaction mixture was stirred at 70° C. under nitrogen atmosphere for 12 h. The reaction mixture was diluted with water and extracted with EtOAc (3×10 mL). The combined organic layer was dried over $Na_2SO_4$ and concentrated under reduced pressure. The crude material was purified by flash chromatography (10% MeOH/$CH_2Cl_2$) to obtain the compound A31m as a white solid (44 mg, 75%). $R_f$=0.60 (10% MeOH/$CH_2Cl_2$).

Synthesis of 1-Benzyloxy-3-fluoro-2-nitro-benzene (Compound A32)

To a solution of compound A28f (318 mg, 2 mmol) in DMF (10 mL), were added $K_2CO_3$ (552 mg, 4 mmol) and benzyl alcohol (226 μL, 2.2 mmol). The reaction mixture was stirred for 12 h at 60° C. The reaction mixture was cooled to room temperature, diluted with water and extracted with EtOAc (3×30 mL). The combined organic layer was dried over $Na_2SO_4$, concentrated under reduced pressure, and the crude material was purified by silica gel column chromatography (10% EtOAc/hexanes) to obtain the compound A32 as yellow oil (400 mg, 81%). $R_f$=0.2 (10% EtOAc/hexanes).

(3-Benzyloxy-2-nitro-phenyl)-pentyl-amine (Compound A33)

Compound A33 was synthesized similarly as compound A25a. Compound A32 was used as reagent. Red oil (238 mg, 76%). $R_f$=0.5 (10% EtOAc/hexanes).

4-Benzyloxy-1-pentyl-1H-benzoimidazol-2-ylamine (Compound A35)

Compound A35 was synthesized similarly as compound A18. Compound A33 was used as reagent. White solid (49 mg, 79%). $R_f$=0.5 (10% MeOH/$CH_2C2$).

Synthesis of 2-Amino-1-pentyl-1H-benzoimidazol-4-ol (Compound A36)

To a solution of compound A35 (31 mg, 0.1 mmol) in anhydrous MeOH (5 mL) was added a catalytic amount of 10% Pd on carbon. The reaction mixture was subjected to hydrogenolysis at 30 psi $H_2$ pressure for 3 h. The reaction mixture was filtered, and the filtrate was concentrated under the reduced pressure. The crude material was purified by silica gel column chromatography (20% MeOH/$CH_2Cl_2$) to obtain the compound A36 as an off-white solid (17 mg, 78%). $R_f$=0.4 (20% MeOH/$CH_2Cl_2$).

Synthesis of 3-Nitro-N1-pentyl-benzene-1,2-diamine (Compound A38)

To a solution of compound A37 (153 mg, 1 mmol) in DMF (5 mL) were added $K_2CO_3$ (276 mg, 2 mmol) and 1-iodopentane (143 μL, 1.1 mmol). The reaction mixture was stirred for 12 h at 50° C. The reaction mixture was cooled to room temperature, diluted with water and extracted with EtOAc (3×10 mL). The combined organic layer was dried over $Na_2SO_4$, concentrated under reduced pressure, and the crude material was purified by silica gel column chromatography (5% EtOAc/hexanes) to obtain the compound A38 as a red solid (120 mg, 54%). $R_f$=0.5 (10% EtOAc/hexanes).

Synthesis of 4-Nitro-1-pentyl-1H-benzoimidazol-2-ylamine (Compound A39)

To a solution of compound A38 (45 mg, 0.2 mmol) in 1:1 mixture of MeOH (1 mL) and water (1 mL) was added CNBr (63 mg, 0.6 mmol). The reaction mixture was stirred for 3 h at 60° C. The reaction mixture was cooled to room temperature; the MeOH was removed under reduced pressure, and the remaining mixture was basified with 1.0 M aq. NaOH (to pH=8.0) and extracted with EtOAc (3×20 mL). The combined organic layer was dried over $Na_2SO_4$, concentrated under reduced pressure, and the crude material was purified by silica gel column chromatography (30% EtOAc/

CH$_2$Cl$_2$) to obtain the compound A39 as a yellow solid (40 mg, 81%). R$_f$=0.5 (10% MeOH/CH$_2$Cl$_2$).

Synthesis of
1-Pentyl-1H-benzoimidazole-2,4-diamine
(Compound A40)

To a solution of compound A39 (25 mg, 0.1 mmol) in anhydrous EtOAc (10 mL) was added a catalytic amount of Pt/C, and the reaction mixture was subjected to hydrogenation at 30 psi for 3 h. The reaction mixture was filtered, and the filtrate concentrated under reduced pressure. The crude material was purified using silica gel column chromatography (20% MeOH/CH$_2$C2) to obtain compound A40 as off-white solid (16 mg, 74%). R$_f$=0.3 (20% MeOH/CH$_2$Cl$_2$).

Molecular Modeling and Induced Fit Docking:

Quantum mechanics/molecular mechanics (QM/MM) methods were used for induced fit docking. Correct bond orders were assigned, hydrogen atoms were added to the residues, and formal partial charges were assigned to atoms using OPLS-all atom force field. The docking grid was generated using co-crystallized ligand as grid center. Ligands were modeled in Schrödinger molecular modeling software (Schrödinger, New York, N.Y.) and were minimized to a gradient of 0.001 KCal/MolÅ$^2$. The QM charges for ligands were obtained from Jaguar (Schrödinger), using the 3-21G basis set with the BLYP density functional theory. Initial docking was performed with Glide using 0.5 van der Waals (vdW) radius scaling factor for both ligand and protein. This soft docking procedure was applied to generate diverse docking solutions and top 20 poses for each ligand were retained. Finally, each ligand was re-docked into its corresponding structures and the resulting complexes were ranked according to GlideScore.

Human TLR-2/-3/-4/-5/-7/-8/-9 and NOD-1/-2 Reporter Gene Assays (NF-κB Induction):

The induction of NF-κB was quantified using human TLR-2/3/-4/-5/-7/-8/-9- and NOD-1/NOD-2-specific, rapid-throughput, liquid handler-assisted reporter gene assays. HEK293 cells stably co-transfected with the appropriate hTLR (or NOD) and secreted alkaline phosphatase (sAP) were maintained in HEK-Blue™ Selection medium. Stable expression of secreted alkaline phosphatase (sAP) under control of NF-κB/AP-1 promoters is inducible by appropriate TLR/NOD agonists, and extracellular sAP in the supernatant is proportional to NF-κB induction. Reporter cells were incubated at a density of ~10$^5$ cells/ml in a volume of 80 μl/well, in 384-well, flat-bottomed, cell culture-treated microtiter plates in the presence of graded concentrations of stimuli. sAP was assayed spectrophotometrically using an alkaline phosphatase-specific chromogen (present in HEK-detection medium as supplied by the vendor) at 620 nm. Antagonistic activities were examined by incubating human NOD-1/NOD-2 reporter cells with graded concentrations of test compounds in the presence of 100 ng/mL of C$_{12}$-iE-DAP or 10 μg/mL murabutide (NOD-2).

Immunoassays for Cytokines.
Experiments performed as described above.
Flow-Cytometric Immunostimulation Experiments:
Experiments performed as described above.

Induced-fit docking of compound A31a (Panel A) and compound A13 (Panel B) in human TLR8 superimposed on the bound conformation of 2-propylthiazolo[4,5-c]quinolin-4-amine (coordinates derived from PDB ID: 3W3K). Strong bidentate ionic H bonds are observed between Asp543 of TLR8 and the C2 amine and the N3 atom of compound A31a. The N1-pentyl group shows extensive hydrophobic interactions in the pocket lined by Phe346/Ile403/Gly376 within protomer A, favorable π-π interactions of the phenyl ring of compound A31a and Phe405, and van der Waals interactions between the C4-methyl and the side chain of Val520. The occupancy of the benzologues (e.g., compound A13) in the binding pocket is compromised by unfavorable sterics, forcing the binding of the analogue in an inverted fashion with the consequent loss of the critical H-bond interactions between the C2 amine and Asp543.

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself. In some embodiments, compounds described herein can be used to treat disorders, or inhibit disorders by being an adjuvant of a vaccine.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition. Here, the compounds can be used as adjuvants in a vaccines, and vaccines are used to inhibit prevent disease, and thereby the compounds can be used to prevent diseases. However, it can be clear that the compounds are adjuvants of vaccines and thereby they can be used in processes for inhibiting a disease, such as inhibiting contraction of the disease or disease state.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician. The therapeutically effective amount can be as an adjuvant.

The term "IC$_{50}$" or "EC$_{50}$" refers an amount, concentration, or dosage of a compound that is required for 50% inhibition of a maximal response in an assay that measures such response.

The term "CC$_{50}$" refers an amount, concentration, or dosage of a compound that results in 50% reduction of the viability of a host. In certain embodiments, the CC$_{50}$ of a compound is the amount, concentration, or dosage of the compound that is required to reduce the viability of cells treated with the compound by 50%, in comparison with cells untreated with the compound.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st ed.; Lippincott Williams & Wilkins: Philadelphia, Pa., 2005; *Handbook of Pharmaceutical Excipients,* 6th ed.; Rowe et al., Eds.; The Pharmaceutical Press and the American Pharmaceutical Association: 2009; *Handbook of Pharmaceutical Additives,* 3rd ed.; Ash and Ash Eds.; Gower Publishing Company: 2007; *Pharmaceutical Preformulation and Formulation,* 2nd ed.; Gibson Ed.; CRC Press LLC: Boca Raton, Fla., 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer or an isotopic variant of a compound described herein. The vaccine agent or the compound adjuvant can be an active ingredient or substance.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease. The vaccine agent or the compound adjuvant can be a therapeutic agent or drug as they are used in inducing resistance of a disease.

The term "alkyl" refers to a linear or branched saturated monovalent hydrocarbon radical, wherein the alkyl may optionally be substituted with one or more substituents Q as described herein. For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms). The R groups can include an alkyl group.

The term "alkylene" refers to a linear or branched saturated divalent hydrocarbon radical, wherein the alkylene may optionally be substituted with one or more substituents Q as described herein. For example, $C_{1-6}$ alkylene refers to a linear saturated divalent hydrocarbon radical of 1 to 6 carbon atoms or a branched saturated divalent hydrocarbon radical of 3 to 6 carbon atoms. In certain embodiments, the alkylene is a linear saturated divalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkylene groups are also referred as "lower alkylene." Examples of alkylene groups include, but are not limited to, methylene, ethylene, propylene (including all isomeric forms), n-propylene, isopropylene, butylene (including all isomeric forms), n-butylene, isobutylene, t-butylene, pentylene (including all isomeric forms), and hexylene (including all isomeric forms). The R groups can include an alkylene group. The term alkyl can also generically refer to alkylenes when both ends have radicals.

The term "heteroalkylene" refers to a linear or branched saturated divalent hydrocarbon radical that contains one or more heteroatoms each independently selected from O, S, and N in the hydrocarbon chain. For example, $C_{1-6}$ heteroalkylene refers to a linear saturated divalent hydrocarbon radical of 1 to 6 carbon atoms or a branched saturated divalent hydrocarbon radical of 3 to 6 carbon atoms. In certain embodiments, the heteroalkylene is a linear saturated divalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ heteroalkylene groups are also referred as "lower heteroalkylene." Examples of heteroalkylene groups include, but are not limited to, —CH$_2$O—, —CH$_2$OCH$_2$—, —CH$_2$CH$_2$O—, —CH$_2$NH—, —CH$_2$NHCH$_2$—, —CH$_2$CH$_2$NH—, —CH$_2$S—, —CH$_2$SCH$_2$—, and —CH$_2$CH$_2$S—. In certain embodiments, heteroalkylene may also be optionally substituted with one or more substituents Q as described herein. The R groups can include a heteroalkylene group.

The term "alkenyl" refers to a linear or branched monovalent hydrocarbon radical, which contains one or more, in one embodiment, one to five, in another embodiment, one, carbon-carbon double bond(s). The alkenyl may be optionally substituted with one or more substituents Q as described herein. The term "alkenyl" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl. The R groups can include an alkenyl group. The term alkenyl can also generically refer to alkenylenes when both ends have radicals.

The term "alkenylene" refers to a linear or branched divalent hydrocarbon radical, which contains one or more, in one embodiment, one to five, in another embodiment, one, carbon-carbon double bond(s). The alkenylene may be optionally substituted with one or more substituents Q as described herein. The term "alkenylene" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenylene refers to a linear unsaturated divalent hydrocarbon radical of 2 to 6 carbon atoms or a branched unsaturated divalent hydrocarbon radical of 3 to 6 carbon atoms. In certain embodiments, the alkenylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenylene groups include, but are not limited to, ethenylene, allylene, propenylene, butenylene, and 4-methylbutenylene. The R groups can include an alkenylene group.

The term "heteroalkenylene" refers to a linear or branched divalent hydrocarbon radical, which contains one or more, in one embodiment, one to five, in another embodiment, one, carbon-carbon double bond(s), and which contains one or more heteroatoms each independently selected from O, S, and N in the hydrocarbon chain. The heteroalkenylene may be optionally substituted with one or more substituents Q as described herein. The term "heteroalkenylene" embraces radicals having a "cis" or "trans" configuration or a mixture thereof, or alternatively, a "Z" or "E" configuration or a mixture thereof, as appreciated by those of ordinary skill in the art. For example, $C_{2-6}$ heteroalkenylene refers to a linear unsaturated divalent hydrocarbon radical of 2 to 6 carbon atoms or a branched unsaturated divalent hydrocarbon radical of 3 to 6 carbon atoms. In certain embodiments, the heteroalkenylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of heteroalkenylene groups include, but are not limited to, —CH=CHO—, —CH=CHOCH$_2$—, —CH=CHCH$_2$O—, —CH=CHS—, —CH=CHSCH$_2$—, —CH=CHCH$_2$S—, or CH=CHCH$_2$NH—. The R groups can include a heteroalkenylene group.

The term "alkynyl" refers to a linear or branched monovalent hydrocarbon radical, which contains one or more, in one embodiment, one to five, in another embodiment, one, carbon-carbon triple bond(s). The alkynyl may be optionally substituted with one or more substituents Q as described herein. For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynyl groups include, but are not limited to, ethynyl (—C≡CH), propynyl (including all isomeric forms, e.g., 1-propynyl (—C≡CCH$_3$) and propargyl (—CH$_2$C≡CH)), butynyl (including all isomeric forms, e.g., 1-butyn-1-yl and 2-butyn-1-yl), pentynyl (including all isomeric forms, e.g., 1-pentyn-1-yl and 1-methyl-2-butyn-1-yl), and hexynyl (including all isomeric forms, e.g., 1-hexyn-1-yl). The R groups can include an alkynyl group. The term alkynyl can also generically refer to alkynylenes when two ends have radicals.

The term "alkynylene" refers to a linear or branched divalent hydrocarbon radical, which contains one or more, in one embodiment, one to five, in another embodiment, one, carbon-carbon triple bond(s). The alkynylene may be optionally substituted with one or more substituents Q as described herein. For example, $C_{2-6}$ alkynylene refers to a linear unsaturated divalent hydrocarbon radical of 2 to 6 carbon atoms or a branched unsaturated divalent hydrocarbon radical of 3 to 6 carbon atoms. In certain embodiments, the alkynylene is a linear divalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched divalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynylene groups include, but are not limited to, ethynylene, propynylene (including all isomeric forms, e.g., 1-propynylene and propargylene), butynylene (including all isomeric forms, e.g., 1-butyn-1-ylene and 2-butyn-1-ylene), pentynylene (including all isomeric forms, e.g., 1-pentyn-1-ylene and 1-methyl-2-butyn-1-ylene), and hexynylene (including all isomeric forms, e.g., 1-hexyn-1-ylene). The R groups can include an alkynylene group.

The term "cycloalkyl" refers to a cyclic monovalent hydrocarbon radical, which may be optionally substituted with one or more substituents Q as described herein. In one embodiment, cycloalkyl groups may be saturated or unsaturated but non-aromatic, and/or bridged, and/or non-bridged, and/or fused bicyclic groups. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclopentenyl, cyclohexyl, cyclohexenyl, cyclohexadienyl, cycloheptyl, cycloheptenyl, bicyclo[2.1.1]hexyl, bicyclo[2.2.1]heptyl, decalinyl, and adamantyl. The R groups can include a cycloalkyl group. The term cycloalkyl can also generically refer to cycloalkylenes when two ends have radicals.

The term "cycloalkylene" refers to a cyclic divalent hydrocarbon radical, which may be optionally substituted with one or more substituents Q as described herein. In one embodiment, cycloalkyl groups may be saturated or unsaturated but non-aromatic, and/or bridged, and/or non-bridged, and/or fused bicyclic groups. In certain embodiments, the cycloalkylene has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkylene groups include, but are not limited to, cyclopropylene (e.g., 1,1-cyclopropylene and 1,2-cyclopropylene), cyclobutylene (e.g., 1,1-cyclobutylene, 1,2-cyclobutylene, or 1,3-cyclobutylene), cyclopentylene (e.g., 1,1-cyclopentylene, 1,2-cyclopentylene, or 1,3-cyclopentylene), cyclohexylene (e.g., 1,1-cyclohexylene, 1,2-cyclohexylene, 1,3-cyclohexylene, or 1,4-cyclohexylene), cycloheptylene (e.g., 1,1-cycloheptylene, 1,2-cycloheptylene, 1,3-cycloheptylene, or 1,4-cycloheptylene), decalinylene, and adamantylene. The R groups can include a cycloalkyl group.

The term "aryl" refers to a monovalent monocyclic aromatic group and/or monovalent polycyclic aromatic group that contain at least one aromatic carbon ring. In certain embodiments, the aryl has from 6 to 20 ($C_6$-20), from 6 to 15 ($C_6$-15), or from 6 to 10 ($C_6$-10) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may be optionally substituted with one or more substituents Q as described herein. The R groups can include an aryl group. The term aryl can also generically refer to arylenes when two ends have radicals.

The term "arylene" refers to a divalent monocyclic aromatic group and/or divalent polycyclic aromatic group that contain at least one aromatic carbon ring. In certain embodiments, the arylene has from 6 to 20 ($C_{6-20}$), from 6 to 15 ($C_{6-15}$), or from 6 to 10 ($C_{6-10}$) ring atoms. Examples of arylene groups include, but are not limited to, phenylene, naphthylene, fluorenylene, azulenylene, anthrylene, phenanthrylene, pyrenylene, biphenylene, and terphenylene. Arylene also refers to bicyclic or tricyclic carbon rings, where one of the rings is aromatic and the others of which may be saturated, partially unsaturated, or aromatic, for example, dihydronaphthylene, indenylene, indanylene, or tetrahydronaphthylene (tetralinylene). In certain embodiments, arylene may be optionally substituted with one or more substituents Q as described herein. The R groups can include an arylene group.

The term "aralkyl" or "arylalkyl" refers to a monovalent alkyl group substituted with one or more aryl groups. In certain embodiments, the aralkyl has from 7 to 30 ($C_{7-30}$), from 7 to 20 ($C_{7-20}$), or from 7 to 16 ($C_{7-16}$) carbon atoms. Examples of aralkyl groups include, but are not limited to, benzyl, 2-phenylethyl, and 3-phenylpropyl. In certain embodiments, aralkyl are optionally substituted with one or more substituents Q as described herein. The R groups can include an aralkyl or arylalkyl group. The term arylalkyl can also generically refer to arylalkylenes when two ends have radicals.

The term "heteroaryl" refers to a monovalent monocyclic aromatic group or monovalent polycyclic aromatic group that contain at least one aromatic ring, wherein at least one aromatic ring contains one or more heteroatoms independently selected from O, S, and N in the ring. Heteroaryl groups are bonded to the rest of a molecule through the aromatic ring. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, heteroaryl may also be optionally substituted with one or more substituents Q as described herein. The R groups can include a heteroaryl group. The term heteroaryl can also generically refer to heteroarylenes when two ends have radicals.

The term "heteroarylene" refers to a divalent monocyclic aromatic group or divalent polycyclic aromatic group that contain at least one aromatic ring, wherein at least one aromatic ring contains one or more heteroatoms independently selected from O, S, and N in the ring. Each ring of a heteroarylene group can contain one or two O atoms, one or two S atoms, and/or one to four N atoms, provided that the total number of heteroatoms in each ring is four or less and each ring contains at least one carbon atom. In certain embodiments, the heteroarylene has from 5 to 20, from 5 to 15, or from 5 to 10 ring atoms. Examples of monocyclic heteroarylene groups include, but are not limited to, furanylene, imidazolylene, isothiazolylene, isoxazolylene, oxadiazolylene, oxadiazolylene, oxazolylene, pyrazinylene, pyrazolylene, pyridazinylene, pyridylene, pyrimidinylene, pyrrolylene, thiadiazolylene, thiazolylene, thienylene, tetrazolylene, triazinylene, and triazolylene. Examples of bicyclic heteroarylene groups include, but are not limited to, benzofuranylene, benzimidazolylene, benzoisoxazolylene, benzopyranylene, benzothiadiazolylene, benzothiazolylene, benzothienylene, benzotriazolylene, benzoxazolylene, furopyridylene, imidazopyridinylene, imidazothiazolylene, indolizinylene, indolylene, indazolylene, isobenzofuranylene, isobenzothicnylene, isoindolylene, isoquinolinylene, isothiazolylene, naphthyridinylene, oxazolopyridinylene, phthalazinylene, pteridinylene, purinylene, pyridopyridylene, pyrrolopyridylene, quinolinylene, quinoxalinylene, quinazolinylene, thiadiazolopyrimidylene, and thienopyridylene. Examples of tricyclic heteroarylene groups include, but are not limited to, acridinylene, benzindolylene, carbazolylene, dibenzofuranylene, perimidinylene, phenanthrolinylene, phenanthridinylene, phenarsazinylene, phenazinylene, phenothiazinylene, phenoxazinylene, and xanthenylene. In certain embodiments, heteroarylene may also be optionally substituted with one or more substituents Q as described herein. The R groups can include a heteroarylene group.

The term "heterocyclyl" or "heterocyclic" refers to a monovalent monocyclic non-aromatic ring system or monovalent polycyclic ring system that contains at least one non-aromatic ring, wherein one or more of the non-aromatic ring atoms are heteroatoms independently selected from O, S, and N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. Heterocyclyl groups are bonded to the rest of a molecule through the non-aromatic ring. In certain embodiments, the heterocyclyl is a monocyclic, bicyclic, tricyclic, or tetracyclic ring system, which may be fused or bridged, and in which nitrogen or sulfur atoms may be optionally oxidized, nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic groups include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocyclic may also be optionally substituted with one or more substituents Q as described herein. The R groups can include a heterocyclic group. The term heterocyclic can also generically refer to heterocyclylenes when both ends have radicals.

The term "heterocyclylene" refers to a divalent monocyclic non-aromatic ring system or divalent polycyclic ring system that contains at least one non-aromatic ring, wherein one or more of the non-aromatic ring atoms are heteroatoms independently selected from O, S, and N; and the remaining ring atoms are carbon atoms. In certain embodiments, the heterocyclylene group has from 3 to 20, from 3 to 15, from 3 to 10, from 3 to 8, from 4 to 7, or from 5 to 6 ring atoms. In certain embodiments, the heterocyclylene is a monocyclic, bicyclic, tricyclic, or tetracyclic ring system, which may be fused or bridged, and in which nitrogen or sulfur atoms may be optionally oxidized, nitrogen atoms may be optionally quaternized, and some rings may be partially or fully saturated, or aromatic. The heterocyclylene may be attached to the main structure at any heteroatom or carbon atom which results in the creation of a stable compound. Examples of such heterocyclylene groups include, but are not limited to, azepinylene, benzodioxanylene, benzodioxolylene, benzofuranonylene, benzopyranonylene, benzopyranylene, benzotetrahydrofuranylene, benzotetrahydrothicnylene, benzothiopyranylene, benzoxazinylene, β-carbolinylene, chromanylene, chromonylene, cinnolinylene, coumarinylene, decahydroisoquinolinylene, dihydrobenzisothiazinylene, dihydrobenzisoxazinylene, dihydrofurylene, dihydroisoindolylene, dihydropyranylene, dihydropyrazolylene, dihydropyrazinylene, dihydropyridinylene, dihydropyrimidinylene, dihydropyrrolylene, dioxolanylene, 1,4-dithianylene, furanonylene, imidazolidinylene, imidazolinylene, indolinylene, isobenzotetrahydrofuranylene, isobenzotetrahydrothienylene, isochromanylene, isocoumarinylene, isoindolinylene, isothiazolidinylene, isoxazolidinylene, morpholinylene, octahydroindolylene, octahydroisoindolylene, oxazolidinonylene, oxazolidinylene, oxiranylene, piperazinylene, piperidinylene, 4-piperidonylene, pyrazolidinylene, pyrazolinylene, pyrrolidinylene, pyrrolinylene, quinuclidinylene, tetrahydrofurylene, tetrahydroisoquinolinylene, tetrahydropyranylene, tetrahydrothienylene, thiamorpholinylene, thiazolidinylene, tetrahydroquinolinylene, and 1,3,5-trithianylene. In certain embodiments, heterocyclic may also be optionally substituted with one or more substituents Q as described herein. The R groups can include a heterocyclylene group.

The term "halogen", "halide" or "halo" refers to fluorine, chlorine, bromine, and/or iodine. The R groups can include a halogen group.

The term "optionally substituted" is intended to mean that a group or substituent, such as an alkyl, alkylene, heteroalkylene, alkenyl, alkenylene, heteroalkenylene, alkynyl, alkynylene, cycloalkyl, cycloalkylene, aryl, arylene, aralkyl, heteroaryl, heteroarylene, heterocyclyl, or heterocyclylene group, may be substituted with one or more substituents Q, each of which is independently selected from, e.g., (a) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (b) oxo (=O), halo, cyano (—CN), nitro (—NO$_2$), C(O)R$^a$, C(O)OR$^a$, C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^a$; or (iii) R$^b$ and R$^c$ together with the N atom to which they are attached form heteroaryl or heterocyclyl, optionally substituted with one or more, in one embodiment, one, two, three, or four, substituents $Q^a$. As used herein, all R groups that can be substituted are "optionally substituted," unless otherwise specified.

In one embodiment, each $Q^a$ is independently selected from the group consisting of (a) oxo, cyano, halo, and nitro; and (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)R$^e$, C(O)OR$^e$, C(O)NR$^f$R$^g$, —C(NR$^e$)NR$^f$R$^g$, —OR$^e$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^e$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) R$^f$ and R$^g$ together with the N atom to which they are attached form heteroaryl or heterocyclyl.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of one enantiomer and about 5% or less of the other enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The term "isotopic variant" refers to a compound that contains an unnatural proportion of an isotope at one or more of the atoms that constitute such compounds. In certain embodiments, an "isotopic variant" of a compound contains unnatural proportions of one or more isotopes, including, but not limited to, hydrogen ($^1$H), deuterium ($^2$H), tritium ($^3$H), carbon-11 ($^{11}$C), carbon-12 ($^{12}$C), carbon-13 ($^{13}$C), carbon-14 ($^{14}$C), nitrogen-13 ($^{13}$N), nitrogen-14 ($^{14}$N) nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine-123 ($^{123}$I), iodine-125 ($^{125}$I) iodine-127 ($^{127}$I), iodine-129 ($^{129}$I), and iodine-131 ($^{131}$I). In certain embodiments, an "isotopic variant" of a compound is in a stable form, that is, non-radioactive. In certain embodiments, an "isotopic variant" of a compound contains unnatural proportions of one or more isotopes, including, but not limited to, hydrogen ($^1$H), deuterium ($^2$H), carbon-12 ($^{12}$C), carbon-13 ($^{13}$C), nitrogen-14 ($^{14}$N), nitrogen-15 ($^{15}$N), oxygen-16 ($^{16}$O), oxygen-17 ($^{17}$O), oxygen-18 ($^{18}$O), fluorine-17 ($^{17}$F), phosphorus-31 ($^{31}$P), sulfur-32 ($^{32}$S), sulfur-33 ($^{33}$S), sulfur-34 ($^{34}$S), sulfur-36 ($^{36}$S), chlorine-35 ($^{35}$Cl), chlorine-37 ($^{37}$Cl), bromine-79 ($^{79}$Br), bromine-81 ($^{81}$Br), and iodine-127 ($^{127}$I). In certain embodiments, an "isotopic variant" of a compound is in an unstable form, that is, radioactive. In certain embodiments, an "isotopic variant" of a compound contains unnatural proportions of one or more isotopes, including, but not limited to, tritium ($^3$H), carbon-11 ($^{11}$C), carbon-14 ($^{14}$C), nitrogen-13 ($^{13}$N), oxygen-14 ($^{14}$O), oxygen-15 ($^{15}$O), fluorine-18 ($^{18}$F), phosphorus-32 ($^{32}$P), phosphorus-33 ($^{33}$P), sulfur-35 ($^{35}$S), chlorine-36 ($^{36}$Cl), iodine-123 ($^{123}$I), iodine-125 ($^{125}$I), iodine-129 ($^{129}$I), and iodine-131 ($^{131}$I). It will be understood that, in a compound as provided herein, any hydrogen can be $^2$H, for example, or any carbon can be $^{13}$C, as example, or any nitrogen can be $^{15}$N, as example, and any oxygen can be $^{18}$O, where feasible according to the judgment of one of skill. In certain embodiments, an "isotopic variant" of a compound contains unnatural proportions of deuterium. The R groups can include isotopic variants.

The term "solvate" refers to a complex or aggregate formed by one or more molecules of a solute, e.g., a compound provided herein, and one or more molecules of a solvent, which present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The phrase "a single enantiomer, a racemic mixture, a mixture of diastereomers, or an isotopic variant thereof; or a pharmaceutically acceptable salt, solvate, or prodrug thereof" has the same meaning as the phrase "a single enantiomer, a racemic mixture, a mixture of diastereomers, or an isotopic variant of the compound referenced therein; or a pharmaceutically acceptable salt, solvate, or prodrug of the compound referenced therein, or a single enantiomer, a racemic mixture, a mixture of diastereomers, or an isotopic variant of the compound referenced therein."

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety.

The invention claimed is:

1. A compound comprising:
a structure of Formula 9, or a salt, stereoisomer, tautomer, polymorph, or solvate thereof:

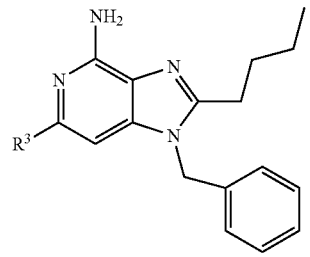

Formula 9 wherein:
$R^3$ is selected from:
hydrogen;
—C(O)$R^{1a}$, —C(O)CH(N$R^{1b}R^{1c}$)$R^{1a}$, —C(O)CH(N($R^{1c}$)C (O)$R^{1b}$)$R^{1a}$, —C(O)CH(N($R^{1c}$)C(O)O$R^{1b}$)$R^{1a}$, —C(O)CH(N($R^{1c}$)C(O)N$R^{1b}R^{1d}$)$R^{1a}$, —C(O)O$R^{1a}$, —C(O)N$R^{1b}R^{1c}$, —C(N$R^{1a}$)N$R^{1b}R^{1c}$, —P(O)(O$R^{1a}$)$R^{1d}$, —CH$_2$P(O)(O$R^{1a}$)$R^{1d}$, —S(O)$R^{1a}$, —S(O)$_2R^{1a}$, —S(O)N$R^{1b}R^{1c}$, or —S(O)$_2$N$R^{1b}R^{1c}$; or $C_1$-$C_{24}$ alkyl, $C_2$-$C_{24}$ alkenyl, $C_2$-$C_{24}$ alkynyl, $C_3$-$C_{20}$ cycloalkyl, $C_5$-$C_{20}$ aryl, $C_5$-$C_{20}$ polyaryl, $C_6$-$C_{24}$ alkaryl, $C_6$-$C_{24}$ aralkyl, heteroaryl, heterocyclyl, halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, $C_2$-$C_{24}$ alkylcarbonyl, $C_6$-$C_{20}$ arylcarbonyl, acyloxy, $C_2$-$C_{24}$ alkoxycarbonyl, $C_6$-$C_{20}$ aryloxycarbonyl, halocarbonyl, $C_2$-$C_{24}$ alkylcarbonato, $C_6$-$C_{20}$ arylcarbonato, carboxy, carboxylato, carbamoyl, mono-($C_1$-$C_{24}$ alkyl)-substituted carbamoyl, di-($C_1$-$C_{24}$ alkyl)-substituted carbamoyl, mono-substituted arylcarbamoyl, thiocarbamoyl, carbamido, cyano, isocyano, cyanato, isocyanato, isothiocyanato, azido, formyl, thioformyl, amino, mono- and di-($C_1$-$C_{24}$ alkyl)-substituted amino, mono- and di-($C_5$-$C_{20}$ aryl)-substituted amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, or phosphino; and combinations thereof;
wherein $R^3$ is optionally substituted by a substituent Q, which substituent Q is defined as $R^3$; and
wherein $R^{1a}$, $R^{1b}$, $R^{1c}$, or $R^{1d}$ are each independently as defined for $R^3$.

2. The compound of claim 1, wherein R³ is selected from:

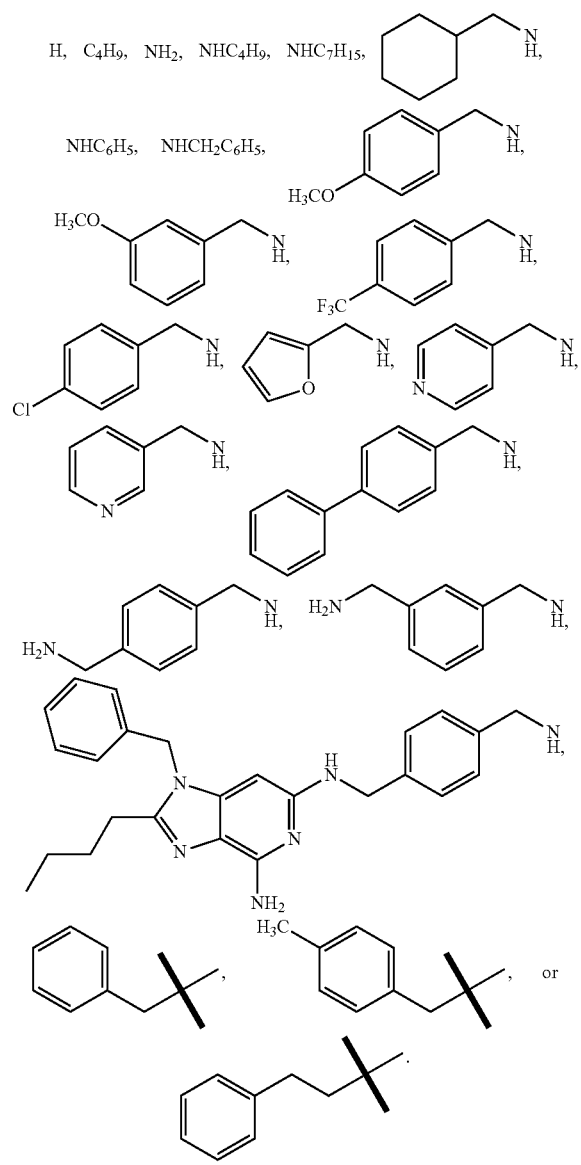

3. The compound of Formula 9 of claim 1, wherein the compound is selected from one of compounds 5, 19a, 19b, 19c, 19d, 19e, 19f, 19g, 19h, 19i, 19j, 19k, 19l, 19m, 19o, 19p, 19q, 19r, 23a, 23g, 23h and 23j, or a salt, stereoisomer, tautomer, polymorph, or solvate thereof.

4. A pharmaceutical composition comprising:
   a compound from claim 1; and
   a pharmaceutically acceptable carrier.

5. The pharmaceutical composition of claim 4, further comprising an immunological vaccine agent having an antigen and immunogenicity, wherein the compound is an adjuvant for the immunological vaccine agent.

6. A method of agonizing a Toll-Like Receptor (TLR), the method comprising:
   providing a compound of claim 1 to a TLR in an amount sufficient to agonize the TLR.

7. A method of improving vaccination, the method comprising:
   administering an immunological vaccine agent having an antigen and immunogenicity to a subject along with a compound of claim 1 in an amount sufficient to function as an adjuvant with regard to the immunological vaccine agent.

8. A method of activating an immune system, the method comprising:
   administering an immunological agent to a subject along with a compound of claim 1 in an amount sufficient to function as an adjuvant with regard to the immunological agent.

9. A method of treating allergic bronchitis, comprising:
   administering to a subject a compound of claim 1.

10. A method of treating bronchospastic disorder, comprising:
    administering to a subject a compound of claim 1.

11. The compound of claim 1, wherein the compound is Compound 19K, or a salt, stereoisomer, tautomer, polymorph, or solvate thereof, Compound 19K

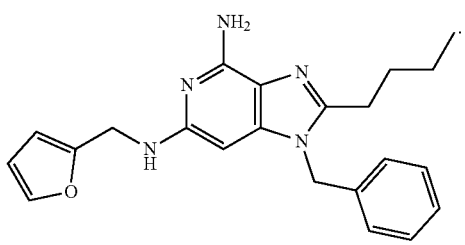

12. The pharmaceutical composition of claim 4, wherein R³ is selected from:

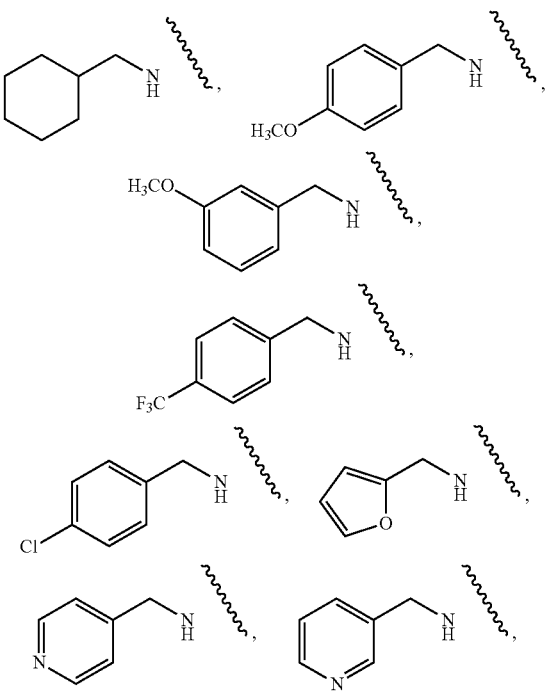

89
-continued

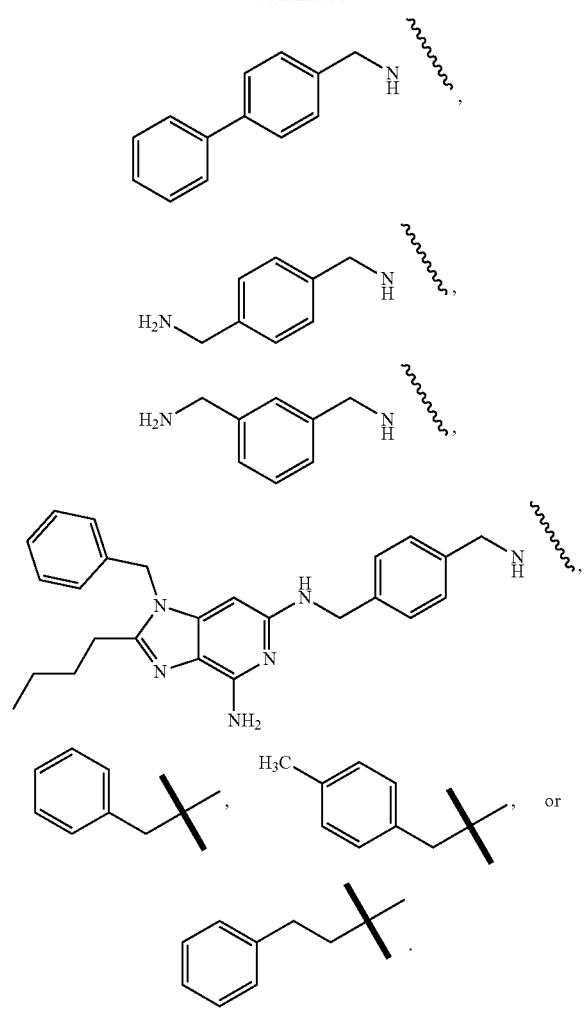

13. The compound of claim 1, wherein R³ is selected from:

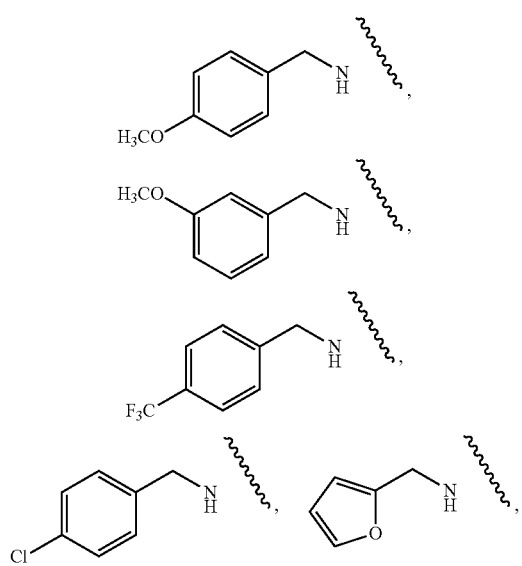

90
-continued

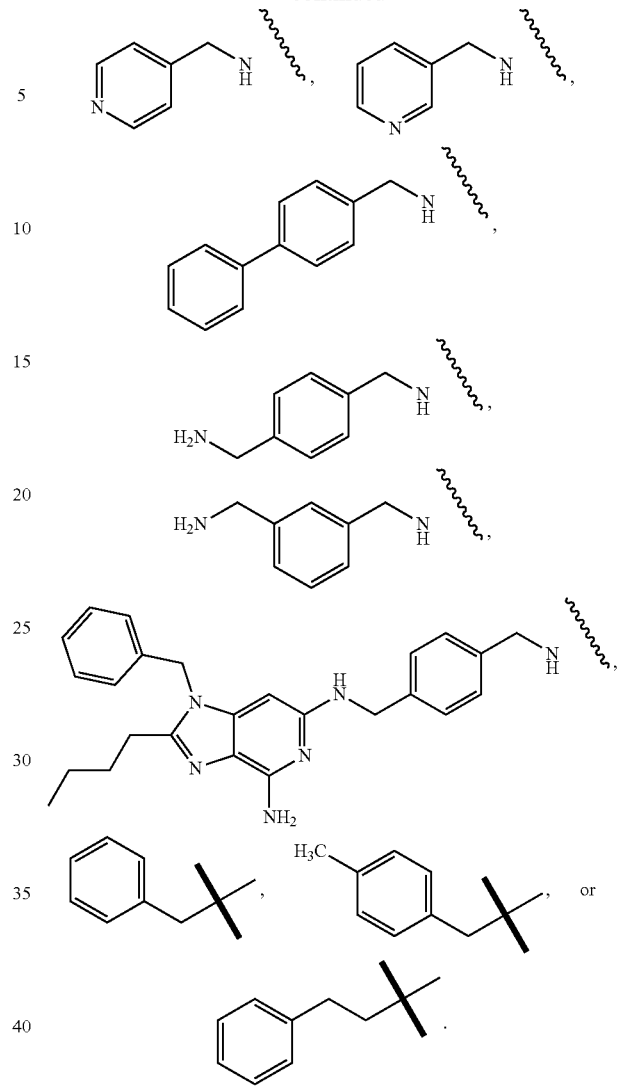

14. The compound of claim 1, wherein R³ is selected from:
H, C₄H₉, NH₂ NHC₄H₉, NHC₇H₁₅, $$\text{(cyclohexyl-CH}_2\text{-NH)}$$

NHC₆H₅, and NHCH₂C₆H₅.

15. A pharmaceutical composition comprising:
a compound from claim 3, and
a pharmaceutically acceptable carrier.

16. The pharmaceutical composition of claim 15, further comprising an immunological vaccine agent having an antigen and immunogenicity, wherein the compound is an adjuvant for the immunological vaccine agent.

17. A pharmaceutical composition comprising:
a compound from claim 13; and
a pharmaceutically acceptable carrier.

18. The pharmaceutical composition of claim 17, further comprising an immunological vaccine agent having an antigen and immunogenicity, wherein the compound is an adjuvant for the immunological vaccine agent.

19. A pharmaceutical composition comprising:
a compound from claim 14; and
a pharmaceutically acceptable carrier.

20. The pharmaceutical composition of claim 18, further comprising an immunological vaccine agent having an antigen and immunogenicity, wherein the compound is an adjuvant for the immunological vaccine agent.

* * * * *